(12) United States Patent
Yaffe et al.

(10) Patent No.: US 12,053,636 B2
(45) Date of Patent: Aug. 6, 2024

(54) CONNECTORS FOR HIGH DENSITY NEURAL INTERFACES

(71) Applicant: Verily Life Sciences LLC, South San Francisco, CA (US)

(72) Inventors: Benjamin K. Yaffe, San Francisco, CA (US); Bo Lu, Santa Clara, CA (US)

(73) Assignee: VERILY LIFE SCIENCES LLC, South San Francisco, CA (US)

( * ) Notice: Subject to any disclaimer, the term of this patent is extended or adjusted under 35 U.S.C. 154(b) by 451 days.

(21) Appl. No.: 17/605,493

(22) PCT Filed: Apr. 14, 2020

(86) PCT No.: PCT/US2020/028063
§ 371 (c)(1),
(2) Date: Oct. 21, 2021

(87) PCT Pub. No.: WO2020/219295
PCT Pub. Date: Oct. 29, 2020

(65) Prior Publication Data
US 2022/0212016 A1 Jul. 7, 2022

Related U.S. Application Data

(60) Provisional application No. 62/838,550, filed on Apr. 25, 2019.

(51) Int. Cl.
*A61N 1/37* (2006.01)
*A61N 1/05* (2006.01)
(Continued)

(52) U.S. Cl.
CPC ......... *A61N 1/3752* (2013.01); *A61N 1/0531* (2013.01); *A61N 1/0534* (2013.01);
(Continued)

(58) Field of Classification Search
CPC .. A61N 1/3752; A61N 1/0531; A61N 1/0534; A61N 1/0551; H01B 3/305; H01B 3/306
See application file for complete search history.

(56) References Cited

U.S. PATENT DOCUMENTS 7,890,175 B1 * 2/2011 Rey ................... H01R 13/5224
607/37
7,892,039 B2 * 2/2011 Feeney .................. H01R 24/58
439/669
(Continued)

FOREIGN PATENT DOCUMENTS

| WO | 03066160 | 8/2003 |
| WO | 2018156953 | 8/2018 |
| WO | 2018223019 | 12/2018 |

OTHER PUBLICATIONS

Application No. PCT/US2020/028063, International Search Report and Written Opinion, Mailed on Jul. 23, 2020, 7 pages.

*Primary Examiner* — Phuong Chi Thi Nguyen
(74) *Attorney, Agent, or Firm* — Kilpatrick Townsend & Stockton LLP

(57) ABSTRACT

The present disclosure relates to connectors for high density neural interfaces and methods of microfabricating the connectors. Particularly, aspects of the present disclosure are directed to a connector having a core and a supporting structure wrapped around at least a portion of the core. The supporting structure may have a first layer of a high temperature liquid crystal polymer, and the second layer of a low temperature liquid crystal polymer that is reflowed to attach the supporting structure to the core. Conductive traces are buried between the first layer and the second layer, and the conductive traces terminate at conductive contacts formed on a surface of the first layer. The connector may (Continued)

have a predetermined shape or profile, which facilitates alignment and insertion of the connector into a header of a neurostimulator.

20 Claims, 34 Drawing Sheets

(51) Int. Cl.
- *A61N 1/375* (2006.01)
- *H01B 3/30* (2006.01)
- *H01B 3/42* (2006.01)
- *H01R 13/642* (2006.01)
- *H01R 13/6598* (2011.01)
- *H01R 24/58* (2011.01)
- *H01R 107/00* (2006.01)

(52) U.S. Cl.
CPC .......... *A61N 1/0551* (2013.01); *H01B 3/305* (2013.01); *H01B 3/306* (2013.01); *H01B 3/307* (2013.01); *H01B 3/427* (2013.01); *H01R 13/642* (2013.01); *H01R 13/6598* (2013.01); *H01R 24/58* (2013.01); *H01R 2107/00* (2013.01)

(56) References Cited

U.S. PATENT DOCUMENTS

| | | | |
|---|---|---|---|
| 8,412,330 B2 * | 4/2013 | Kast | A61N 1/3752 607/37 |
| 8,419,481 B2 * | 4/2013 | Chai | H01R 24/58 439/668 |
| 8,521,290 B2 * | 8/2013 | North | H01R 31/02 607/38 |
| 9,956,394 B2 * | 5/2018 | Howard | A61N 1/05 |
| 2010/0057175 A1 | 3/2010 | McDonald et al. | |
| 2016/0030735 A1 | 2/2016 | Ouchouche | |

* cited by examiner

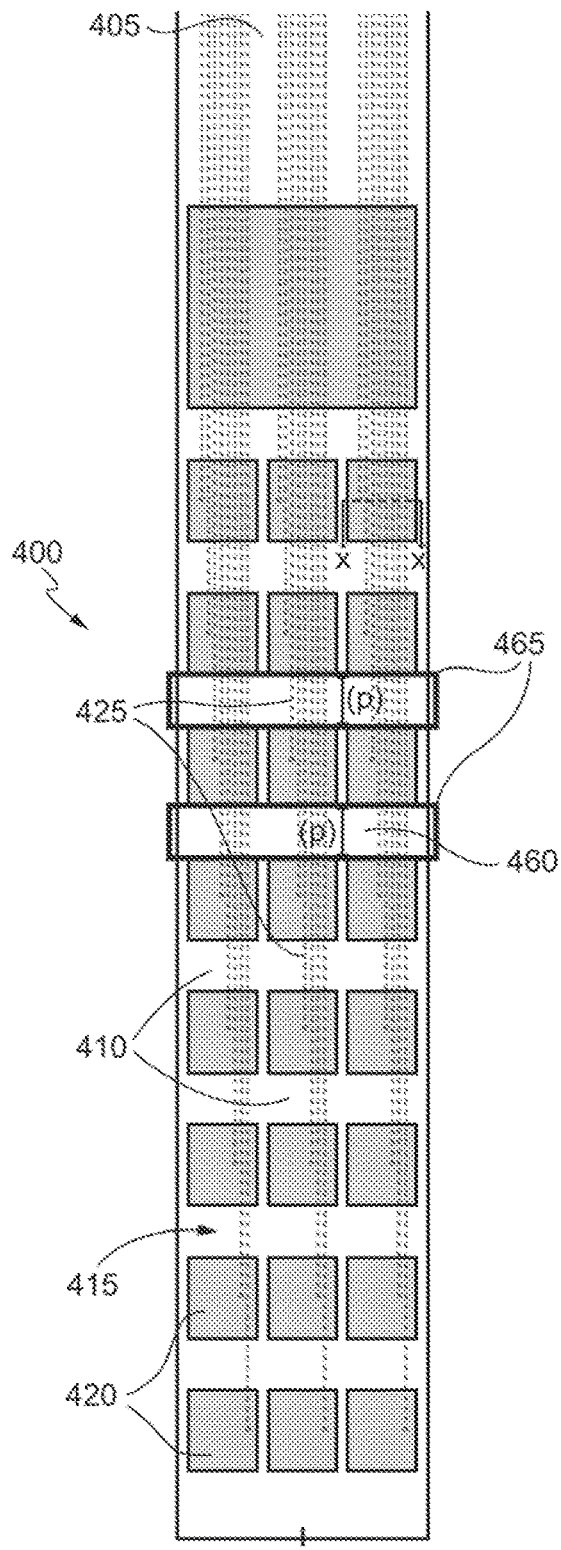
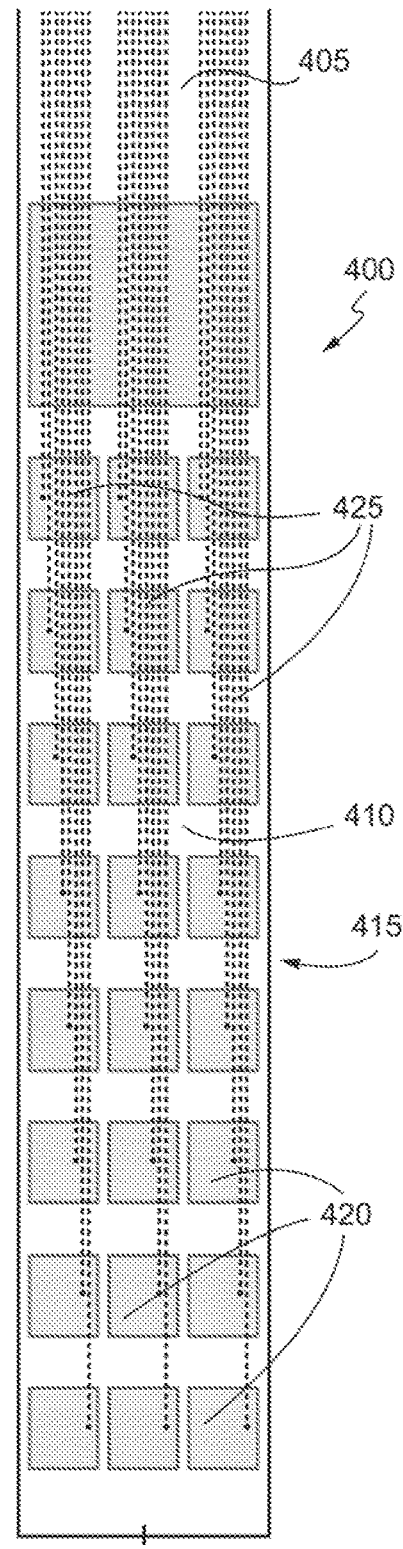
FIG. 4A
FIG. 4B

CONNECTORS FOR HIGH DENSITY NEURAL INTERFACES

CROSS-REFERENCE TO RELATED APPLICATION

The present application is a national-phase application under 35 U.S.C. 371 of International Application No. PCT/US2020/028063, filed Apr. 14, 2020, which claims priority and benefit from U.S. Provisional Application No. 62/838,550, filed Apr. 25, 2019, the entire contents of which are incorporated herein by reference for all purposes.

FIELD

The present disclosure relates to implantable neuromodulation devices and methods of fabrication, and in particular to connectors for high density neural interfaces and methods of microfabricating the connectors.

BACKGROUND

Normal neural activity is an intricate balance of electrical and chemical signals, which can be disrupted by a variety of insults (genetic, chemical or physical trauma) to the nervous system, causing cognitive, motor and sensory impairments. Similar to the way a cardiac pacemaker or defibrillator corrects heartbeat abnormalities, neuromodulation therapies help to reestablish normal neural balance. In particular instances, neuromodulation therapies utilize medical device technologies to enhance or suppress activity of the nervous system for the treatment of disease. These technologies include implantable as well as non-implantable neuromodulation devices and systems that deliver electrical, chemical or other agents to reversibly modify brain and nerve cell activity. The most common neuromodulation therapy is spinal cord stimulation to treat chronic neuropathic pain, in addition to chronic pain relief, some examples of neuromodulation therapies include deep brain stimulation for essential tremor, Parkinson's disease, dystonia, epilepsy and psychiatric disorders such as depression, obsessive compulsive disorder and Tourette syndrome; sacral nerve stimulation for pelvic disorders and incontinence, vagus nerve stimulation for rheumatoid arthritis; gastric and colonic stimulation for gastrointestinal disorders such as dysmotility or obesity; vagus nerve stimulation for epilepsy, obesity or depression; carotid artery stimulation for hypertension, and spinal cord stimulation for ischemic disorders such as angina and peripheral vascular disease.

Neuromodulation devices and systems tend to have a similar form factor, derived from their predecessors, e.g. the pacemaker or defibrillator. Such neuromodulation devices and systems typically consist of an implant comprising a neurostimulator having electronics connected to a lead assembly that delivers electrical pulses to electrodes interfaced with nerves or nerve bundles via an electrode assembly. The lead assembly is typically formed of a conductive material and takes the form of an insulated wire (e.g., a dedicated channel) connected to the electrodes via a first connector on one end (e.g., a distal end) and the electronics of the neurostimulator via a second connector on another end (e.g., a proximal end). In some instances (e.g., deep implants), the lead assembly comprises additional conductors and connectors such as extension wires or a cable connected via connectors between the electrodes and the electronics of the neurostimulator.

Conventional neuromodulation devices include between four and sixteen electrodes, and thus typically include four to sixteen channels or wires connected respectively to the electrodes at the distal end and the electronics of the neurostimulator at the proximal end. However, there is a need for high density neural interfaces that include greater than sixteen electrodes to interface with larger tissue volumes, to recruit smaller populations of neurons for recording, or to provide more targeted therapy by tailoring the electrical stimulation parameters and activated tissue volume. Increasing the density or number of electrodes can increase the number of channels or wires needed to connect the electrodes and the electronics of the neurostimulator. In order to implement high channel or wire counts, there is a need for reliable electrical connections that can maintain contact and electrical isolation in a subject body (e.g., a patient body) for many years. Typically, a lead assembly containing a high channel or wire count needs to be permanently connected to the electronics. However, this is not ideal because the electronics need to be replaced every few years to upgrade them or to replace batteries, and surgeons have a strong preference not to remove the lead assembly from the neural tissue due to the risk to the patient. Therefore, there is a need for reliable and non-permanent connectors for lead assemblies having high density neural interfaces.

BRIEF SUMMARY

In various embodiments, a lead assembly is provided that comprises: a cable comprising a proximal end, a distal end, and first conductive traces; a connector comprising a core and a supporting structure wrapped around at least a portion of the core, where: the connector is located at the proximal end of the cable; the supporting structure comprises a first layer of dielectric material and a second layer of dielectric material; the first layer of dielectric material is a high temperature liquid crystal polymer; the second layer of dielectric material is a low temperature liquid crystal polymer that is reflowed to attach the supporting structure to the core; second conductive traces are buried between the first layer of dielectric material and the second layer of dielectric material; the second conductive traces terminate at conductive contacts formed on a surface of the first layer of dielectric material; and the connector has a predetermined shape or profile, which facilitates alignment and insertion of the connector into a header; and an electrode assembly located at the distal end of the cable, the electrode assembly comprising electrodes electrically connected to the conductive contacts via the first conductive traces and the second conductive traces.

In some embodiments, the connector further comprises multiple sectors extending along the surface of the first dielectric layer, and one or more contacts of the conductive contacts are arranged in each sector of the multiple sectors.

In some embodiments, the conductive contacts are arranged as split annular rings positioned around an axis of the connector and exposed on the surface of the first dielectric layer, and a first portion of the split annular rings is disposed in a first sector of the multiple sectors and a second portion of the split annular rings is disposed in a second sector of the multiple sectors.

In some embodiments, the predetermined shape or profile is a "D"-shaped profile, the contacts are arranged as split rings on the surface of the first layer of dielectric material in the curved portion of the "D"-shaped profile, and the flat portion of the "D"-shaped profile is an indexing feature for keying during insertion of the connector into the header.

In some embodiments, the predetermined shape or profile is a notched profile, the contacts are arranged as split rings on the surface of the first layer of dielectric material in a curved portion of the notched profile, and a notch of the notched profile is an indexing feature for keying during insertion of the connector into the header.

In some embodiments, a first portion of the split annular rings is disposed in a first sector of the multiple sectors and a second portion of the split annular rings is disposed in a second sector of the multiple sectors. Optionally, each split annular ring is spaced apart from one another on the surface by a region of the first layer of the dielectric material. Optionally, a width of the region of the first layer of the dielectric material that separates each split annular ring is between 0.1 mm to 10 mm.

In some embodiments, the predetermined shape or profile is a square shaped profile having quadruple planar sectors, and one or more contacts of the contacts are arranged in each sector of the quadruple planar sectors. Optionally, the connector further comprises one or more additional contacts with impedance, resistive, or ohmic fiducials to provide orientation queues of the contacts.

In some embodiments, the connector further comprises a scaling feature, which is a section of the predetermined shape or profile at a distal end of the connector, and the sealing feature comprises a different material, texture, or stiffness from the core and the supporting structure to engage a scaling surface of the header.

In some embodiments, the connector further comprises a retention feature for mechanical retention or connection with a corresponding feature in the header to retain insertion of the connector in the header.

In various embodiments, a header and lead assembly is provided comprising: a connector comprising a core and a first supporting structure wrapped around at least a portion of the core, where: the first supporting structure comprises a first layer of dielectric material and a second layer of dielectric material; the first layer of dielectric material is a high temperature liquid crystal polymer; the second layer of dielectric material is a low temperature liquid crystal polymer that is reflowed to attach the first supporting structure to the core; first conductive traces are buried between the first layer of dielectric material and the second layer of dielectric material; the first conductive traces terminate at first conductive contacts formed on a surface of the first dielectric layer; and the connector has a first predetermined shape or profile; a header comprising a second supporting structure, where: the second supporting structure comprises one or more layers of polymer; second conductive traces are buried between the one or more layers of polymer; the second conductive traces terminate at second conductive contacts formed on a surface of the one or more layers of polymer; and the header has a second predetermined shape or profile structured to receive the first predetermined shape or profile of the connector; and a clip structured to hold the first conductive contacts in electrical contact with the second conductive contacts.

In some embodiments, the clip is one or more clip springs or spring-fibers arranged into a comb or rib-cage arrangement on an outside of the second supporting structure, and the clip springs or spring-fibers have a spring force that exerts a clasping pressure on the second supporting structure to electrically connect the header to the connector.

In some embodiments, the one or more layers of polymer have a thickness of from 0.5 µm to 250 µm, which allows for the spring force of the clip to be distributed across all of the first conductive contacts and the second conductive contacts.

In some embodiments, the header and lead assembly further comprises a cable comprising a proximal end, a distal end, and third conductive traces, where the connector is located at the proximal end of the cable.

In some embodiments, the header and lead assembly further comprises an electrode assembly located at the distal end of the cable, the electrode assembly comprising electrodes electrically connected to the second conductive traces via the third conductive traces, the first conductive traces, the first conductive contacts, and the second conductive contacts.

In some embodiments, the connector further comprises multiple sectors extending along the surface of the first layer of dielectric material, and one or more contacts of the first conductive contacts are arranged in each sector of the multiple sectors.

In some embodiments, the first conductive contacts are arranged as split rows positioned in columns and exposed on the surface of the first layer of dielectric material, and a first portion of the split rows is disposed in a first sector of the multiple sectors and a second portion of the split rows is disposed in a second sector of the multiple sectors. Optionally, the first sector is located on a first side of the connector and the second sector is located on a second side of the connector.

In some embodiments, the first predetermined shape or profile is a blade shape with the first supporting structure folded over the core, and the first conductive contacts face outward on the surface of the first layer of dielectric material.

In some embodiments, the second predetermined shape or profile is a "U"-shape, and the second conductive contacts face inward on the surface of the one or more layers of polymer.

In various embodiments, a lead assembly is provided comprising: a first cable comprising a proximal end and a distal end; a second cable comprising a proximal end and a distal end; a connection assembly comprising: a first connector comprising a core and a first supporting structure wrapped around at least a portion of the core, where: the first connector is located at the proximal end of the first cable; the first supporting structure comprises a first layer of dielectric material and a second layer of dielectric material; the first layer of dielectric material is a high temperature liquid crystal polymer; the second layer of dielectric material is a low temperature liquid crystal polymer that is reflowed to attach the first supporting structure to the core; first conductive traces are buried between the first layer of dielectric material and the second layer of dielectric material; and the first conductive traces terminate at first conductive contacts formed on a surface of the first layer of dielectric material; a second connector comprising a second supporting structure, where: the second connector is located at the distal end of the second cable; the second supporting structure comprises a one or more layers of polymer; second conductive traces are buried between the one or more layers of polymer; and the second conductive traces terminate at second conductive contacts formed on a surface of the one or more layers of polymer; and one or more attachment features that hold the first connector in physical contact with the second connector such that the first conductive contacts are in electrical contact with the second conductive contacts.

In some embodiments, the connection assembly further comprises a housing comprising: a first half portion, a second half portion, a proximal port, and a distal port, wherein the first cable is inserted into the connection assembly through the distal port, the second cable is inserted into the connection assembly through the proximal port, and the first half portion is attached to the second half portion with the one or more attachment features.

In some embodiments, the first half portion comprises alignment pins, a seal, and a first compliant pad, the second half comprises the one or more attachment features and a second compliant pad, and the first compliant pad and the second compliant pad assist the one or more attachment features in holding the first connector in physical contact with the second connector.

In some embodiments, the first connector further comprises first alignment holes that fit over the alignment pins, and the second connector further comprises second alignment holes that fit over the alignment pins.

In some embodiments, the one or more layers of polymer have a thickness of from 0.5 μm to 250 μm, which allows for a spring force of the first compliant pad and second compliant pad to be distributed across all of the first conductive contacts and the second conductive contacts.

In some embodiments, the first cable further comprises third conductive traces, and the second cable further comprises fourth conductive traces. Optionally, the lead assembly further comprises an electrode assembly located at the distal end of the first cable, the electrode assembly comprising electrodes electrically connected to the fourth conductive traces via the third conductive traces, the first conductive traces, the first conductive contacts, the second conductive contacts, and the second conductive traces.

In some embodiments, the first connector further comprises multiple sectors extending along the surface of the first layer of dielectric material, and one or more contacts of the first conductive contacts are arranged in each sector of the multiple sectors.

In some embodiments, the first conductive contacts are arranged as split rows positioned in columns and exposed on the surface of the first layer of dielectric material, and a first portion of the split rows is disposed in a first sector of the multiple sectors and a second portion of the split rows is disposed in a second sector of the multiple sectors.

In some embodiments, the first sector is located on a first side of the connector and the second sector is located on a second side of the connector. In some embodiments, the first connector comprises a first predetermined shape or profile, which is a blade shape with the first supporting structure folded over the core, and the first conductive contacts face outward on the surface of the first layer of dielectric material.

In some embodiments, the second connector comprises a second predetermined shape or profile, which is a "U"-shape, and the second conductive contacts face inward on the surface of the one or more layers of polymer.

In various embodiments, a lead assembly is provided comprising: a high density cable comprising a proximal end and a distal end; a low density cable comprising a proximal end and a distal end; and a connector comprising: a package comprising a housing, one or more multiplexor chips, distal feedthroughs connected to distal channel inputs of the one or more multiplexor chips, and proximal feedthroughs connected to proximal channel inputs of the one or more multiplexor chips; and a connection assembly comprising a supporting structure, wherein: the connector is located at the proximal end of the high density cable and the distal end of the low density cable; the supporting structure comprises a first layer of dielectric material and a second layer of dielectric material; the first layer of dielectric material is a low temperature liquid crystal polymer that is reflowed to attach the supporting structure to the package; the second layer of dielectric material is a high temperature liquid crystal polymer; distal conductive traces are buried between the first layer of dielectric material and the second layer of dielectric material; proximal conductive traces are buried between the first layer of dielectric material and the second layer of dielectric material; the distal conductive traces connected to the high density cable, and the distal conductive traces terminate at distal conductive contacts formed on a surface of the second layer of dielectric material; the proximal conductive traces connected to the low density cable, and the proximal conductive traces terminate at proximal conductive contacts formed on the surface of the second layer of dielectric material; the distal conductive contacts are electrically connected to the distal feedthroughs; and the proximal conductive contacts are electrically connected to the proximal feedthroughs.

In some embodiments, the high density cable further comprises first conductive traces, and the low density cable further comprises second conductive traces. Optionally, the lead assembly further comprises an electrode assembly located at the distal end of the high density cable, the electrode assembly comprising electrodes electrically connected to the second conductive traces via the first conductive traces, the distal conductive traces, the distal conductive contacts, the distal feedthroughs, the one or more multiplexor chips, the proximal feedthroughs, the proximal conductive contacts, and the proximal conductive traces.

BRIEF DESCRIPTION OF THE DRAWINGS

The present invention will be better understood in view of the following non-limiting figures, in which:

FIGS. 4A-4D show a top view, a bottom view, and cross-sectional side views illustrating a design and method of fabricating multi-sector connectors in accordance with various embodiments;

DETAILED DESCRIPTION

I. Introduction

Figure 1:
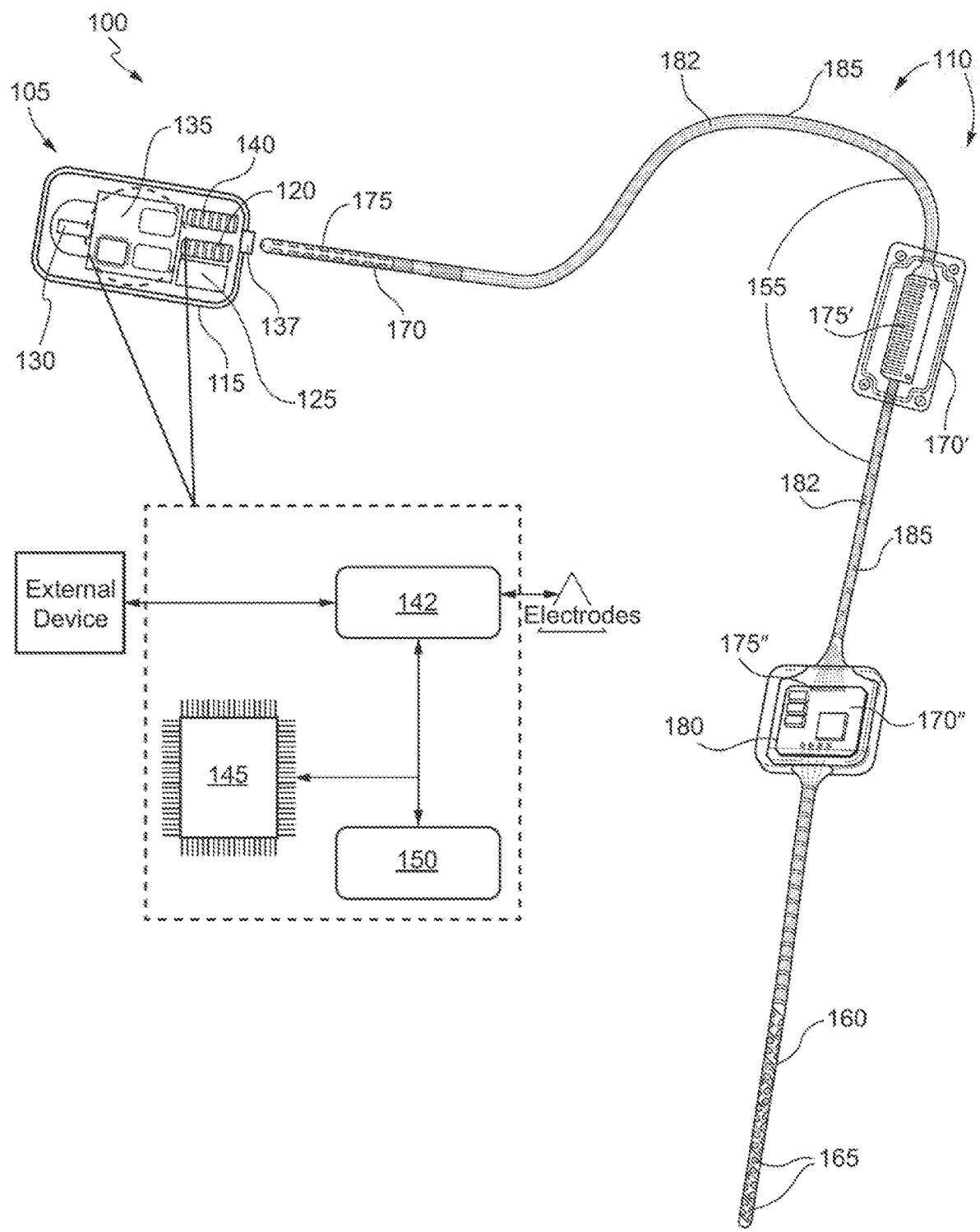
FIG. 1 shows a neuromodulation system in accordance with various embodiments.

The following disclosure describes connectors for high density neural interfaces and methods of microfabricating the connectors. In some embodiments, a connector is located at a proximal end of the lead assembly and used to connect the lead assembly with the neurostimulator. In other embodiments, one or more connectors are located at the proximal end and/or distal end of one or more lead bodies and used to connect one or more lead bodies thereby extending an overall length of the lead assembly. In yet other embodiments, a connector is located at the proximal end or distal end of one or more lead bodies and used to connect a multiplexer chip to the lead assembly. As used herein, the term "proximal" or "proximal end" refers to a first end of the main body, while the term "distal" or "distal end" refers to a second end opposing the first end. For example, the proximal end may be an end of the main body, which is closest to the user, and the distal end may be an end of the main body, which is furthest from the user.

The connectors may be fabricated using microfabricating techniques. In certain embodiments, the connector is fabricated as a monolithic structure. As used herein, the phrase "monolithic" refers to a device fabricated using a same layer of base material. As used herein, the phrase "microfabrication" refers to the process of fabricating miniature structures on micrometer scales and smaller. The major concepts and principles of microfabrication are microlithography, doping, thin films, etching, bonding, and polishing. As used herein, the phrase "thin films" refers to a layer of material ranging from fractions of a nanometer (monolayer) to several micrometers in thickness (e.g., between a few nanometers to about 100 μm). Thin films may be deposited by applying a very thin film of material (e.g., between a few nanometers to about 100 μm) onto a substrate surface to be coated, or onto a previously deposited layer of thin film. In various embodiments, a thin film connector is provided comprising a base polymer body (e.g., a supporting structure) and at least one conductive trace formed on the base polymer body. As used herein, the term "high density neural interface(s)" refers to a neural interface that comprises at least sixteen electrodes (i.e., recording, sensing, stimulating, other types of electrodes, or combinations thereof).

Neuromodulation devices such as deep brain and spinal cord stimulators electrically interface with neural tissue and treat various neurological conditions through electrical stimulation. As described herein, conventional neuromodulation devices use between four and sixteen electrodes and comprise a neurostimulator and lead assembly containing the electrodes. The neuromodulation devices with high density neural interfaces (i.e., at least sixteen electrodes), deep brain stimulation, cortical brain stimulation, spine stimulation, etc. often are limited in contact count by lead density, connector density/pitch/size, or complexity (e.g., having a lead split to multiple connectors). However, higher density arrays are desired due to the ability to more closely focus energy during therapy in order to increase clinical effectiveness, reduce side effects due to errant charge, and increase battery life by using charge more efficiently.

To address these limitations and problems, connectors of various embodiments disclosed herein enable connections with high density neural interfaces and are capable of being physically disconnected between the neurostimulator and the electrode assembly. One illustrative embodiment of the present disclosure is directed to a connector that includes a core and a supporting structure wrapped around at least a portion of the core. The connector may be located at a proximal end of a cable (e.g., a lead) of a lead assembly. The supporting structure comprises a first layer of dielectric material and a second layer of dielectric material. The first layer of dielectric material may be a high temperature liquid crystal polymer, and the second layer of dielectric material may be a low temperature liquid crystal polymer that is reflowed to attach the supporting structure to the core. Conductive traces are buried between the first layer of dielectric material and the second layer of dielectric material, and the conductive traces terminate at conductive contacts formed on a surface of the first layer of dielectric material. The connector has a predetermined shape or profile, which facilitates alignment and insertion of the connector into a header of a neurostimulator.

In other embodiments, a lead assembly is provided that comprises a cable comprising a proximal end, a distal end, and first conductive traces; and a connector comprising a core and a supporting structure wrapped around at least a portion of the core. The connector is located at the proximal end of the cable; the supporting structure comprises a first layer of dielectric material and a second layer of dielectric material; the first layer of dielectric material is a high temperature liquid crystal polymer; the second layer of dielectric material is a low temperature liquid crystal polymer that is reflowed to attach the supporting structure to the core; second conductive traces are buried between the first layer of dielectric material and the second layer of dielectric material; the second conductive traces terminate at conductive contacts formed on a surface of the first layer of dielectric material; and the connector has a predetermined shape or profile, which facilitates alignment and insertion of the connector into a header. The lead assembly further comprises an electrode assembly located at the distal end of the cable, the electrode assembly comprising electrodes electrically connected to the conductive contacts via the first conductive traces and the second conductive traces.

In other embodiments, a header and lead assembly is provided that comprises a connector comprising a core and a first supporting structure wrapped around at least a portion of the core. The first supporting structure comprises a first layer of dielectric material and a second layer of dielectric material; the first layer of dielectric material is a high temperature liquid crystal polymer; the second layer of dielectric material is a low temperature liquid crystal polymer that is reflowed to attach the first supporting structure to the core; first conductive traces are buried between the first layer of dielectric material and the second layer of dielectric material; the first conductive traces terminate at first conductive contacts formed on a surface of the first dielectric layer; and the connector has a first predetermined shape or profile. The header and lead assembly further comprises a header comprising a second supporting structure. The second supporting structure comprises one or more layers of polymer; second conductive traces are buried between the one or more layers of polymer, the second conductive traces terminate at second conductive contacts formed on a surface of the one or more layers of polymer; and the header has a second predetermined shape or profile structured to receive the first predetermined shape or profile of the connector. The header and lead assembly further comprises a clip structured to hold the first conductive contacts in electrical contact with the second conductive contacts.

In other embodiments, a lead assembly is provided that comprises a first cable comprising a proximal end and a distal end; a second cable comprising a proximal end and a distal end; and a connection assembly comprising: a first connector comprising a core and a first supporting structure wrapped around at least a portion of the core. The first connector is located at the proximal end of the first cable; the first supporting structure comprises a first layer of dielectric material and a second layer of dielectric material; the first layer of dielectric material is a high temperature liquid crystal polymer; the second layer of dielectric material is a low temperature liquid crystal polymer that is reflowed to attach the first supporting structure to the core; first conductive traces are buried between the first layer of dielectric material and the second layer of dielectric material; and the first conductive traces terminate at first conductive contacts formed on a surface of the first layer of dielectric material. The connection assembly further comprises a second connector comprising a second supporting structure. The second connector is located at the distal end of the second cable; the second supporting structure comprises a one or more layers of polymer; second conductive traces are buried between the one or more layers of polymer, and the second conductive traces terminate at second conductive contacts formed on a surface of the one or more layers of polymer. The connection assembly further comprises one or more attachment features that hold the first connector in physical contact with the second connector such that the first conductive contacts are in electrical contact with the second conductive contacts.

In other embodiments, a lead assembly is provided that comprises a high density cable comprising a proximal end and a distal end; a low density cable comprising a proximal end and a distal end; and a connector. The connector comprises a package comprising a housing, one or more multiplexor chips, distal feedthroughs connected to distal channel inputs of the one or more multiplexor chips, and proximal feedthroughs connected to proximal channel inputs of the one or more multiplexor chips; and a connection assembly comprising a supporting structure. The connector is located at the proximal end of the high density cable and the distal end of the low density cable; the supporting structure comprises a first layer of dielectric material and a second layer of dielectric material; the first layer of dielectric material is a low temperature liquid crystal polymer that is reflowed to attach the supporting structure to the package; the second layer of dielectric material is a high temperature liquid crystal polymer; distal conductive traces are buried between the first layer of dielectric material and the second layer of dielectric material; proximal conductive traces are buried between the first layer of dielectric material and the second layer of dielectric material; the distal conductive traces connected to the high density cable, and the distal conductive traces terminate at distal conductive contacts formed on a surface of the second layer of dielectric material; the proximal conductive traces connected to the low density cable, and the proximal conductive traces terminate at proximal conductive contacts formed on the surface of the second layer of dielectric material; the distal conductive contacts are electrically connected to the distal feedthroughs; and the proximal conductive contacts are electrically connected to the proximal feedthroughs.

Advantageously, these approaches provide a connector, which has increased contact points, a smaller footprint, and greater design flexibility. More specifically, these approaches enable connectors with reliable, non-permanent connections between a lead assembly and a neurostimulator. This solution is scalable to connecting many electrodes (e.g., greater than sixteen) using a multiplexer chip, and thus enabling several therapeutic opportunities for neurostimulation. Furthermore even for applications where multiple electrodes are not required, various embodiments can be miniaturized to make the implant minimally invasive, additionally may make invasive anatomies to become accessible (or navigable) due to the miniaturization. It should be understood that although deep brain neurostimulation and vagus nerve or artery/nerve plexus device applications are provided as examples of some embodiments, this solution is applicable to all leads and devices that need electrodes/sensors that need to be attached to a neurostimulator.

II. Neuromodulation Devices and Systems with a Lead Assembly

FIG. 1 shows a neuromodulation system 100 in accordance with some aspects of the present invention. In various embodiments, the neuromodulation system 100 includes an implantable neurostimulator 105 and a lead assembly 110. The implantable neurostimulator 105 (e.g., an implantable pulse generator (IPG)) may include a housing 115, a feedthrough assembly or header 120, a power source 125, an antenna 130, and an electronics module 135 (e.g., a computing system). The housing 115 may be comprised of materials that are biocompatible such as bioceramics or bioglasses for radio frequency transparency, or metals such as titanium. In accordance with some aspects of the present invention, the size and shape of the housing 115 may be selected such that the neurostimulator 105 can be implanted within a patient. In the example shown in FIG. 1, the feedthrough assembly or header 120 is attached to a hole 137 in a surface of the housing 115 such that the housing 115 is hermetically sealed. The feedthrough assembly or header 120 may include one or more contacts 140 (i.e., electrically conductive elements, pins, wires, tabs, pads, etc.) mounted within the housing 115 or a cap extending from an interior to an exterior of the housing 115. The one or more contacts 140 are arranged to match and make electrical contact with one or more contacts of a connector of the lead assembly 110. In various embodiments, the contacts 140 may be made with a hemisphere on contact (point contact) or with a cylinder on contact (line contact). In some embodiments, the contacts 140 are spring-loaded normal to the outer contact surfaces of the contacts of the connector. The power source 125 may be within the housing 11S and connected (e.g., electrically connected) to the electronics module 135 to power and operate the components of the electronics module 135. The antenna 130 may be connected (e.g., electrically connected) to the electronics module 135 for wireless communication with external devices via, for example, radiofrequency (RF) telemetry.

In some embodiments, the electronics module 135 may be connected (e.g., electrically connected) to interior ends of the feedthrough assembly 120 such that the electronics module 135 is able to apply a signal or electrical current to conductive traces of the lead assembly 110 connected to the feedthrough assembly 120. The electronics module 135 may include discrete and/or integrated electronic circuit components that implement analog and/or digital circuits capable of producing the functions attributed to the neuromodulation devices or systems such as applying or delivering neural stimulation to a patient. In various embodiments, the electronics module 135 may include software and/or electronic circuit components such as a pulse generator 142 that generates a signal to deliver a voltage, current, optical, or ultrasonic stimulation to a nerve or artery/nerve plexus via electrodes, a controller 145 that determines or senses electrical activity and physiological responses via the electrodes and sensors, controls stimulation parameters of the pulse generator 140 (e.g., control stimulation parameters based on feedback from the physiological responses), and/or causes delivery of the stimulation via the pulse generator 140 and electrodes, and a memory 150 with program instructions operable on by the pulse generator 140 and the controller 145 to perform one or more processes for applying or delivering neural stimulation.

In various embodiments, the lead assembly 110 includes one or more cables or lead bodies 155, one or more electrode assemblies 160 having one or more electrodes 165 (optionally one or more sensors), and one or more connectors 170, 170', 170". In some embodiments, the lead assembly 110 is a monolithic structure. In various embodiments, the one or more connectors 170, 170', 170" include a main body having a supporting structure and one or more of conductive traces formed on the supporting structure. The supporting structure may be comprised of one or more layers of dielectric material. Each trace from the one or more conductive traces terminates at a bond pad 175, 175', 175" exposed on a surface of the supporting structure. In some embodiments, the connector 170 is located at a proximal end of the lead assembly 110 and used to connect the lead assembly 110 with the neurostimulator 105. In other embodiments, one or more connectors 170' are located at the proximal end and/or distal end of one or more lead bodies 155 and used to connect the one or more lead bodies 155 thereby extending an overall length of the lead assembly. In yet other embodiments, a connector 170" is located at the proximal end or distal end of one or more lead bodies 155 and used to connect a multiplexer chip 180 to the lead assembly 110.

The one or more cables 155 may include one or more conductive traces 182 formed on a supporting structure 185. The one or more conductive traces 180 allow for electrical coupling of the electronics module 135 to the electrodes 165 and/or sensors of the electrode assemblies 160 via the one or more connectors 170. In some embodiments, the one or more of conductive traces 182 and supporting structure 185 are the same conductive traces and supporting structure as the one or more conductive traces and supporting structure (monolithic) of the one or more connectors 170. In other embodiments, the one or more of conductive traces 182 and supporting structure 185 are different conductive traces and supporting structure from the one or more conductive traces and supporting structure (different structures but electrically connected) of the one or more connectors 170, 170', 170". As described herein in detail, the supporting structures may be formed with a dielectric material such as a polymer having suitable dielectric, flexibility and biocompatibility characteristics. Polyurethane, polycarbonate, silicone, polyethylene, fluoropolymer and/or other medical polymers, copolymers and combinations or blends may be used. The conductive material for the traces may be any suitable conductor such as stainless steel, silver, copper or other conductive materials, which may have separate coatings or sheathing for anticorrosive, insulative and/or protective reasons.

The electrode assemblies 160 may include the electrodes 165 and/or sensors fabricated using various shapes and patterns to create certain types of electrode assemblies (e.g., book electrodes, split cuff electrodes, spiral cuff electrodes, epidural electrodes, helical electrodes, probe electrodes, linear electrodes, neural probe, paddle electrodes, intraneural electrodes, etc.). In various embodiments, the electrode assemblies 160 include a base material that provides support for microelectronic structures including the electrodes 165, a wiring layer, optional contacts, etc. In some embodiments, the base material is the supporting structure 185. The wiring layer may be embedded within or located on a surface of the supporting structure 185. The wiring layer may be used to electrically connect the electrodes 165 with the one or more conductive traces 180 directly or indirectly via a lead conductor. The term "directly", as used herein, may be defined as being without something in between. The term "indirectly", as used herein, may be defined as having something in between. In some embodiments, the electrodes 165 may make electrical contact with the wiring layer by using the contacts.

III. Multi-Sector Connectors and Methods of Manufacture

Figure 2A:
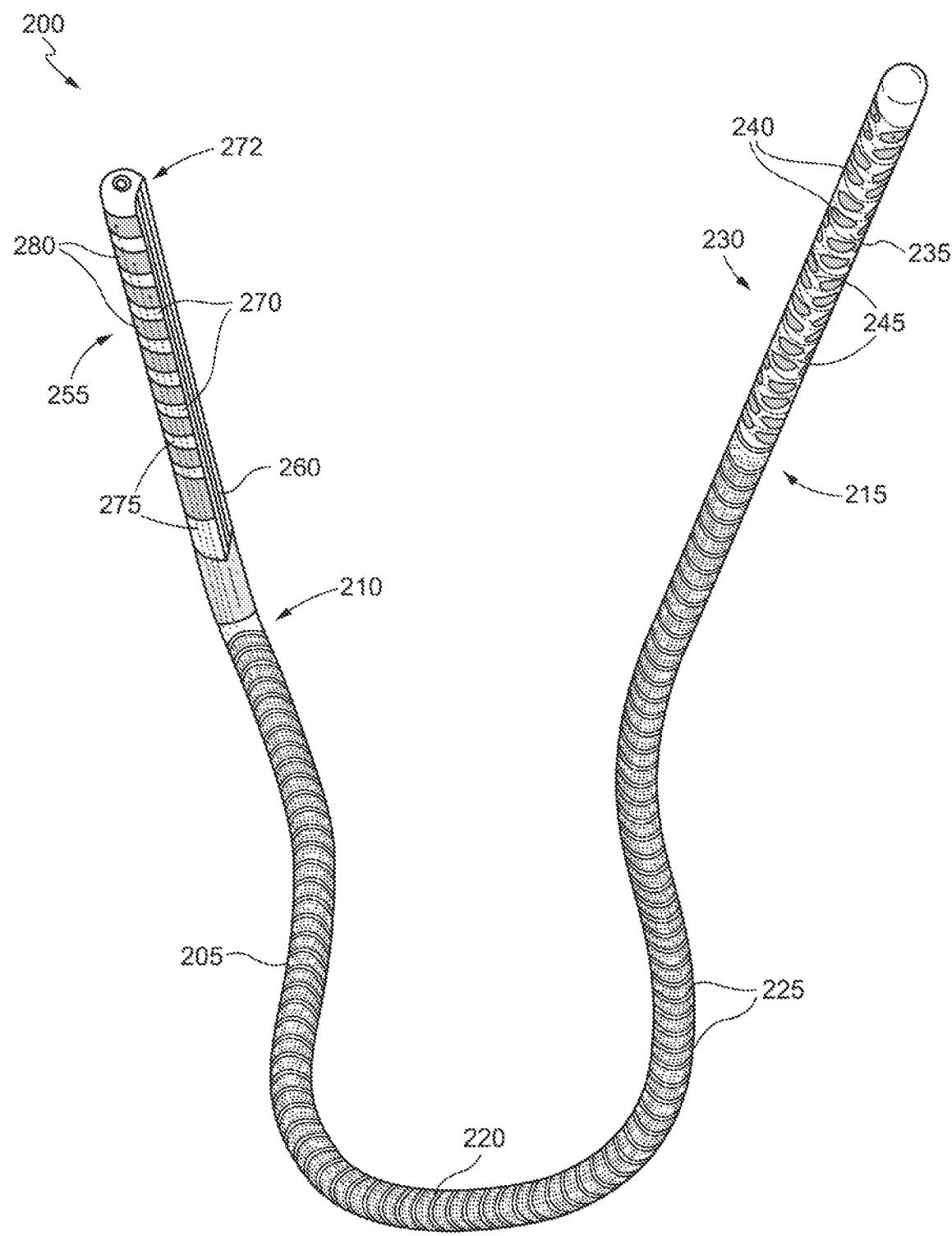
FIGS. 2A and 2B show a lead assembly in accordance with various embodiments.
Figure 2B:
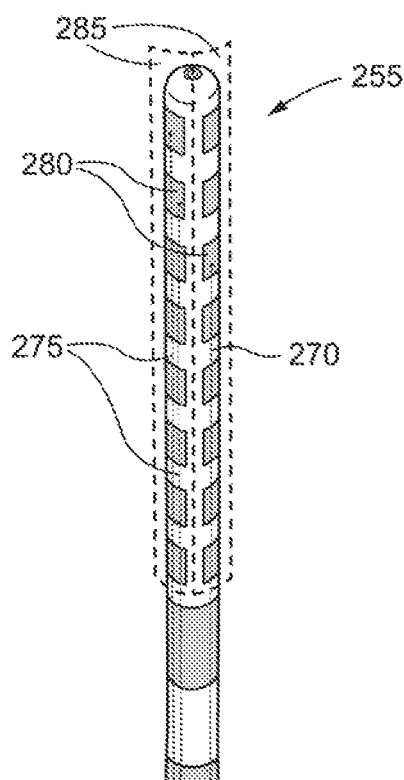

FIGS. 2A and 2B show a lead assembly 200 (e.g., the lead assembly 110 described with respect to FIG. 1) in accordance with aspects of the present disclosure. In various embodiments, the lead assembly 200 comprises a cable 205 having a proximal end 210 and a distal end 215. The cable 205 may comprise a supporting structure 220 and a plurality of conductive traces 225 formed on a portion of the supporting structure 220. As used herein, the term "formed on" refers to a structure or feature that is formed on a surface of another structure or feature, a structure or feature that is formed within another structure or feature, or a structure or feature that is formed both on and within another structure or feature. In some embodiments, the supporting structure 220 extends from the proximal end 210 to the distal end 215. In some embodiments, the supporting structure 220 may be made of one or more layers of dielectric material (i.e., an insulator). The dielectric material may be selected from the group of electrically flexible nonconductive materials consisting of organic or inorganic polymers, polyimide-epoxy, epoxy-fiberglass, and the like. In certain embodiments, the dielectric material is a polymer of imide monomers (i.e., a polyimide), a liquid crystal polymer (LCP) such as KevlarQ®, parylene, polyether ether ketone (PEEK), or combinations thereof. In other embodiments, the supporting structure 220 may be made of one or more layers of dielectric material formed on a substrate. The substrate may be made from any type of metallic or non-metallic material.

In various embodiments, the one or more conductive traces 225 are a plurality of traces, for example, two or more conductive traces or from two to twenty-four conductive traces. The plurality of conductive traces 225 are comprised of one or more layers of conductive material. The conductive material selected for the one or more conductive traces 225 should have good electrical conductivity and may include pure metals, metal alloys, combinations of metals and dielectrics, and the like. For example, the conductive material may be platinum (Pt), platinum/iridium (Pt/Ir), titanium (Ti), gold/titanium (Au/Ti), or any alloy thereof. In some embodiments, it is also desirable that the conductive material selected for the one or more conductive traces 225 have thermal expansion characteristics or a coefficient of thermal expansion (CTE) that is approximately equal to that of CTE of the supporting structure 220. Matching the CTE of components that contact one another is desirable because it eliminates the development of thermal stresses, which may occur during fabrication and the operation of the cable, and thus eliminates a known cause of mechanical failure in the components. As used herein, the terms "substantially," "approximately" and "about" are defined as being largely but not necessarily wholly what is specified (and include wholly what is specified) as understood by one of ordinary skill in the art. In any disclosed embodiment, the term "substantially," "approximately," or "about" may be substituted with "within [a percentage] of" what is specified, where the percentage includes 0.1, 1, 5, and 10 percent.

As shown in FIG. 2A, the lead assembly 200 may further comprise an electrode assembly 230 formed on a supporting structure 235. The supporting structure 235 may provide support for microelectronic structures including one or more electrodes 240, a wiring layer 245, and optional contact(s) (not shown). The electrode assembly 230 may be located at the distal end 215 of the lead assembly 200. The one or more electrodes 240 are in electrical connection with one or more conductive traces of the plurality of conductive traces 225, for example, via the wiring layer 245 and optionally the contact(s). In various embodiments, the supporting structure 220 of at least one cable 205 and the supporting structure 235 of the electrode assembly 230 are the same structure (i.e., the supporting structure is continuous), which thus creates a monolithic cable. In alternative embodiments, the supporting structure 220 of at least one cable 205 and the supporting structure 235 of the electrode assembly 230 are different structures but are connected such that there is an electrical connection between the plurality of conductive traces 225, wiring layer 245, and the one or more electrodes 240.

As shown in FIG. 2A, the lead assembly 200 may further comprise a connector 255 formed of a core 260 and an inlaid supporting structure 270 with a predetermined shape or profile 272. In some embodiments, the core 260 is comprised of one or more layers of material such as polyimide, liquid crystal polymer, parylene, polyether ether ketone, polyurethane, metal, or a combination thereof. In certain embodiments, the one or more layers of material of the core 260 are a TPU. The core 260 may be formed by molding or extrusion with high melting temperature TPU (e.g. Lubrizol Pellethane® 2363-75D, 205C). In some embodiments, the supporting structure 270 is comprised of one or more layers of dielectric material (i.e., an insulator). The layers of dielectric material of the supporting structure 270 may be formed in a FPCB process with metallization layers (e.g., vias or wiring layers) for interconnection. In other embodiments, the supporting structure 270 is made of one or more layers of dielectric material and a coating of a thin layer of a polymer such as TPU. The dielectric material of the supporting structure 270 may be selected from the group of electrically flexible nonconductive materials consisting of organic or inorganic polymers, polyimide-epoxy, epoxy-fiberglass, and the like. In certain embodiments, the dielectric material is a polymer of imide monomers (i.e., a polyimide), a liquid crystal polymer (LCP) such as Kevlar®, parylene, polyether ether ketone (PEEK), or combinations thereof.

In some embodiments, one or more conductive traces 275 and one or more contacts 280 (i.e., electrically conductive elements, pins, wires, tabs, pads, etc.) are formed on the supporting structure 270. The conductive traces 275 and contacts 280 may be comprised of one or more layers of conductive material for electrical conductivity. The conductive material selected for the conductive traces 275 and contacts 280 should have good electrical conductivity and may include pure metals, metal alloys, combinations of metals and dielectrics, and the like. For example, the conductive material may be platinum (Pt), platinum/iridium (Pt/Ir), titanium (Ti), gold/titanium (Au/Ti), or any alloy thereof. In some embodiments, it is also desirable that the conductive material selected for the conductive traces 275 and contacts 280 have a CTE that is approximately equal to that of a CTE of the supporting structure 270. In some embodiments, the supporting structure 220 of the cable 205 and the supporting structure 270 of the connector 255 are the same structure (i.e., the supporting structure is continuous), which thus creates a monolithic cable. In alternative embodiments, the supporting structure 220 of the cable 205 and the supporting structure 270 of the connector 255 are different structures but are connected such that there is an electrical connection between the plurality of conductive traces 225, wiring layer 245, the one or more electrodes 240, the one or more conductive traces 275, and the contacts 280.

In various embodiments, the connector 255 may further comprise multiple sectors 285 (e.g., faces of the connector) extending along the outer surface of the supporting structure 270, and one or more contacts 280 are arranged in each sector of the multiple sectors 285 (see, e.g., FIG. 2B). In some embodiments, the one or more conductive traces 275 are a plurality of traces, for example, two or more conductive traces or from two to twenty-four conductive traces. In some embodiments, the one or more contacts 280 are a plurality of contacts, for example, two or more conductive traces or from two to twenty-four contacts. In some embodiments, at least one trace of the conductive traces 275 terminates at a contact 280 exposed on the outside surface the supporting structure 270 within a sector 285. In alternative embodiments, each trace from the one or more conductive traces 275 terminates at a contact 280 exposed on the outside surface the supporting structure 270 within a sector 285. As should be understood, in some embodiments, each electrode from the one or more electrodes 240 is electrically connected via a corresponding wiring layer 245, optional contact, conductive trace 225, and conductive trace 275, to a respective contact 280. In other words, each electrode may be electrically connected to a different contact (a one to one relationship). In alternative embodiments, a multiplexer chip may be used such that one or more electrodes from the one or more electrodes 240 is electrically connected via wiring layer 245, optional contact, a conductive trace 225, and conductive trace 275, to a single contact 280. In other words, each electrode may be electrically connected to a same or different contact (a many to one relationship).

The one or more conductive traces 275 may be deposited onto a layer of the supporting structure 270 in a sector 285 by using thin film deposition techniques well known to those skilled in the art such as by sputter deposition, chemical vapor deposition, metal organic chemical vapor deposition, electroplating, electroless plating, and the like. In some embodiments, the thickness of the one or more conductive traces 275 is dependent on the particular impedance desired for conductor, in order to ensure excellent signal integrity (e.g., electrical signal integrity for stimulation or recording). For example, if a conductor having a relatively high impedance is desired, a small thickness of conductive material should be deposited onto a layer of the supporting structure 270. If, however, a signal plane having a relatively low impedance is desired, a greater thickness of electrically conductive material should be deposited onto a layer of the supporting structure 270. In certain embodiments, each of the one or more conductive traces 275 has a thickness (t). In some embodiments, the thickness (t) is from 0.5 μm to 25

µm or from 5 µm to 10 µm, for example about 5 µm or about 8 µm. In some embodiments, each of the one or more conductive traces 275 has a length (l) of about 1 mm to 100 mm or 1 cm to 3 cm, e.g., about 15 mm. In some embodiments, each of the one or more conductive traces 275 has a width (w) from 2.0 µm to 500 µm, for example about 30 µm or about 50 µm.

As shown in FIGS. 3A-3F, the connector 300 (e.g., the connector 255 as discussed with respect to FIG. 2) may be formed of a core 305 and an inlaid supporting structure 310 at the proximal end 315 of a cable 320 with a predetermined shape or profile 325. The predetermined shape or profile 325 acts essentially as a key to assist with alignment in insertion of the connector 300 into a header of the neurostimulator. The header includes a predetermined shape or profile (not shown) to match the predetermined shape or profile 325, which facilitates alignment and insertion of the connector 300 into the header. In some embodiments, the predetermined shape or profile 325 includes an indexing feature 330 that ensures the connector 300 is inserted into the header in a correct manner such that the contacts 335 of the connector 300 match with preselected contacts of the header. As should be understood, the use of an index assures the ultimate connection of each electrode to a specific input port of the electronic module of the neurostimulator such that the controller is guaranteed which electrode it is either activating for stimulation or receiving a signal from during recording.

Figure 3A:
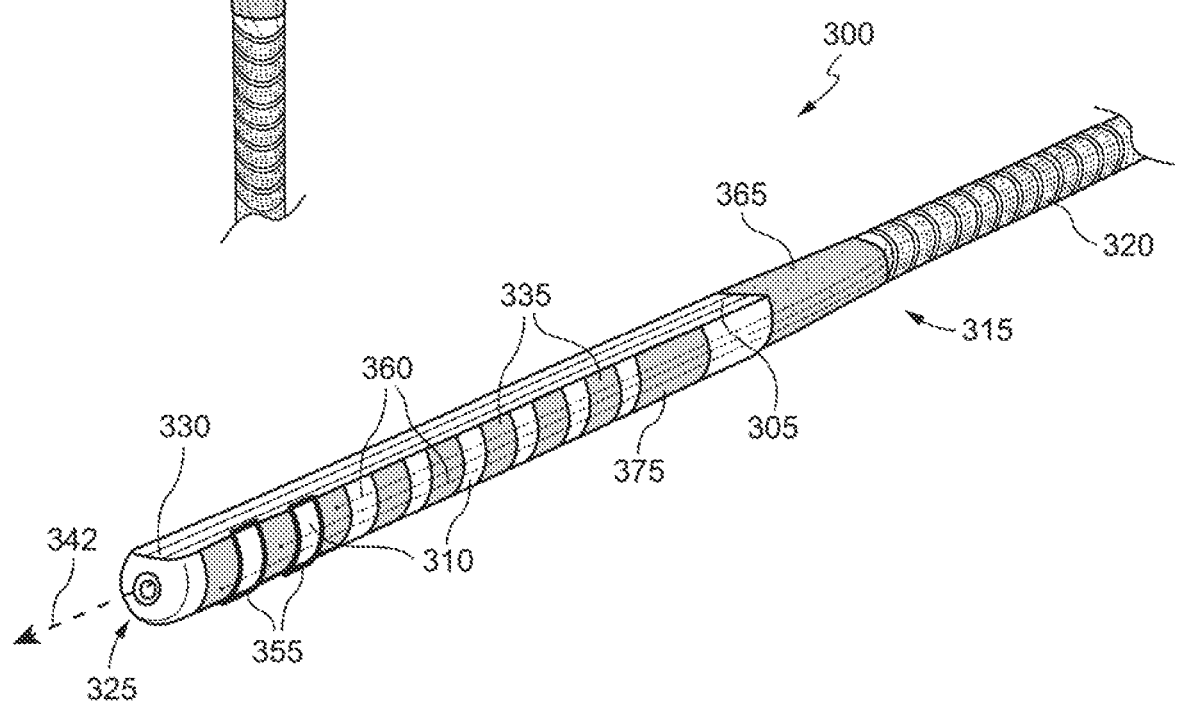
FIGS. 3A-3H show multi-sector connectors in accordance with various embodiments.
Figure 3B:
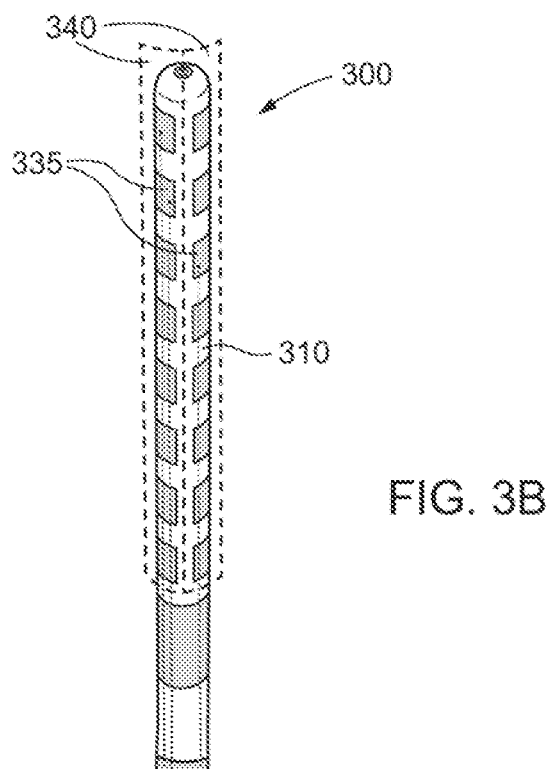
Figure 3C:
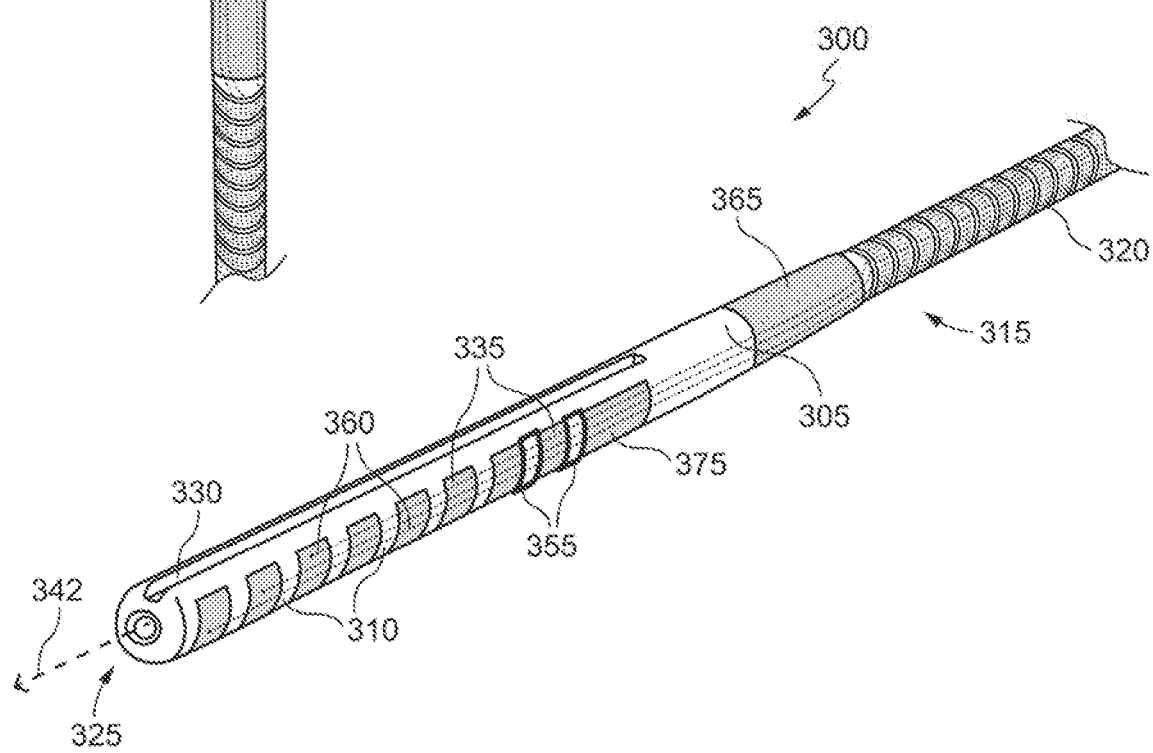
Figure 3D:
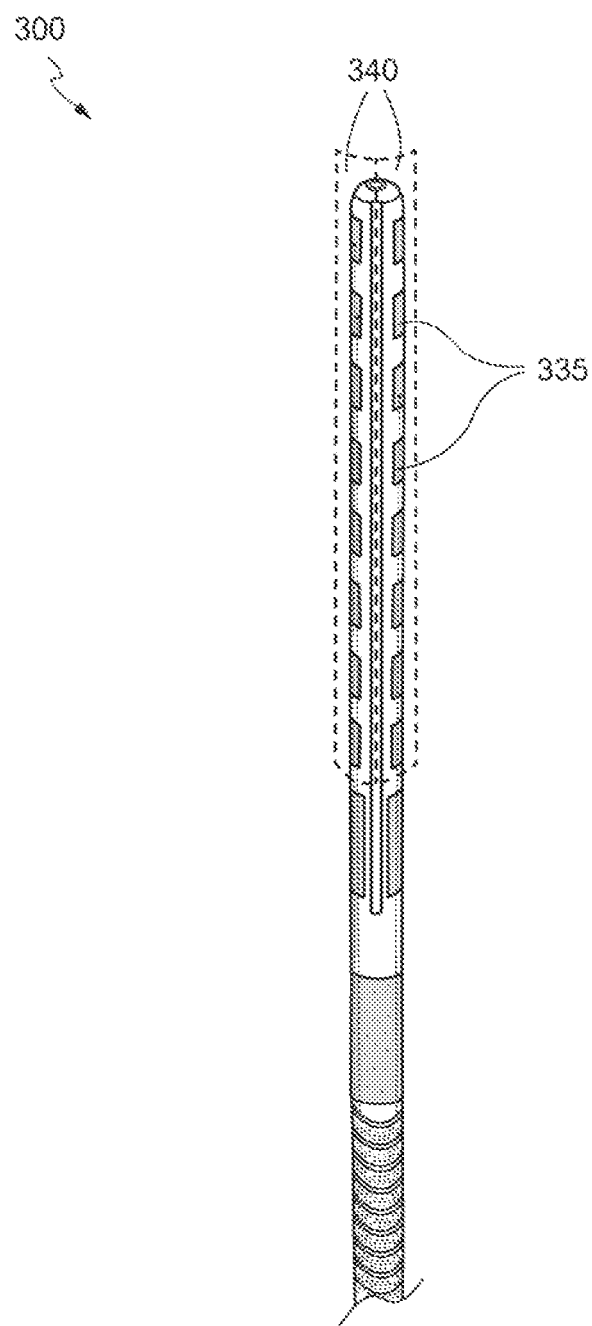
Figure 3E:
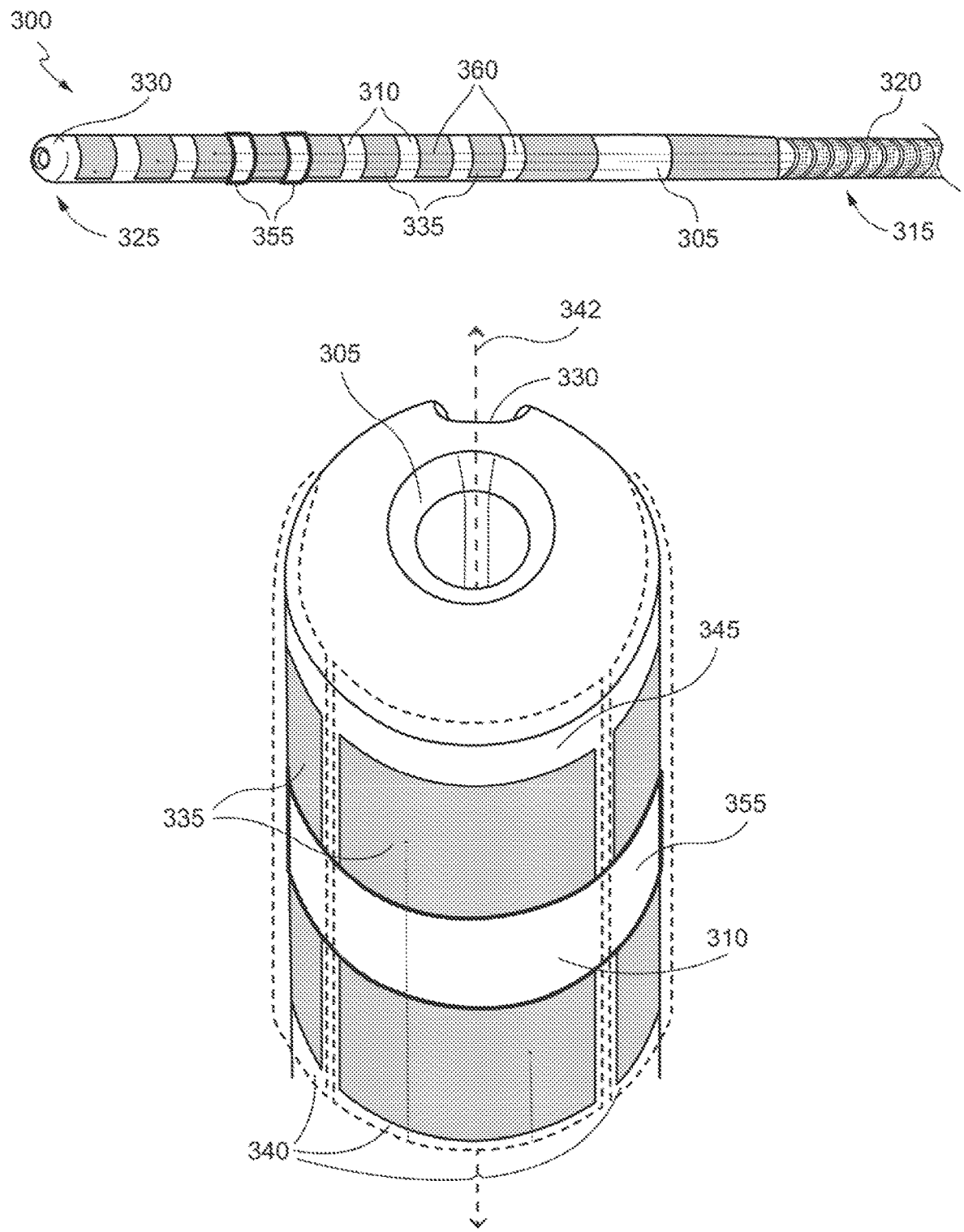

FIGS. 3A and 3B shows the connector 300 has a "D"-shaped profile 325, which includes the contacts 335 arranged as split rings on the surface of the supporting structure 310 in the curved portion of the "D"-shaped profile, and the flat portion of the "D"-shaped profile is an indexing feature 330 for keying during insertion of the connector 300 into a header. In some embodiments, the curved portion of the "D"-shaped profile comprises multiple (e.g., dual) sectors 340 of contacts 335. FIGS. 3C, 3D, and 3E show the connector 300 has a notched profile, which includes the contacts 335 arranged as split rings on the surface of the supporting structure 310 in the curved portion of the notched profile, and a notch of the notched profile is an indexing feature 330 for keying during insertion of the connector 300 into a header. The notched profile may increase accuracy of the keying and increases a surface area of the connector 300 for additional sectors 340 of contacts 335 (and may limit overlap in tolerancing of rotational control). In various embodiments, the contacts 335 are formed from split annular rings of conductive material positioned around an axis 342 of the connector 300 and exposed on the surface 345 of the supporting structure 310. Each split annular ring may be spaced apart from one another on the surface 345 of the supporting structure 310 by a region 355 of a top layer of the dielectric material. A width or pitch (p) of the region 355 of the top layer of the dielectric material that separates each split annular ring may be between 0.1 mm to 10 mm, for example about 2.0 mm. In some embodiments, each portion of the split annular ring connects to a single trace from the conductive traces 360. In other embodiments, each portion of the split annular ring connects to two or more traces from the conductive traces 360. For example, a first portion (e.g., a left side portion) of the split annular ring in a sector 340(A) may be connected with a first trace and a second portion (e.g., a right side portion) of the split annular ring in a sector 340(B) may be connected with a second trace. Alternatively, a multiplexer chip may be used to drive signals and thus the portions of the split annular ring may be connected to multiple traces from the conductive traces 360. In various embodiments, eight split annular rings are positioned around the axis 342 of connector 30 and exposed on the surface 345; however, it should be understood that more or less than eight split annular rings can be positioned on the supporting structure 310. For example, the supporting structure may have an increased surface area to accommodate more annular rings or contacts 335 and enhance design flexibility for the connector 300. Additionally, the annular ring may have two splits (to isolate two contact regions); however, it should be understood that more or less than two splits can be used. For example, the annular rings may have an increased number of splits (3, 4, 5, 6, etc.) to enhance design flexibility for the connector 300.

Figure 3F:
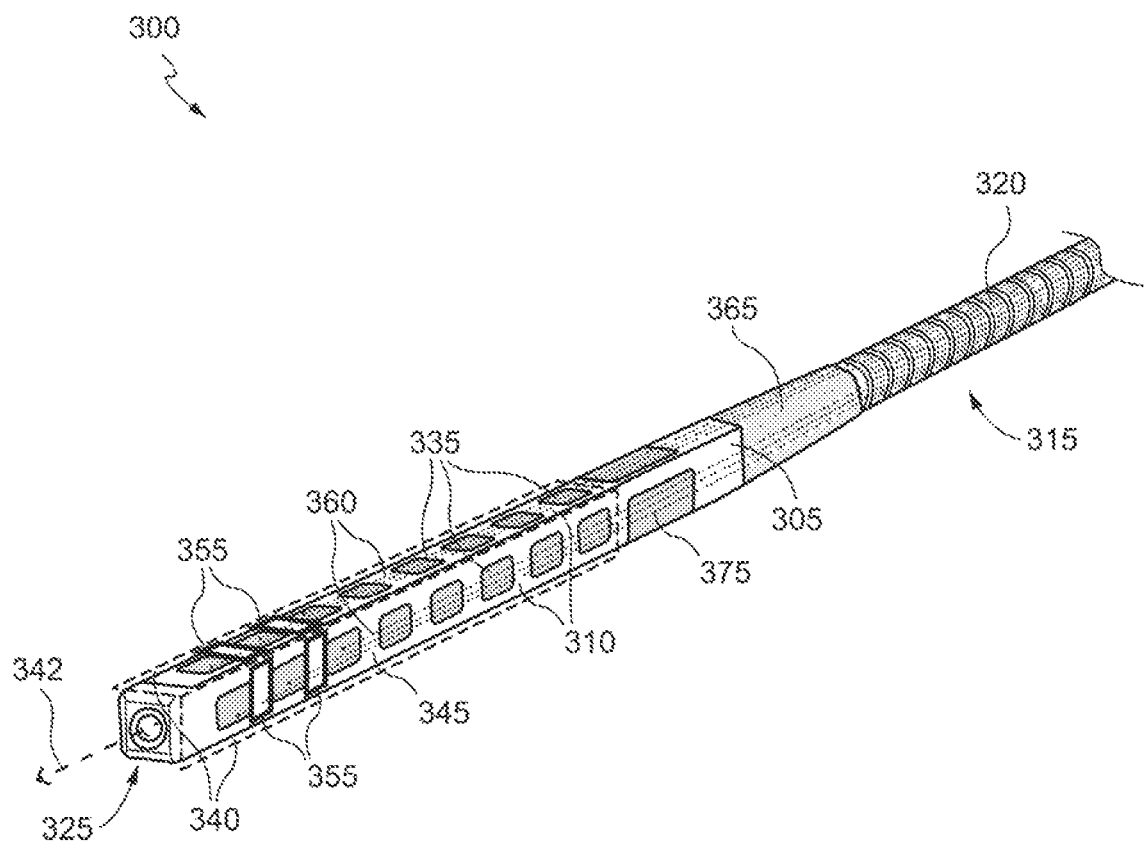
Figure 3G:
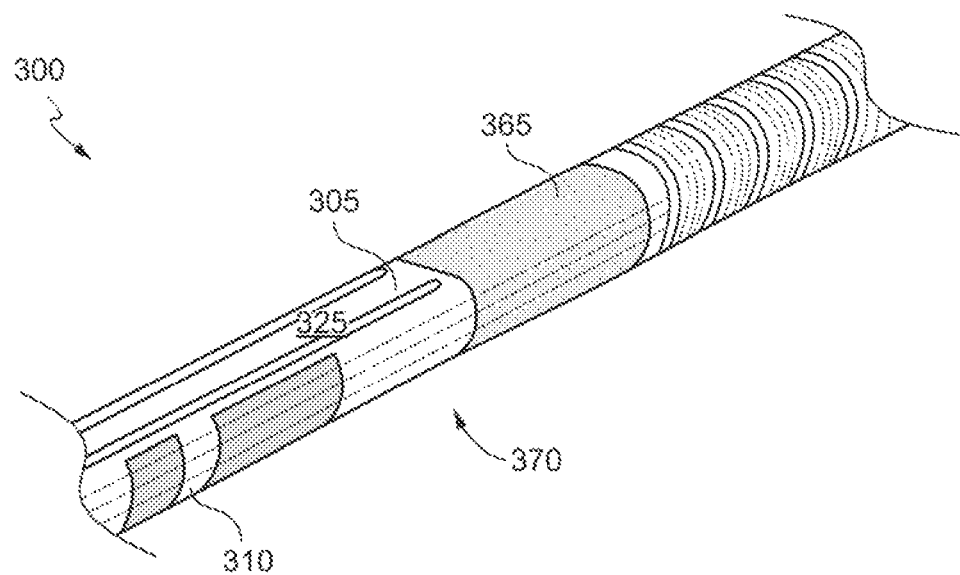
Figure 3H:
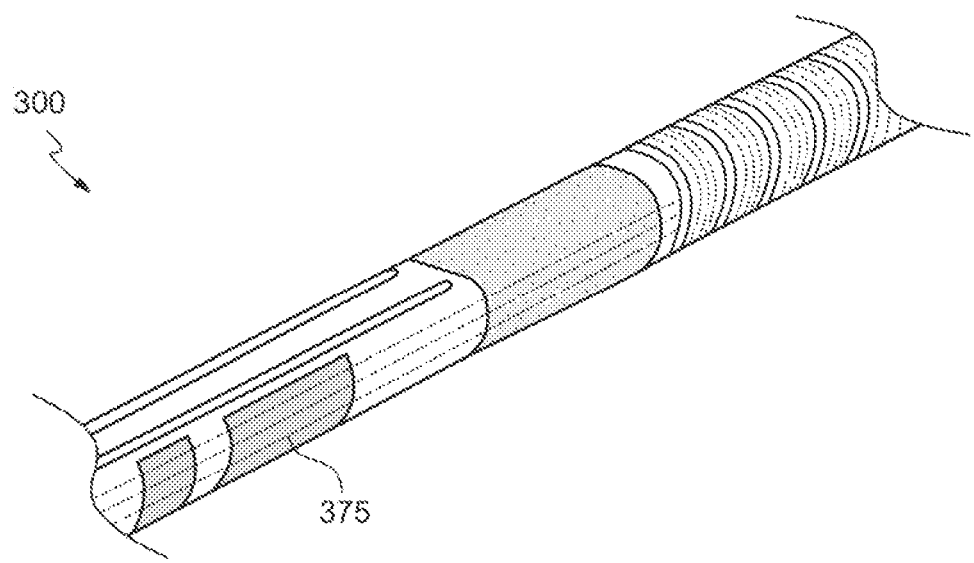

FIG. 3F shows the connector 300 has a square shaped profile 325 having quadruple planar sectors 340 of contacts 335. A used herein "planar" means relating to or in the form of a plane. In this embodiments, the four sides of contacts 335 provides for accurate alignment and high density contacts. However, while the connector 300 is keyed to the square sides, there is no indexing of the four sides of the connector 300. The absence of the indexing feature may increase usability by health care providers who can insert the connector in any orientation. The orientation may be determined empirically by software of the controller and will adapt to any of the four possible orientations. In certain embodiments, extra contacts 335 could be added with impedance, resistive, or ohmic fiducials to provide orientation queues to the controller of the neurostimulator. In various embodiments, the contacts 335 are formed from separate pads of conductive material positioned around the axis 342 of the connector 300 and exposed on the surface 345 of the supporting structure 310. Each pad may be spaced apart from one another on the surface 345 of the supporting structure 310 by a region 355 of a top layer of the dielectric material. A width or pitch (p) of the region 355 of the top layer of the dielectric material that separates each pad may be between 0.1 mm to 10 mm, for example about 2.0 mm. In some embodiments, each pad connects to a single trace from the conductive traces 360. In other embodiments, each pad connects to two or more traces from the conductive traces 360. For example, a first pad in a sector 340(A) may be connected with a first trace and a second pad in a sector 340(B) may be connected with a second trace. Alternatively, a multiplexer chip may be used to drive signals and thus pads may be connected to multiple traces from the conductive traces 360. In various embodiments, eight pads are positioned in each sector 340 around the axis 342 of connector 300 and exposed on the surface 345; however, it should be understood that more or less than eight pads can be positioned on the supporting structure 310 in each sector 340. For example, the supporting structure 310 may have an increased surface area to accommodate more pads or contacts 335 and enhance design flexibility for the connector 300.

As shown in FIGS. 3A-3G, the connector 300 (e.g., the connector 255 as discussed with respect to FIG. 2) may further comprise a scaling feature 365. In various embodiments, the sealing feature 365 is a section of the profile 325 at the distal end 370 of the connector 300. In some embodiments, the sealing feature 365 includes the core 305 and/or the inlaid supporting structure 310 having a different material, texture, or stiffness such that the sealing feature 365 is structurally configured to engage with a scaling surface of the header of the neurostimulator. In other embodiments, the scaling feature 365 includes an additional layer of material over and/or within the core 305 and/or the inlaid supporting structure 310 (e.g., a polymer material) that is of a different material, texture, or stiffness from that of the core 305 and/or the inlaid supporting structure 310. As shown in FIGS. 3A-3H, the connector 300 may further comprise a retention feature 375 proximal to the sealing feature 365 for mechanical retention or connection with a corresponding feature in the header to retain insertion of the connector 300 in the header and maintain a seal between the sealing feature 365 and sealing surface of the header. In some embodiments, the retention feature 375 is an annular ring of material such as metal or polymer formed on the supporting structure, and the corresponding feature of the header is a set screw or engagement hook.

Figure 4C:
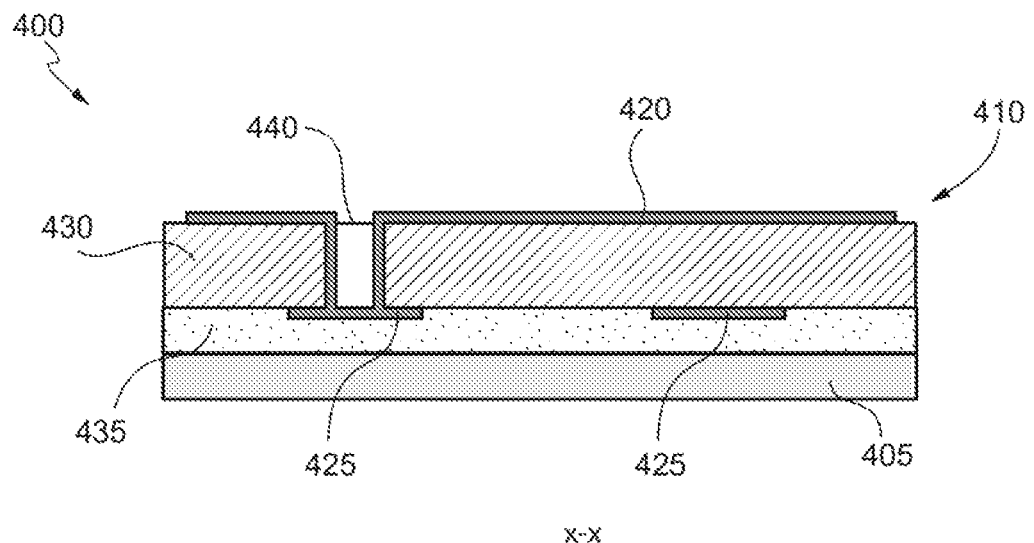

As shown in FIGS. 4A (frontside) and 4B (backside), the connector 400 (e.g., the connector 255 as discussed with respect to FIG. 2) may be formed of a core 405 and an inlaid supporting structure 410 with a predetermined layout 415 of contacts 420 and conductive traces 425. As shown in FIG. 4C (cross-section of the connector 400 along X-X from FIGS. 4A and 4B), the supporting structure 410 may comprise a first layer of dielectric material 430 and a second layer of dielectric material 435 with the conductive traces 425 buried between the first layer of dielectric material 430 and the second layer of dielectric material 435. In some embodiments, the first layer of dielectric material 430 comprises at least one contact via 440 for each contact 420. The contact via 440 may comprise a conductive material for electrically connecting each contact 420 to at least one trace of the conductive traces 425 such that each trace of the conductive traces 425 terminates at a contact 420. The contact via 440 may be connected to the at least one trace of the conductive traces 425 directly or indirectly by way of a wiring layer (not shown). In some embodiments, the conductive material is lined on at least a portion of the walls of the via hole. In other embodiments, the conductive material fills the via hole.

Figure 4D:
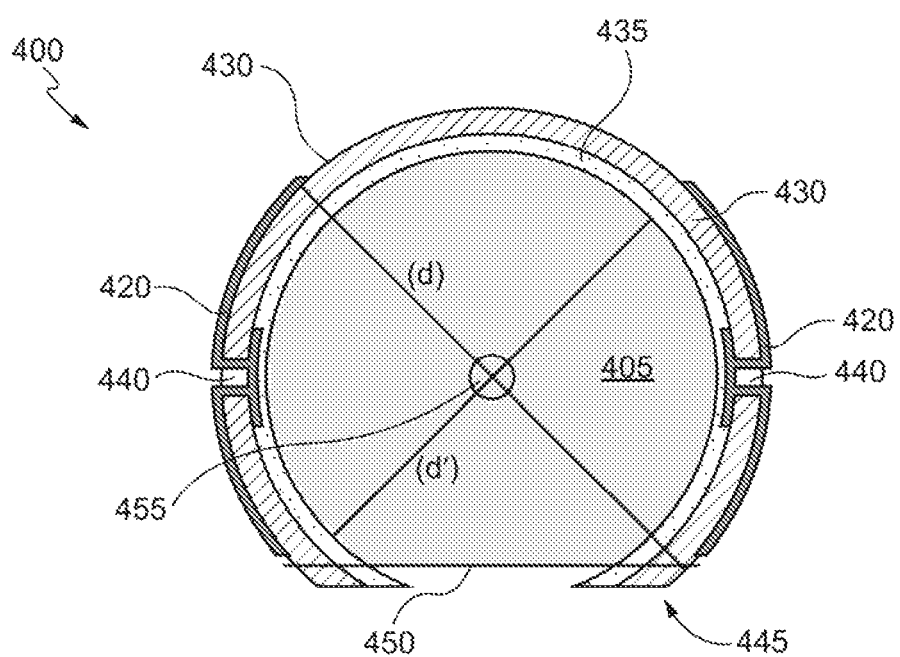

In various embodiments, the connector 400 may be formed with a predetermined shape or profile 445 (e.g., a "D"-shaped profile as shown in FIG. 4D). The predetermined shape or profile 445 acts essentially as a key to assist with alignment in insertion of the connector 400 into a header of the neurostimulator. In some embodiments, the predetermined shape or profile 445 includes an indexing feature 450 that ensures the connector 400 is inserted into the header in a correct manner such that the contacts 420 of the connector 400 match with preselected contacts of the header. As shown in FIG. 4D, the predetermined shape or profile 445 comprises the one or more layers of dielectric material 430/435 at least partially wrapped around the core 405. The first layer of dielectric material 430 may define an outer diameter (d) of the predetermined shape or profile 445 and the second layer of dielectric material 435 may define an inner diameter (d') of the predetermined shape or profile 445. The core 405 may at least partially fill the interior of predetermined shape or profile 445 defined by the inner diameter (d'). The core 405 may be comprised of one or more layers of material such that the core 405 has a Shore durometer of greater than 70D. In some embodiments, the one or more layers of material of the core 405 are polyimide, liquid crystal polymer, parylene, polyether ether ketone, polyurethane, metal, or a combination thereof. In certain embodiments, the one or more layers of material of the core 405 is a TPU. Although the connector 400 is shown in FIG. 4D and described with respect to a "D"-shaped profile, it should be understood that other shapes for the connector have been contemplated, for example, spherical cubed, torus, ellipsoid, etc.

Once the core 405 and the supporting structure 410 are shaped, the core 405 and the supporting structure 410 may then be baked to thermoform the core 405 and supporting structure 410 into a final shape, for example a column with a "D"-shaped profile, as shown in FIG. 4D. The core 405 and the supporting structure 410 may be reflowed at 130° C.-150° C. (e.g., 137° C.) using the second layer of dielectric material 435 as an adhesive to attach the core 405 to the supporting structure 410. In some embodiments, the first layer of dielectric material 430 is a first type of polymer material, e.g., a high temperature liquid crystal polymer, that acts as an overlay for insulation, and the second layer of dielectric material 435 is a second type of polymer material, e.g., a low temperature liquid crystal polymer, that acts as an adhesive for bonding the supporting structure 410 to the core 405, as shown in FIGS. 4C and 4D. As used herein, "a high temperature liquid crystal polymer" refers to a liquid crystal polymer with a high melting temperature of greater than 300° C. As used herein, "a low temperature liquid crystal polymer" refers to a liquid crystal polymer with a low melting temperature of less than 300° C.

As shown in FIGS. 4A, 4B, and 4D, in some embodiments, the contacts 420 may be split annular rings positioned around an axis 455 of the predetermined shape or profile 445 and exposed on the surface 460 of the predetermined shape or profile 445. For example, the contacts 420 may be raised above a surface of the supporting structure 410 (e.g., a top surface of the contacts 420 protrudes above a top surface of the supporting structure 410) and comprise an anti-abrasive finish. In some embodiments, the contacts 420 are raised above a surface of the supporting structure 410 by a predetermined distance. In certain embodiments, the predetermined distance is from 0.05 mm to 1.0 mm, for example about 0.5 mm. Each split annular ring may be spaced apart from one another on the surface 460 of the cylindrical tube 445 by a region 465 of the first layer of the dielectric material 430. A width or pitch (p) of the region 465 of the first layer of the dielectric material 550 that separates each split annular ring may be between 1.0 mm to 10 mm, for example about 2 mm. In some embodiments, each contact 420 of a split annular ring connects to a single trace of the conductive traces 425. In other embodiments, each contact 420 of a split annular ring connects to two or more traces from the conductive traces 420. For example, a left side of the split annular ring may be connected with a first trace and a right side of the annular ring may be connected with a second trace. Alternatively, a multiplexer chip may be used to drive signals and thus the split annular ring may be connected to multiple traces from the conductive traces 425. In various embodiments, eight annular rings are positioned around the axis 455 of the cylindrical tube 445 and exposed on the surface 460; however, it should be understood that more or less than eight split annular rings can be positioned on the cylindrical tube 445. For example, the cylindrical tube 445 can have more or less split annular rings (1, 2, 3, 4, 5, 6, 7, 8, 9, 10, 11, etc.) to enhance design flexibility for the connector 400.

IV. Rib-Cage Connectors and Methods of Manufacture

Figure 5A:
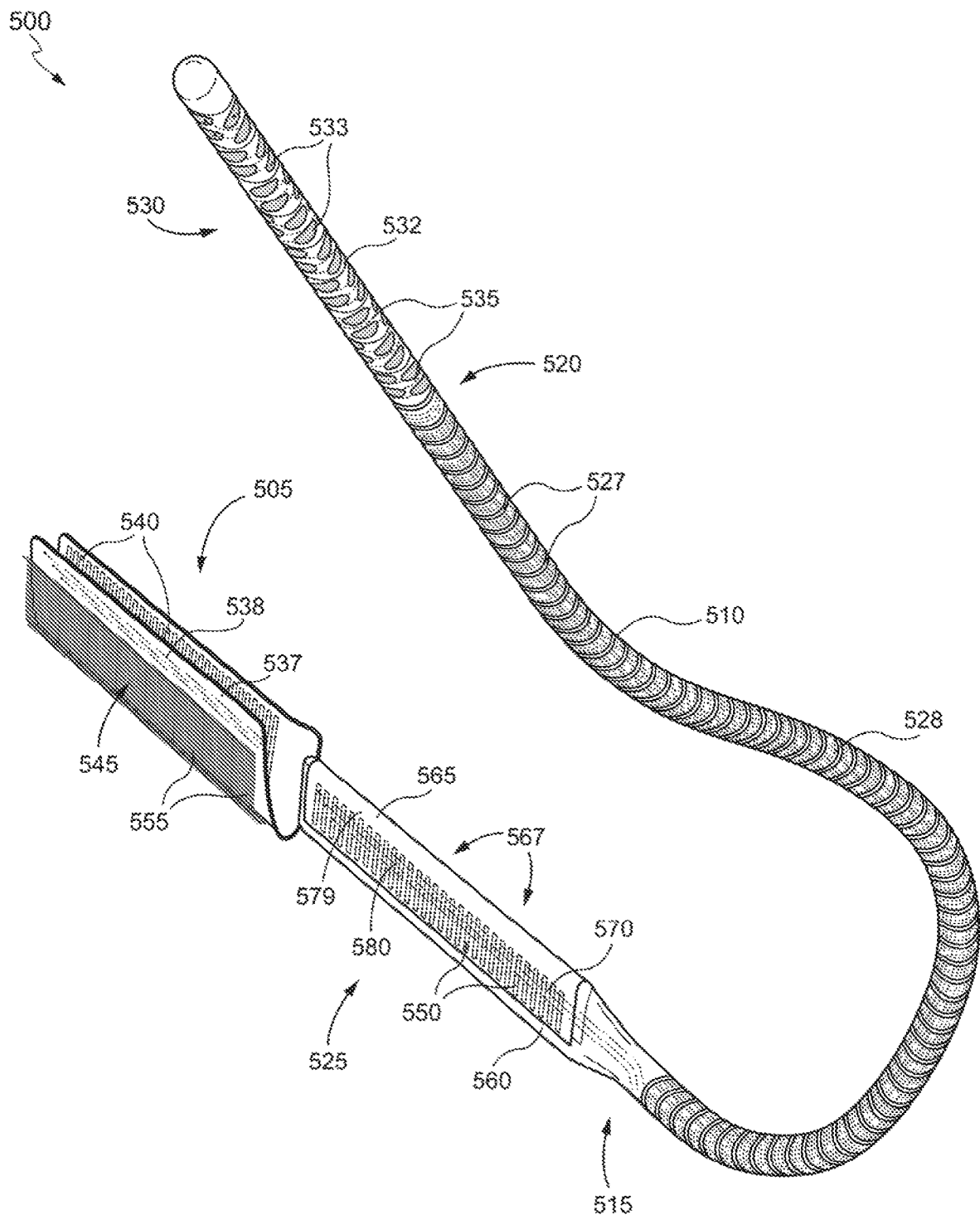
FIG. 5A shows a header and lead assembly in accordance with various embodiments.

FIG. 5A shows a header and lead assembly 500 (e.g., the header 120 and the lead assembly 110 described with respect to FIG. 1) in accordance with aspects of the present disclosure. In various embodiments, the header and lead assembly 500 comprises a header 505, a cable 510 having a proximal end 515 and a distal end 520, and a connector 525 disposed at the proximal end 515 of the cable 510. The header and lead assembly 50) is structured to electrically connect the electronics module of the neurostimulator to electrodes via at least the header 505, the connector 525 and the cable 510. The cable 510 may comprise a supporting structure 527 and a plurality of conductive traces 528 formed on a portion of the supporting structure 527. In some embodiments, the supporting structure 527 is made of one or more layers of dielectric material (i.e., an insulator). The dielectric material may be selected from the group of electrically flexible nonconductive materials consisting of organic or inorganic polymers, polyimide-epoxy, epoxy-fiberglass, and the like. In certain embodiments, the dielectric material is a polymer of imide monomers (i.e., a polyimide), a liquid crystal polymer (LCP) such as Kevlar®, parylene, polyether ether ketone (PEEK), or combinations thereof. In other embodiments, the supporting structure 527 is made of one or more layers of dielectric material formed on a substrate. The substrate may be made from any type of metallic or non-metallic material.

In various embodiments, the one or more conductive traces 528 are a plurality of traces, for example, two or more conductive traces or from two to twenty-four conductive traces. The plurality of conductive traces 528 are comprised of one or more layers of conductive material. The conductive material selected for the one or more conductive traces 528 should have good electrical conductivity and may include pure metals, metal alloys, combinations of metals and dielectrics, and the like. For example, the conductive material may be platinum (Pt), platinum/iridium (Pt/Ir), titanium (Ti), gold/titanium (Au/Ti), or any alloy thereof. In some embodiments, it is also desirable that the conductive material selected for the one or more conductive traces 528 have a CTE that is approximately equal to that of the CTE of the supporting structure 527.

As shown in FIG. 5A, the header and lead assembly 500 may further comprise an electrode assembly 530 formed on a supporting structure 532. The supporting structure 532 may provide support for microelectronic structures including one or more electrodes 533, a wiring layer 535, and optional contact(s) (not shown). The electrode assembly 530 may be located at the distal end 520 of the cable 510. The one or more electrodes 533 are in electrical connection with one or more conductive traces of the plurality of conductive traces 528, for example, via the wiring layer 535 and optionally the contact(s). In various embodiments, the supporting structure 527 of the cable 510 and the supporting structure 532 of the electrode assembly 530 are the same structure (i.e., the supporting structure is continuous), which thus creates a monolithic structure. In alternative embodiments, the supporting structure 527 of the cable 510 and the supporting structure 532 of the electrode assembly 530 are different structures but are connected such that there is an electrical connection between the plurality of conductive traces 528, wiring layer 535, and the one or more electrodes 533.

In various embodiments, the header 505 comprises a supporting structure 537. In some embodiments, the supporting structure 537 is a thin-film comprising one or more layers of dielectric material (i.e., an insulator) that are shaped or folded such that the header 505 has a predetermined shape or profile, for example in a "U" shape (see, e.g., FIGS. 5A, 5B, and 5C). In some embodiments, the one or more layers of dielectric material are one or more layers of polymer. The predetermined shape or profile of the header 505 is structured to receive the predetermined shape or profile (e.g., a blade profile) of the connector 525. In some embodiments, the predetermined shape or profile of the header 505 is structured to wrap around at least a portion of predetermined shape or profile of the connector 525. In certain embodiments, a thickness (g) of the supporting structure 537 is from 0.5 µm to 250 µm or from 1 µm to 100 µm, for example about 50 µm or about 100 µm. The dielectric material may be selected from the group of electrically flexible nonconductive materials consisting of organic or inorganic polymers, polyimide-epoxy, epoxy-fiberglass, and the like. In certain embodiments, the dielectric material is a polymer of imide monomers (i.e., a polyimide), a liquid crystal polymer (LCP) such as Kevlar®, parylene, polyether ether ketone (PEEK), or combinations thereof.

In some embodiments, one or more conductive traces 538 and one or more contacts 540 (i.e., electrically conductive elements, pins, wires, tabs, pads, etc.) are formed on the supporting structure 537 (see, e.g., FIG. 5A). The one or more conductive traces 538 and one or more contacts 540 are structured to electrically connect the header 505 to the electronics module of the neurostimulator. The conductive traces 538 and contacts 540 may be comprised of one or more layers of conductive material for electrical conductivity. The conductive material selected for the conductive traces 538 and contacts 540 should have good electrical conductivity and may include pure metals, metal alloys, combinations of metals and dielectrics, and the like. For example, the conductive material may be platinum (Pt), platinum/iridium (Pt/Ir), titanium (Ti), gold/titanium (Au/Ti), or any alloy thereof. In some embodiments, it is also desirable that the conductive material selected for the conductive traces 538 and contacts 540 have a CTE that is approximately equal to that of a CTE of the supporting structure 537.

Figure 5B:
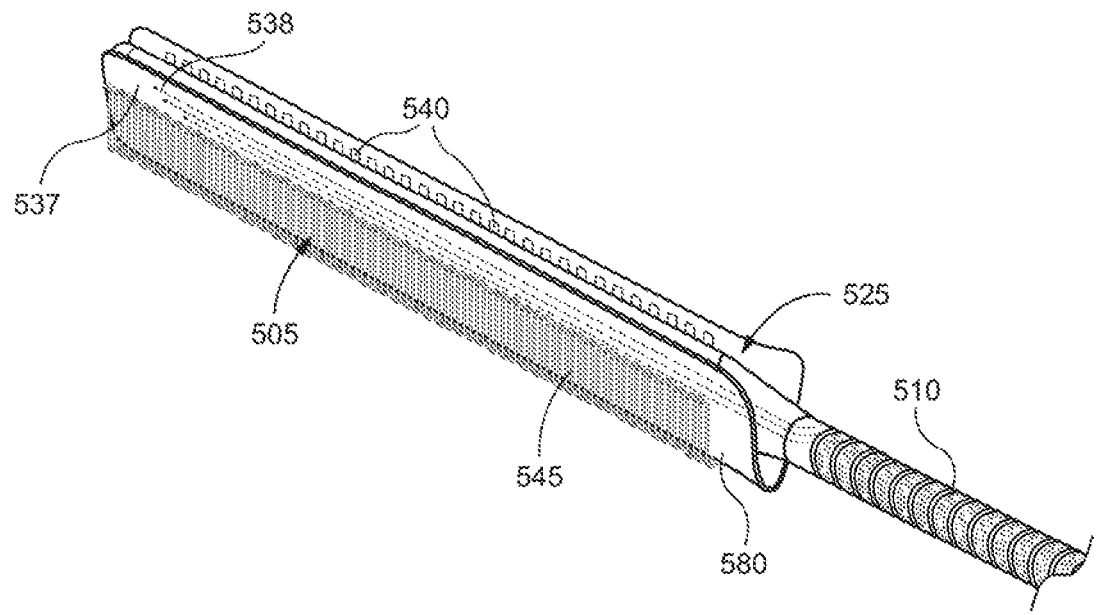
FIGS. 5B-5C show rib-cage connectors in accordance with various embodiments.
Figure 5C:
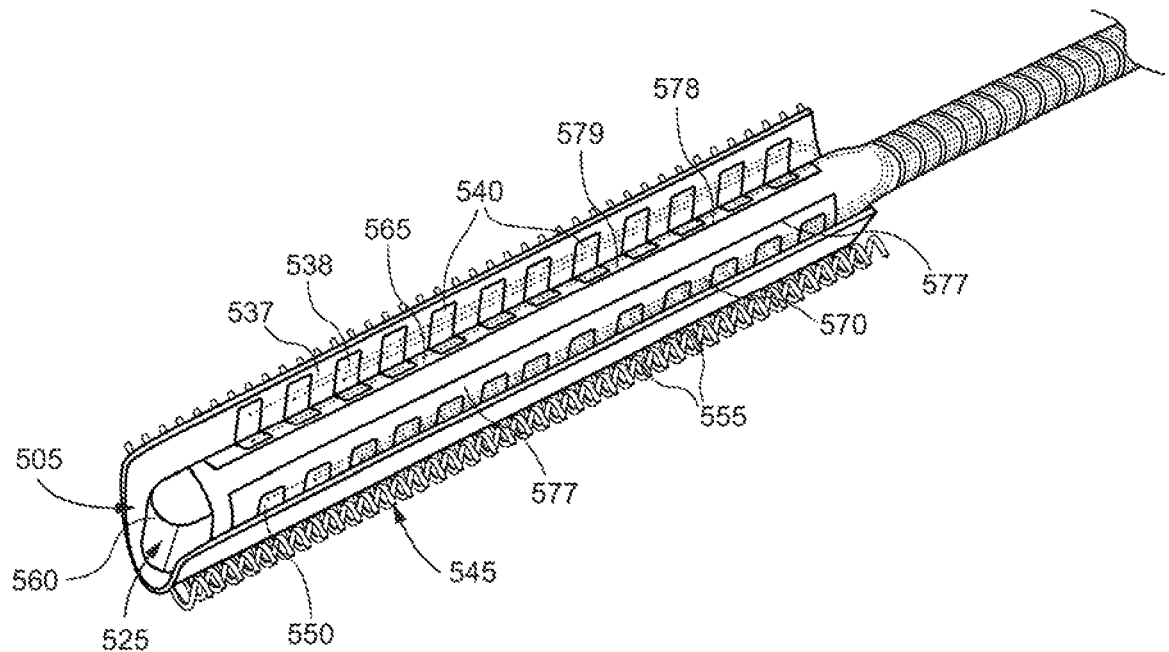

In various embodiments, the header 505 further comprises a clip 545 structured to maintain electrical contact between the contacts 540 and corresponding contacts 550 of the connector 525 (see, e.g., FIGS. 5B and 5C). In some embodiments, the clip 545 is one or more clip springs or spring-fibers 555 arranged into a comb or rib-cage arrangement on the outside of the supporting structure 537. The clip springs or spring-fibers 555 have a spring force that exerts a clasping pressure on the supporting structure 537 to connect the header 505 to the connector 525, as shown in FIGS. 5B and 5C. The thin-film thickness (g) of the supporting structure 537 allows for the spring force of the clip 545 to be distributed across all electrical connections of contacts 540 and corresponding contacts 550 as well as for compliance during insertion of the connector 525 into the header 505. In some embodiments, the clip 545 is held open during insertion of the connector 525 with pull-pins (e.g., pins that may be removed once the connector 525 is inserted into the header 505). In other embodiments, the supporting structure 537 is sufficiently stiff or durable such that the clip 545 is at least partially held open during insertion of the connector 525. For example, a distance that the clip 545 is held open by the supporting structure 530 is no greater than an overall thickness of the connector 525 such that a tight fit is maintained between the header 505 and the connector 525.

In various embodiments, the connector 525 comprises a core 560 and an inlaid supporting structure 565 with a predetermined shape or profile 567 (see, e.g., FIG. 5A). In some embodiments, the core 560 is comprised of one or more layers of material such as polyimide, liquid crystal polymer, parylene, polyether ether ketone, polyurethane, metal, or a combination thereof. In certain embodiments, the one or more layers of material of the core 560 are a TPU. The core 560 may be formed by molding or extrusion with high melting temperature TPU (e.g. Lubrizol Pellethane® 2363-75D, 205C). In some embodiments, the supporting structure 565 is comprised of one or more layers of dielectric material (i.e., an insulator). The layers of dielectric material of the supporting structure 565 may be formed in a FPCB process with metallization layers (e.g., vias or wiring layers) for interconnection. In other embodiments, the supporting structure 565 is made of one or more layers of dielectric material and a coating of a thin layer of a polymer such as TPU. The dielectric material of the supporting structure 565 may be selected from the group of electrically flexible nonconductive materials consisting of organic or inorganic polymers, polyimide-epoxy, epoxy-fiberglass, and the like. In certain embodiments, the dielectric material is a polymer of imide monomers (i.e., a polyimide), a liquid crystal polymer (LCP) such as Kevlar®, parylene, polyether ether ketone (PEEK), or combinations thereof.

In some embodiments, one or more conductive traces 570 and one or more contacts 550 (i.e., electrically conductive elements, pins, wires, tabs, pads, etc.) are formed on the supporting structure 565 (see, e.g., FIG. 5A). The conductive traces 570 and contacts 550 may be comprised of one or more layers of conductive material for electrical conductivity. The conductive material selected for the conductive traces 570 and contacts 550 should have good electrical conductivity and may include pure metals, metal alloys, combinations of metals and dielectrics, and the like. For example, the conductive material may be platinum (Pt), platinum/iridium (Pt/Ir), titanium (Ti), gold/titanium (Au/Ti), or any alloy thereof. In some embodiments, it is also desirable that the conductive material selected for the conductive traces 570 and contacts 550 have a CTE that is approximately equal to that of a CTE of the supporting structure 565. In some embodiments, the supporting structure 527 of the cable 510 and the supporting structure 565 of the connector 525 are the same structure (i.e., the supporting structure is continuous), which thus creates a monolithic cable. In alternative embodiments, the supporting structure 527 of the cable 510 and the supporting structure 565 of the connector 525 are different structures but are connected such that there is an electrical connection between the conductive traces 528, wiring layer 535, the electrodes 533, the conductive traces 570, and the contacts 550.

In various embodiments, the one or more conductive traces 570 are a plurality of traces, for example, two or more conductive traces or from two to twenty-four conductive traces. In some embodiments, at least one trace of the one or more conductive traces 570 terminates at a contact 550 exposed on the outside surface the supporting structure 565. In alternative embodiments, each trace from the one or more conductive traces 570 terminates at a contact 550 exposed on the outside surface the supporting structure 565. As should be understood, in some embodiments, each electrode from the electrodes 533 is electrically connected via a corresponding wiring layer 535, optional contact, conductive trace 527, and conductive trace 570, to a respective contact 550. In other words, each electrode may be electrically connected to a different contact (a one to one relationship). In alternative embodiments, a multiplexer chip may be used such that one or more electrodes from the electrodes 533 is electrically connected via wiring layer 535, optional contact, a conductive trace 527, and conductive trace 570, to a single contact 550. In other words, each electrode may be electrically connected to a same or different contact (a many to one relationship).

The one or more conductive traces 570 may be deposited onto a layer of the supporting structure 565 by using thin film deposition techniques well known to those skilled in the art such as by sputter deposition, chemical vapor deposition, metal organic chemical vapor deposition, electroplating, electroless plating, and the like. In some embodiments, the thickness of the one or more conductive traces 570 is dependent on the particular impedance desired for conductor, in order to ensure excellent signal integrity (e.g., electrical signal integrity for stimulation or recording). For example, if a conductor having a relatively high impedance is desired, a small thickness of conductive material should be deposited onto a layer of the supporting structure 565. If, however, a signal plane having a relatively low impedance is desired, a greater thickness of electrically conductive material should be deposited onto a layer of the supporting structure 565. In certain embodiments, each of the one or more conductive traces 570 has a thickness (t). In some embodiments, the thickness (t) is from 0.5 µm to 25 µm or from 5 µm to 10 µm, for example about 5 µm or about 8 µm. In some embodiments, each of the one or more conductive traces 570 has a length (l) of about 1 mm to 100 µm or 1 cm to 3 cm, e.g., about 15 mm. In some embodiments, each of the one or more conductive traces 570 has a width (w) from 2.0 µm to 500 µm, for example about 30 µm or about 50 µm.

As shown in FIGS. 5A, 5B, and 5C, the connector 525 may be formed with the predetermined shape or profile 567. The predetermined shape or profile 567 acts essentially as a key to assist with alignment in insertion of the connector 525 into the header 505. In some embodiments, the predetermined shape or profile 567 is a blade with the inlaid supporting structure 565 folded over the core 560 creating a first planar sector 577 of contacts 575 positioned on a first side of the blade and a second planar sector 578 of contacts 575 positioned on a second side of the blade (see, e.g., FIG. 5C). In various embodiments, the contacts 575 are formed from split rows of conductive material positioned in columns and exposed on the surface 579 of the supporting structure 565. Each split row may be spaced apart from one another on the surface 579 of the supporting structure 565 by a region 580 of a top layer of the dielectric material. A width or pitch (p) of the region 580 of the top layer of the dielectric material that separates each split row may be between 0.1 mm to 10 mm, for example about 1.0 mm. In some embodiments, each portion of the split row connects to a single trace from the conductive traces 570. In other embodiments, each portion of the split row connects to two or more traces from the conductive traces 570. For example, a left side portion of the split row in first planar sector 577 may be connected with a first trace and a right side portion of the split row in the second planar sector 578 may be connected with a second trace. Alternatively, a multiplexer chip may be used to drive signals and thus the portions of the split row may be connected to multiple traces from the conductive traces 570. In various embodiments, thirty-two split rows are positioned on the supporting structure 565 of the connector 525 and exposed on the surface 579; however, it should be understood that more or less than thirty-two split rows may be positioned on the supporting structure 565. For example, the supporting structure 565 may have an increased surface area to accommodate more rows of contacts 575 and enhance design flexibility for the connector 525. Additionally, the rows may have one split (to isolate columns of contact regions); however, it should be understood that more than one split can be used. For example, the rows may have an increased number of splits (2, 3, 4, 5, 6, etc.) to enhance design flexibility for the second connector 525.

Figure 6A:
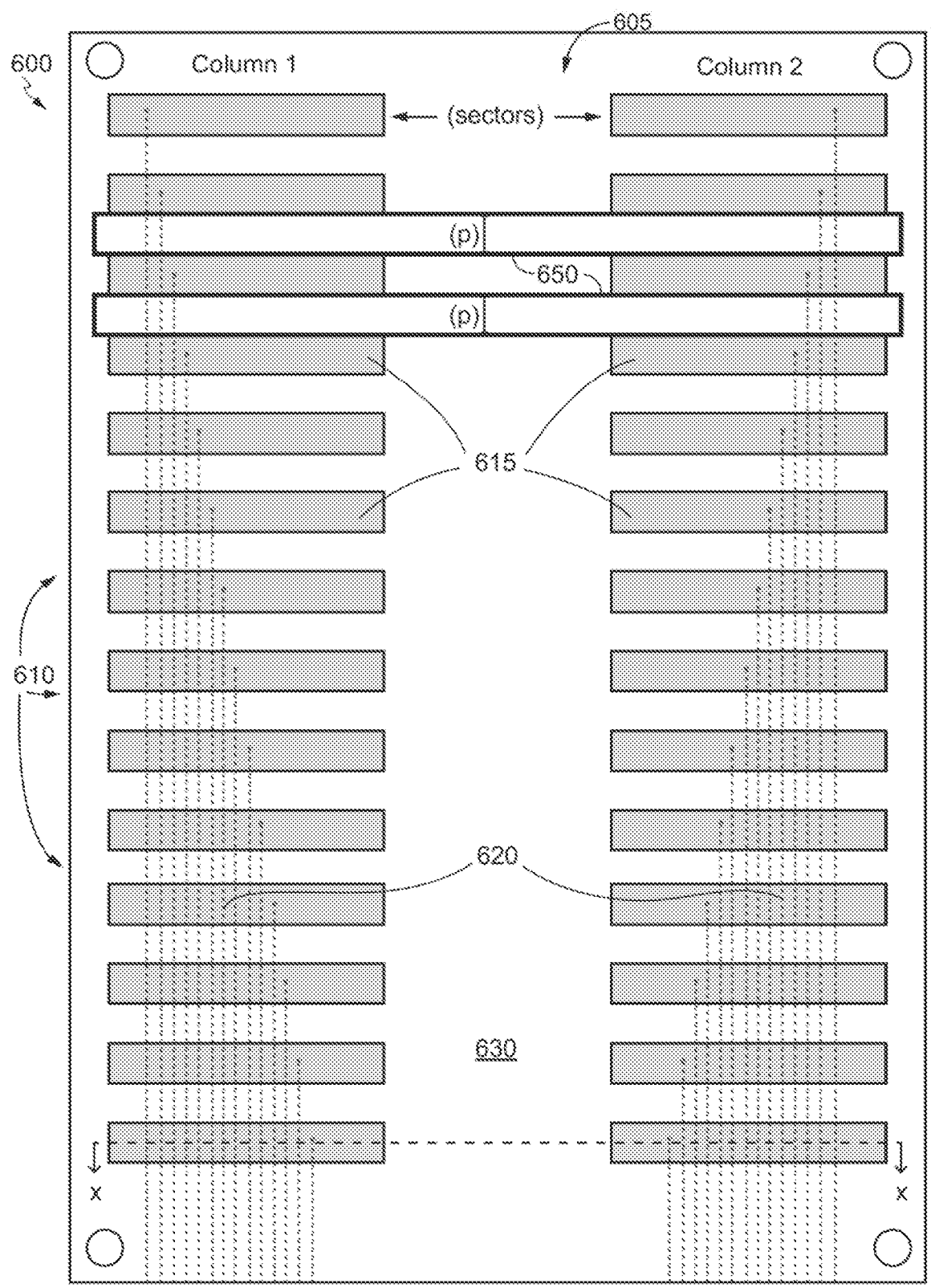
FIGS. 6A-6D show a top view, a bottom view, and cross-sectional side views illustrating a design and method of fabricating a header in accordance with various embodiments.

As shown in FIGS. 6A (frontside), 6B (backside), and 6C, a header 600 (e.g., the header 505 as discussed with respect to FIGS. 5A-5C) may be formed of a supporting structure 605 with a predetermined layout 610 of contacts 615 and conductive traces 620. In some embodiments, the supporting structure 605 is made of one or more layers of dielectric material formed on an optional substrate. The substrate may be made from any type of metallic or non-metallic material such as polyimide, liquid crystal polymer, parylene, polyether ether ketone, polyurethane, TPU, metal, or a combination thereof. As shown in FIG. 6C (cross-section of the connector 600 along X-X from FIGS. 6A and 6B), the supporting structure 605 may comprise a first layer of dielectric material 630 and a second layer of dielectric material 635 with the conductive traces 620 buried between the first layer of dielectric material 630 and the second layer of dielectric material 635. In some embodiments, the first layer of dielectric material 630 comprises at least one contact via 640 for each contact 615. The contact via 640 may comprise a conductive material for electrically connecting each contact 615 to at least one trace of the conductive traces 620 such that each trace of the conductive traces 620 terminates at a contact 615. The contact via 640 may be connected to the at least one trace of the conductive traces 620 directly or indirectly by way of a wiring layer (not shown). In some embodiments, the conductive material is lined on at least a portion of the walls of the via hole. In other embodiments, the conductive material fills the via hole.

Figure 6B:
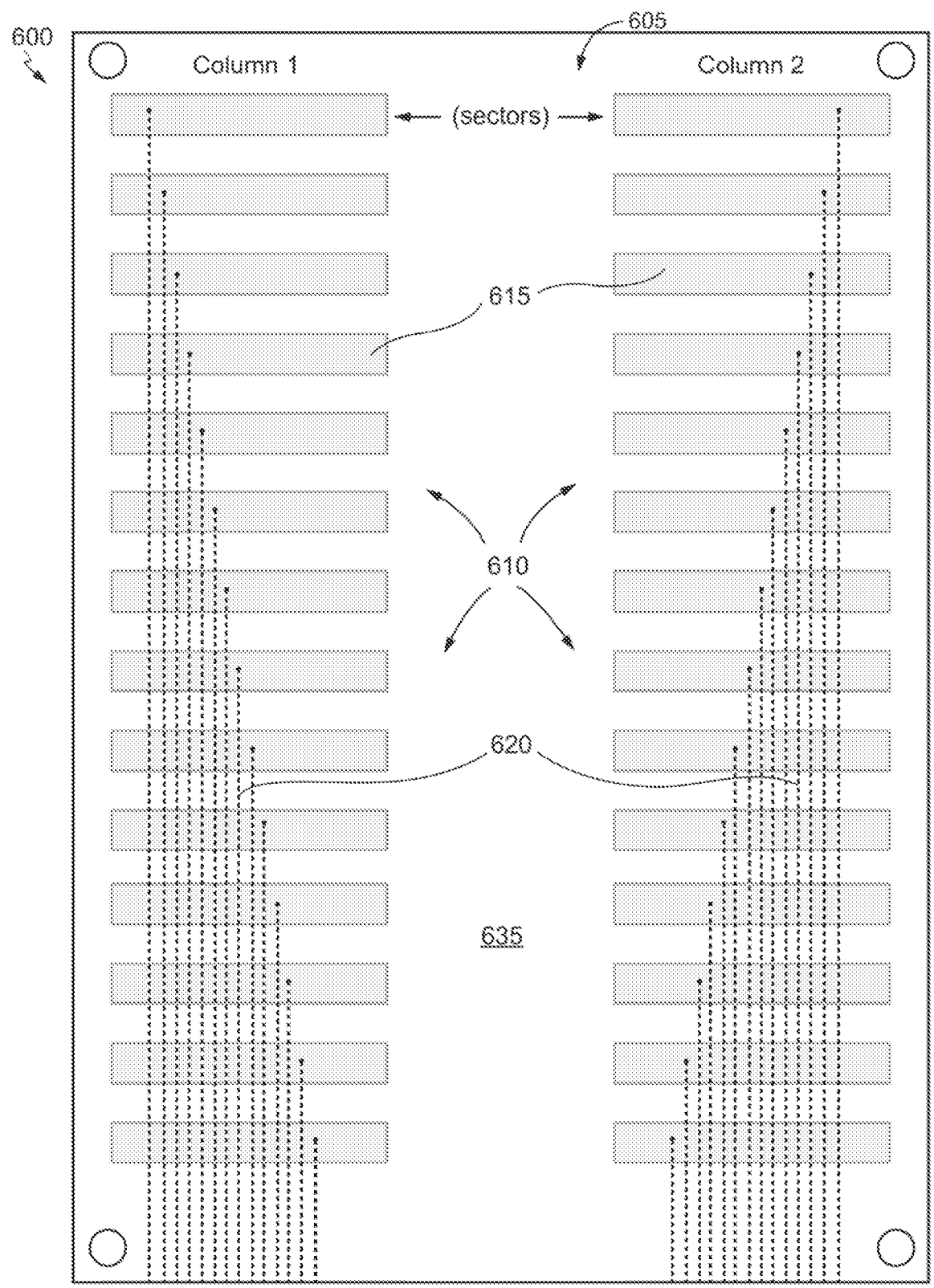
Figure 6C:
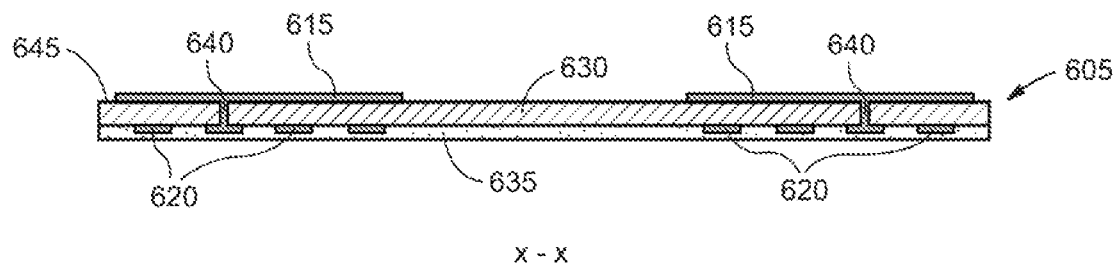

In various embodiments, the contacts 615 are provided as split rows positioned in columns on sectors or faces of the supporting structure 605 (see, e.g., FIGS. 6A and 6B). In some embodiments, a first portion of the split rows is disposed in a first sector of the sectors and a second portion of the split rows is disposed in a second sector of the sectors. The first sector may be located on a first side of the header 600 and the second sector may be located on a second side of the header 600. In some embodiments, the contacts 615 are exposed on the surface 645 of the supporting structure 605 (see, e.g., FIGS. 6C and 6D). For example, the contacts 615 may be raised above a surface of the supporting structure 605 (e.g., a top surface of the contacts 615 protrudes above a top surface of the supporting structure 605) and comprise an anti-abrasive finish. In certain embodiments, the contacts 615 are raised above the surface 645 of the supporting structure 605 by a predetermined distance. The predetermined distance is from 0.05 mm to 1.0 mm, for example about 0.5 mm. Moreover, each split row may be spaced apart from one another on the surface 645 of the supporting structure by a region 650 of the first layer of the dielectric material 630 (see, e.g., FIGS. 6A and 6B). A width or pitch (p) of the region 650 of the first layer of the dielectric material 630 that separates each split row may be between 1.0 mm to 10 mm, for example about 1 mm. In some embodiments, each contact 615 of a split row connects to a single trace of the conductive traces 620. In other embodiments, each contact 615 of a split row connects to two or more traces from the conductive traces 620. For example, a left side of the split row may be connected with a first trace and a right side of the split row may be connected with a second trace. Alternatively, a multiplexer chip may be used to drive signals and thus the split row may be connected to multiple traces from the conductive traces 620. In various embodiments, thirty-two split rows are positioned on the supporting structure 605 and exposed on the surface 645; however, it should be understood that more or less than thirty-two split rows can be positioned on the supporting structure 605. For example, the supporting structure 605 can accommodate more or less split rows (10, 24, 30, 42, 48, 50 etc.) to enhance design flexibility for the first connector 600.

Figure 6D:
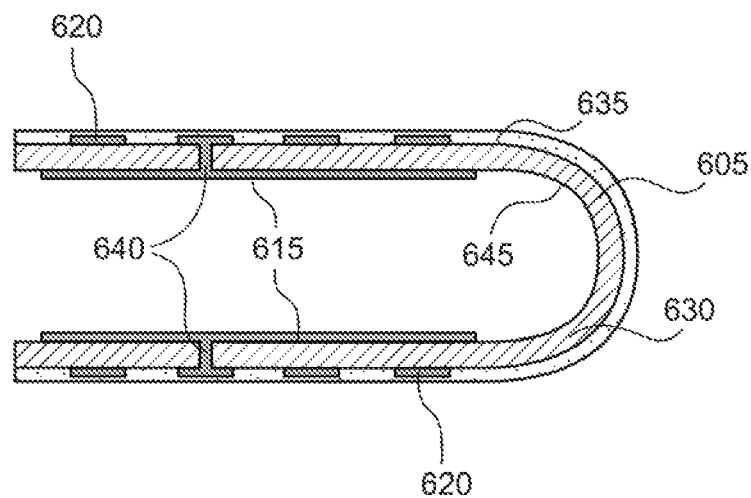

As shown in FIG. 6D, the supporting structure 605 may be shaped or folded such that the contacts 615 face inwardly. The supporting structure 605 may then be baked to thermoform the supporting structure 605 into a final shape, for example in a "U" shape. In some embodiments, the first layer of dielectric material 630 is a first type of polymer material, e.g., a high temperature liquid crystal polymer or a low temperature liquid crystal polymer, that acts as an overlay for insulation, and the second layer of dielectric material 635 is a second type of polymer material, e.g., a high temperature liquid crystal polymer or a low temperature liquid crystal polymer, that acts as an overlay for insulation. Although the header 600 is shown in FIG. 6D and described with respect to a "U" shape, it should be understood that other shapes for the header have been contemplated, for example, spherical cubed, torus, ellipsoid, etc.

Figure 6E:
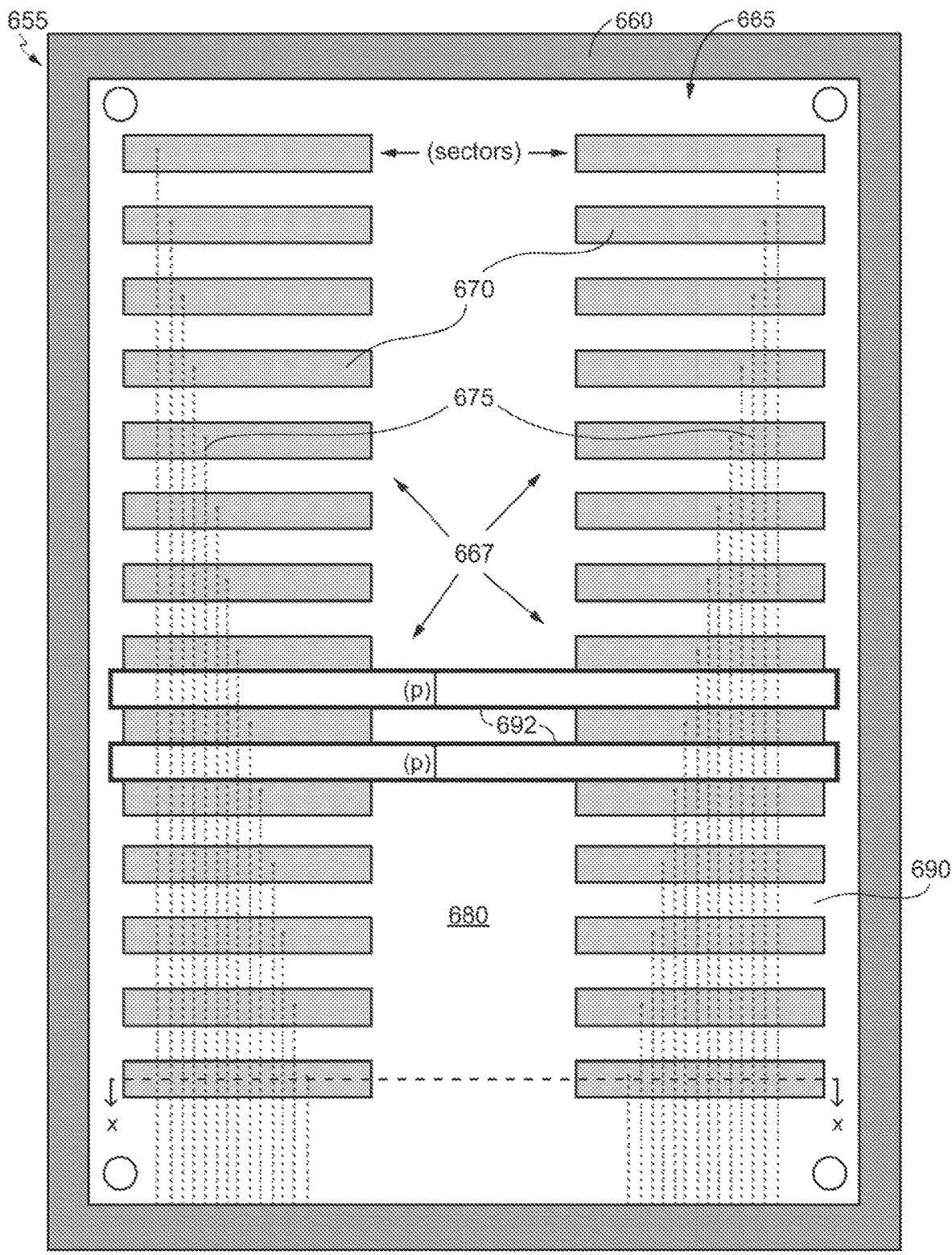
FIGS. 6E-6H show a top view, a bottom view, and cross-sectional side views illustrating a design and method of fabricating a connector in accordance with various embodiments.

As shown in FIGS. 6E (frontside) and 6F (backside), the connector 655 (e.g., the connector 525 as discussed with respect to FIGS. 5A, 5B, and 5C) may be formed of a core 660 and an inlaid supporting structure 665 with a predetermined layout 667 of contacts 670 and conductive traces 675. As shown in FIG. 6G (cross-section of the connector 655 along X-X from FIGS. 6E and 6F), the supporting structure 665 may comprise a first layer of dielectric material 680 and a second layer of dielectric material 685 with the conductive traces 675 buried between the first layer of dielectric material 680 and the second layer of dielectric material 685. In some embodiments, the first layer of dielectric material 680 comprises at least one contact via 687 for each contact 670. The contact via 687 may comprise a conductive material for electrically connecting each contact 670 to at least one trace of the conductive traces 675 such that each trace of the conductive traces 675 terminates at a contact 670. The contact via 687 may be connected to the at least one trace of the conductive traces 675 directly or indirectly by way of a wiring layer (not shown). In some embodiments, the conductive material is lined on at least a portion of the walls of the via hole. In other embodiments, the conductive material fills the via hole.

Figure 6F:
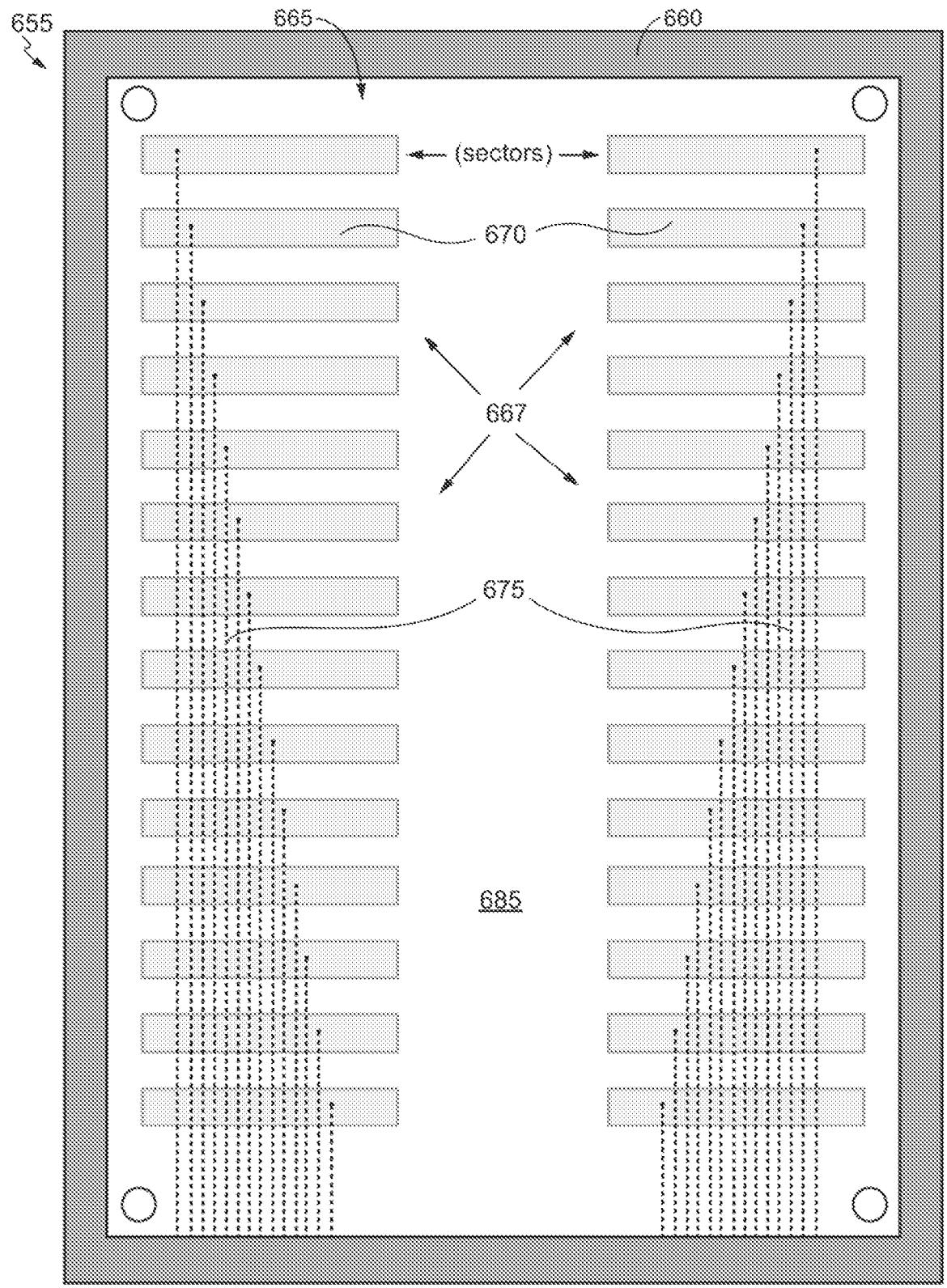
Figure 6G:
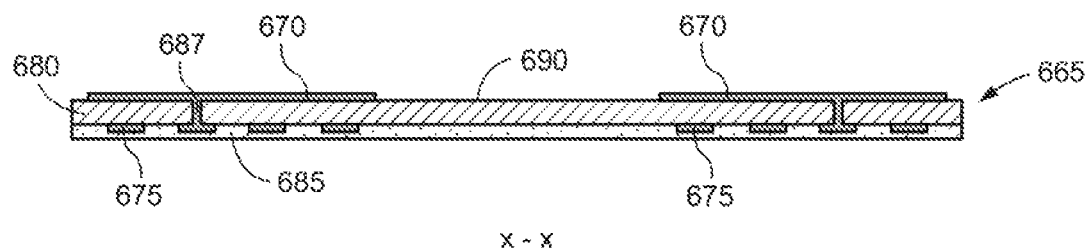

In various embodiments, the contacts 670 are provided as split rows positioned in columns on sectors or faces of the supporting structure 665 (see, e.g., FIGS. 6E and 6F). In some embodiments, a first portion of the split rows is disposed in a first sector of the sectors and a second portion of the split rows is disposed in a second sector of the sectors. The first sector may be located on a first side of the connector 655 and the second sector is located on a second side of the connector 655. In some embodiments, the contacts 670 are exposed on the surface 690 of the supporting structure 665 (see, e.g., FIG. 6G). For example, the contacts 670 may be raised above a surface of the supporting structure 665 (e.g., a top surface of the contacts 670 protrudes above a top surface of the supporting structure 665) and comprise an anti-abrasive finish. In certain embodiments, the contacts 670 are raised above the surface 690 of the supporting structure 665 by a predetermined distance. The predetermined distance is from 0.05 mm to 1.0 mm, for example about 0.5 mm. Moreover, each split row may be spaced apart from one another on the surface 690 of the supporting structure by a region 692 of the first layer of the dielectric material 680 (see, e.g., FIG. 6E). A width or pitch (p) of the region 692 of the first layer of the dielectric material 680 that separates each split row may be between 1.0 mm to 10 mm, for example about 1 mm. In some embodiments, each contact 670 of a split row connects to a single trace of the conductive traces 675. In other embodiments, each contact 670 of a split row connects to two or more traces from the conductive traces 675. For example, a left side of the split row may be connected with a first trace and a right side of the split row may be connected with a second trace. Alternatively, a multiplexer chip may be used to drive signals and thus the split row may be connected to multiple traces from the conductive traces 675. In various embodiments, thirty-two split rows are positioned on the supporting structure 665 and exposed on the surface 690; however, it should be understood that more or less than thirty-two split rows can be positioned on the supporting structure 665. For example, the supporting structure 665 can accommodate more or less split rows (10, 24, 30, 42, 48, 50 etc.) to enhance design flexibility for the connector 655.

Figure 6H:
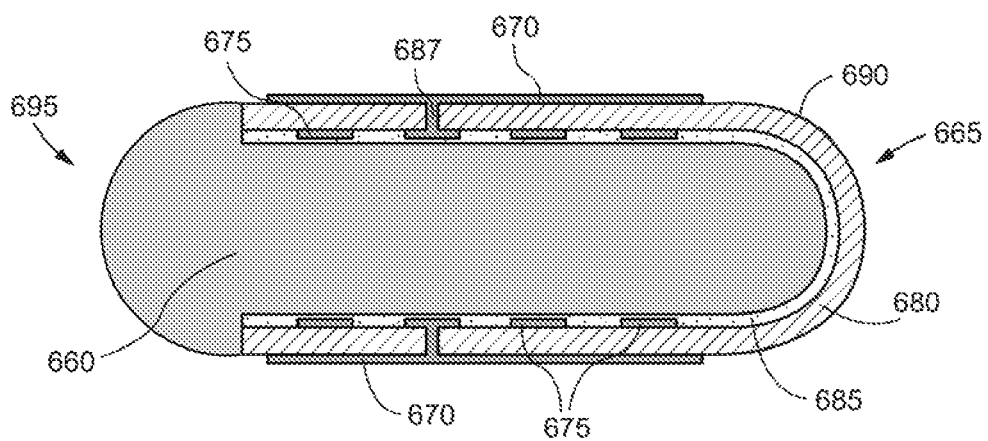

As shown in FIG. 6H, the supporting structure 665 may be shaped or folded on the core 660 (e.g., an injection molded core) such that the contacts 670 face outwardly. In various embodiments, the core 660 and the supporting structure 665 may be formed with a predetermined shape or profile 695 (e.g., a blade as shown in FIG. 6H). The predetermined shape or profile 695 acts essentially as a key to assist with alignment in insertion of the second connector 655 into the header 600. As shown in FIG. 6H, the shape or profile 695 comprises the one or more layers of dielectric material 680/685 at least partially wrapped around the core 660, e.g., a "U" shaped wrapping. The first layer of dielectric material 680 may define an outer width (n) of the shape or profile 695 and the second layer of dielectric material 685 may define an inner width (n') of the shape or profile 695. The shape or profile 695 may further comprise the core 660 that at least partially fills a space interior of the shape or profile 695 defined by the inner width (n') of the shape or profile 695. The core 660 may be comprised of one or more layers of material such that the core 660 has a Shore durometer of greater than 70D. In some embodiments, the one or more layers of material of the core 660 is polyimide, liquid crystal polymer, parylene, polyether ether ketone, polyurethane, metal, or a combination thereof. In certain embodiments, the one or more layers of material of the core 660 is a TPU. Although the connector 655 is shown in FIG. 6H and described with respect to a blade shape, it should be understood that other shapes for the connector have been contemplated, for example, spherical cubed, torus, ellipsoid, etc.

Once the core 660 and the supporting structure 665 are shaped, the core 660 and the supporting structure 665 may then be inserted into a heat shrink tube (e.g., FEP Lay-Flat™ Heat Shrink) and baked to thermoform the core 660 and supporting structure 665 into a final shape, for example a blade, as shown in FIG. 6H. The core 660 and the supporting structure 665 may be reflowed at 130° C.-150° C. (e.g., 137° C.) using the second layer of dielectric material 685 as an adhesive to attach the core 660 to the supporting structure 665. In some embodiments, the first layer of dielectric material 680 is a first type of polymer material, e.g., a high temperature liquid crystal polymer, that acts as an overlay for insulation, and the second layer of dielectric material 685 is a second type of polymer material, e.g., a low temperature liquid crystal polymer, that acts as an adhesive for bonding the supporting structure 665 to the core 660, as shown in FIG. 6H.

V. Extension Connectors and Methods of Manufacture

Figure 7A:
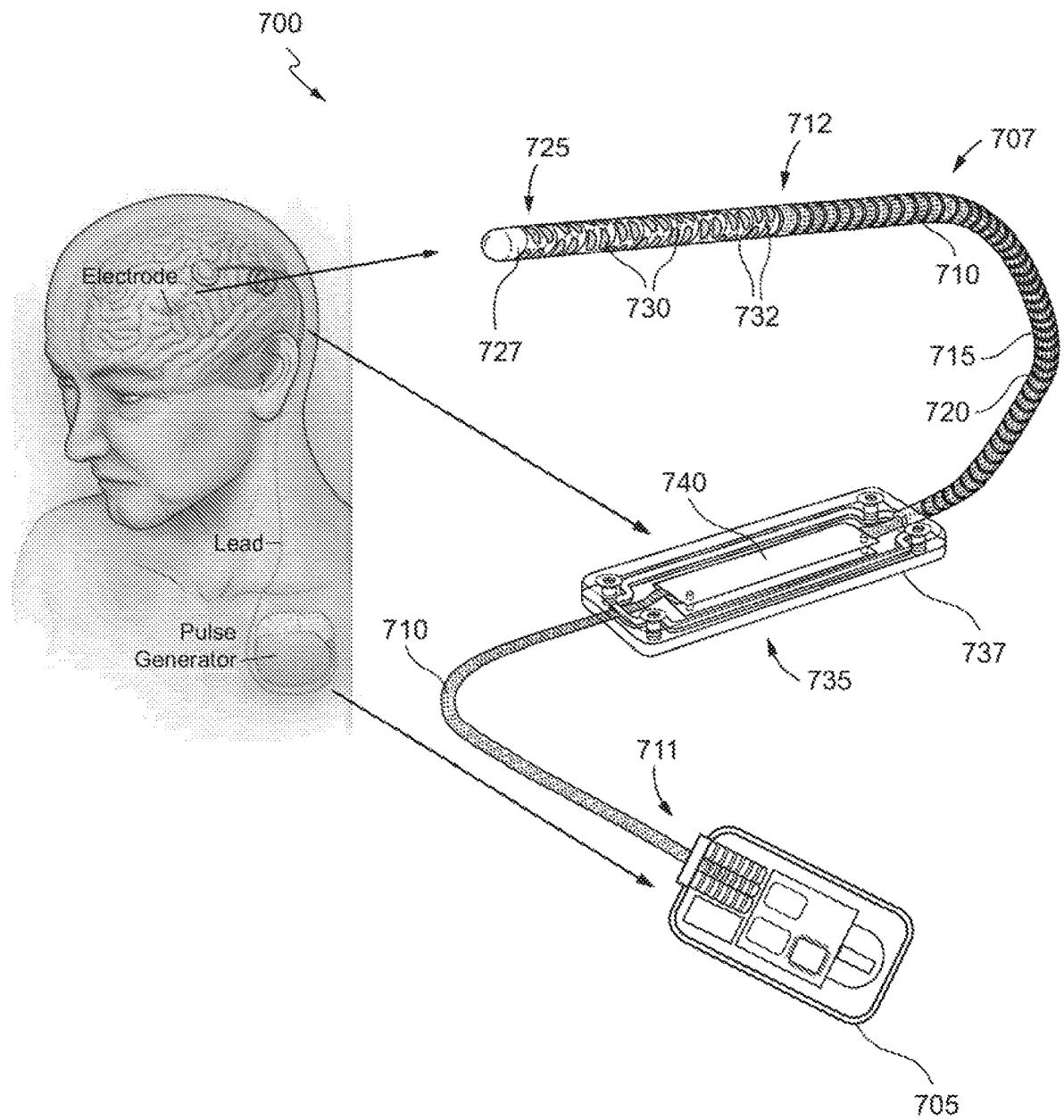
FIG. 7A shows a neuromodulation system in accordance with various embodiments.

FIG. 7A shows a neuromodulation system 700 (e.g., the neuromodulation system 100 described with respect to FIG. 1) in accordance with aspects of the present disclosure. In various embodiments, the neuromodulation system 700 comprises an implantable neurostimulator 705 and a lead assembly 707. The lead assembly 707 includes two or more cables 710, a proximal end 711, and a distal end 712. Each cable 710 may comprise a supporting structure 715 and a plurality of conductive traces 720 formed on a portion of the supporting structure 715. In some embodiments, the supporting structure 715 is made of one or more layers of dielectric material (i.e., an insulator). The dielectric material may be selected from the group of electrically flexible nonconductive materials consisting of organic or inorganic polymers, polyimide-epoxy, epoxy-fiberglass, and the like. In certain embodiments, the dielectric material is a polymer of imide monomers (i.e., a polyimide), a liquid crystal polymer (LCP) such as Kevlar®, parylene, polyether ether ketone (PEEK), or combinations thereof. In other embodiments, the supporting structure 715 is made of one or more layers of dielectric material formed on a substrate. The substrate may be made from any type of metallic or non-metallic material.

In various embodiments, the one or more conductive traces 720 are a plurality of traces, for example, two or more conductive traces or from two to twenty-four conductive traces. The plurality of conductive traces 720 are comprised of one or more layers of conductive material. The conductive material selected for the one or more conductive traces 720 should have good electrical conductivity and may include pure metals, metal alloys, combinations of metals and dielectrics, and the like. For example, the conductive material may be platinum (Pt), platinum/iridium (Pt/Ir), titanium (Ti), gold/titanium (Au/Ti), or any alloy thereof. In some embodiments, it is also desirable that the conductive material selected for the one or more conductive traces 720 have a CTE that is approximately equal to that of the CTE of the supporting structure 715.

As shown in FIG. 7A, the lead assembly 707 may further comprise an electrode assembly 725 formed on a supporting structure 727. The supporting structure 727 may provide support for microelectronic structures including one or more electrodes 730, a wiring layer 732, and optional contact(s) (not shown). The electrode assembly 707 may be located at the distal end 712 of the lead assembly 707. The one or more electrodes 730 are in electrical connection with one or more conductive traces of the plurality of conductive traces 720, for example, via the wiring layer 732 and optionally the contact(s). In various embodiments, the supporting structure 715 of at least one cable 710 and the supporting structure 727 of the electrode assembly 725 are the same structure (i.e., the supporting structure is continuous), which thus creates a monolithic structure. In alternative embodiments, the supporting structure 715 of at least one cable 710 and the supporting structure 727 of the electrode assembly 725 are different structures but are connected such that there is an electrical connection between the plurality of conductive traces 720, wiring layer 732, and the one or more electrodes 730.

Figure 7B:
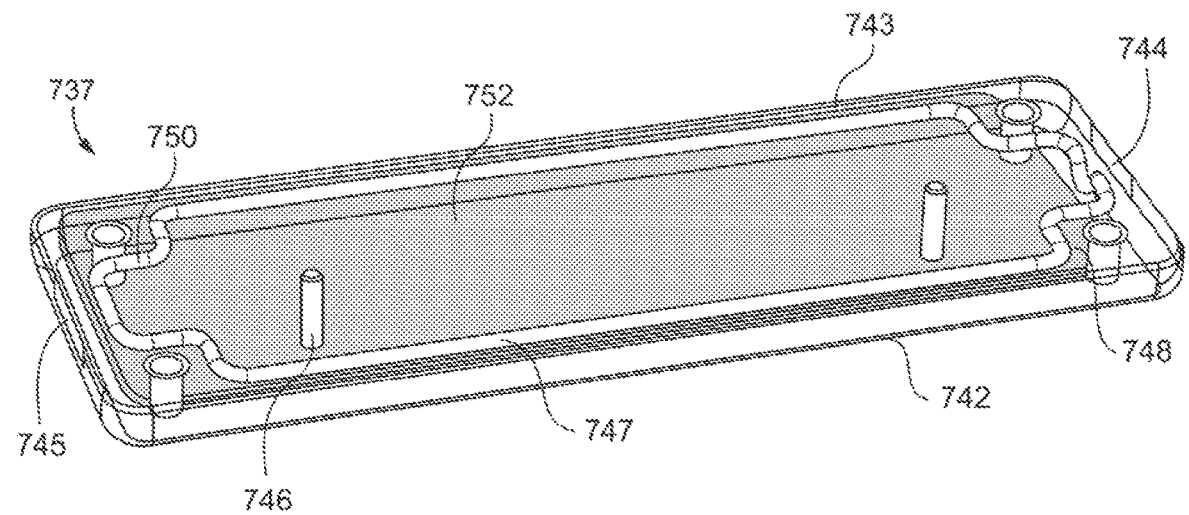
FIGS. 7B-7F show a connection assembly in accordance with various embodiments.

As shown in FIG. 7A, the lead assembly 707 may further comprise one or more extension devices 735 for connecting the two or more cables 710. Each extension device 735 comprises a housing 737 and a connection assembly 740. In various embodiments, the housing 737 comprises a first half portion 742 (e.g., a bottom half), a second half portion 743 (e.g., a top half), a distal port 744, and a proximal port 745, as shown in FIG. 7B. The first half portion 742 and the second half portion 743 may be formed of a polymer material. The polymer material may be imide monomers (i.e., a polyimide), a liquid crystal polymer (LCP) such as Kevlar®, parylene, polyether ether ketone (PEEK), or combinations thereof. The distal port 744 may be structured to receive a first cable of the two or more cables 710, and the proximal port 745 may structure to receive a second cable of the two or more cables 710. In some embodiments, the distal port 744 and/or the proximal port 745 are disposed within the first half portion 742 (e.g., a scalable through-hole in a side of the first portion 742). In other embodiments, the distal port 744 and/or the proximal port 745 are disposed within the second half portion 743 (e.g., a scalable through-hole in a side of the second portion 743). In other embodiments, the distal port 744 and/or the proximal port 745 are disposed in a space between the first half portion 742 and the second half portion 743 (e.g., in a scalable slot between the two halves). The distal port 744 and/or the proximal port 745 may be sealed by mating the through-hole or slot with other components such as a sealing ring.

Figure 7C:
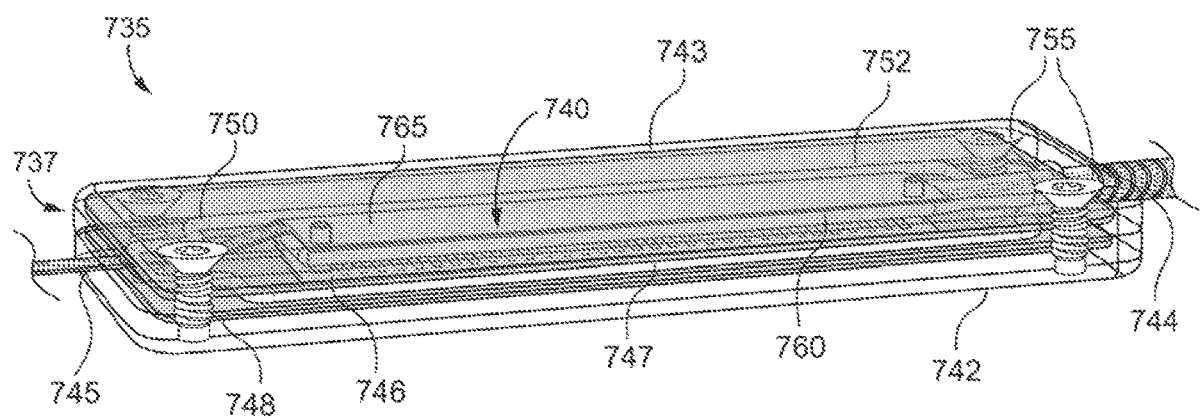

In some embodiments, the first half portion 742 comprises one or more alignment pins 746, a seal 747, and a first compliant pad 748, as shown in FIGS. 7B and 7C. The second half portion 743 comprises an optional seal 750, a second compliant pad 752, and one or more attachment features 755 (e.g., screws) for attaching the first half portion 742 and the second half portion 743, as shown in FIGS. 7B and 7C. The alignment pins 746 may be made of a polymer, metal, or combination thereof, and are structured to align the connection assembly 740 within the housing 737, as described in further detail herein with reference to FIG. 7D. The seals 747 and 750 may be made of polyurethane, polycarbonate, silicone, polyethylene, fluoropolymer and/or other medical polymers, copolymers and combinations or blends thereof. The first compliant pad 748 and the second compliant pad 752 may be foam compression pads structured to assist in compression or maintaining electrical contact within the connector, as described in further detail herein with reference to FIG. 7D. The foam compression pads may be made of polyurethane, polycarbonate, silicone, polyethylene, fluoropolymer and/or other medical polymers, copolymers and combinations or blends thereof. In some embodiments, the one or more attachment features 755 attach the first half portion 742 and the second half portion 743 as well as compressing the seal 747, optionally seal 750, the first compliant pad 748, and the second compliant pad 752 within the housing 737.

Figure 7D:
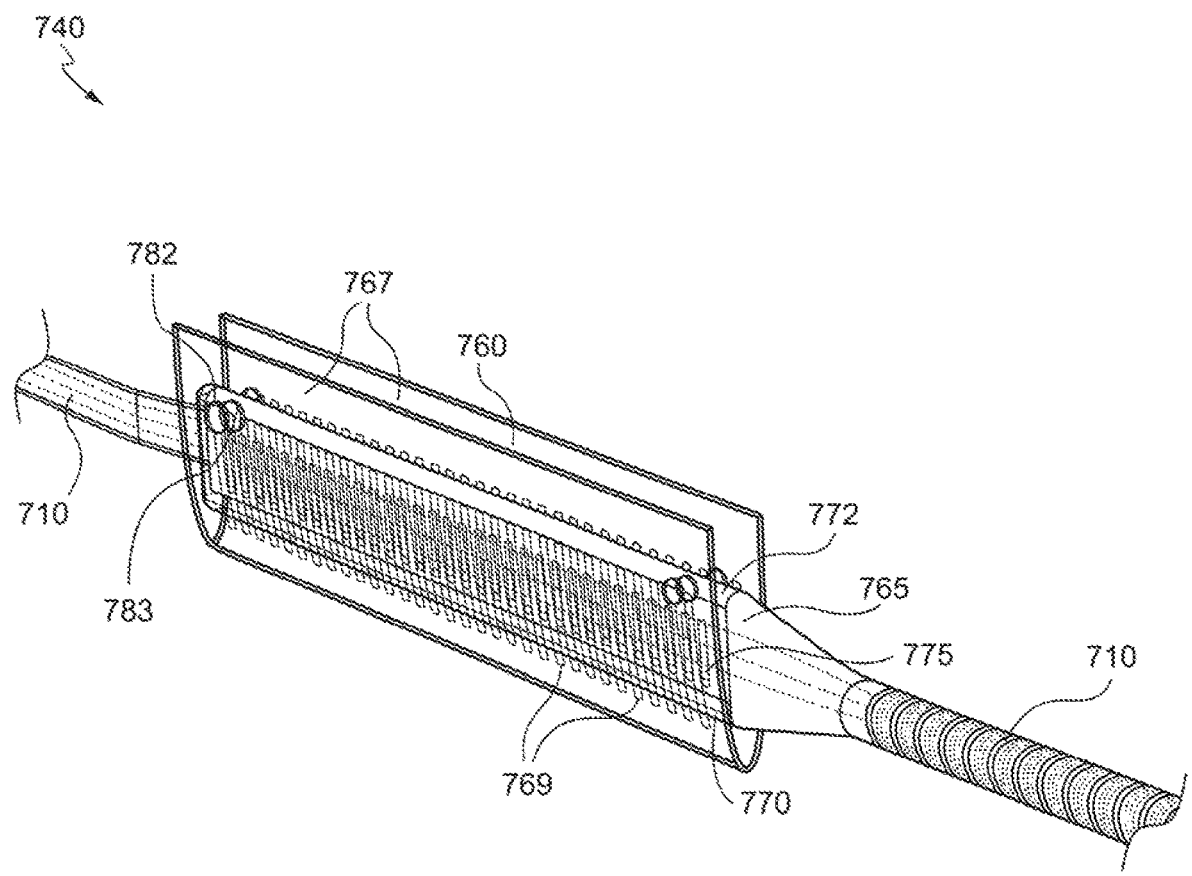
Figure 7E:
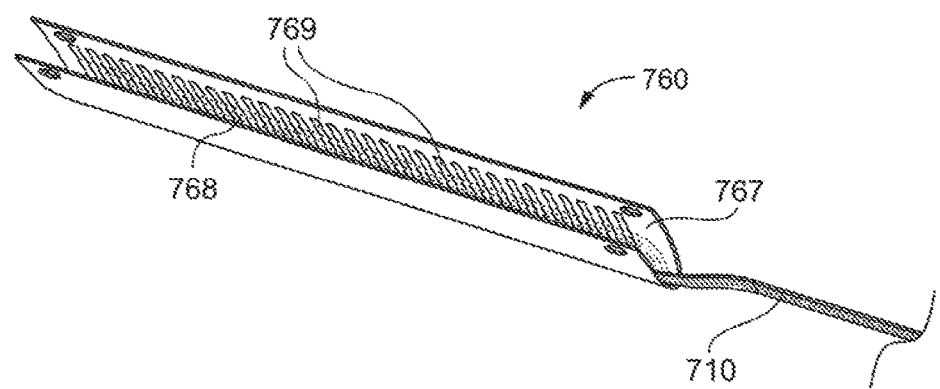

FIGS. 7D and 7E show a connection assembly 740 in accordance with aspects of the present disclosure. In various embodiments, the connection assembly 740 comprises a first connector 760 and a second connector 765. The first connector 760 may be disposed at an end (e.g., a distal end) of the first cable of the two or more cables 710. The second connector 765 may be disposed at an end (e.g., the proximal end) of the second cable of the two or more cables 710. The connection assembly 740 is structured to electrically connect the first cable to the second cable, and thus extend an overall length of the lead assembly 707. In various embodiments, the fist connector 760 comprises a supporting structure 767. In some embodiments, the supporting structure 767 is a thin-film comprising one or more layers of dielectric material (i.e., an insulator) that are shaped or folded, for example in a "U" shape (see, e.g., FIG. 7E). In some embodiments, the one or more layers of dielectric material are one or more layers of polymer. In certain embodiments, a thickness (g) of the supporting structure 767 is from 0.5 μm to 250 μm or from 1 μm to 100 μm, for example about 50 μm or about 100 μm. The dielectric material may be selected from the group of electrically flexible nonconductive materials consisting of organic or inorganic polymers, polyimide-epoxy, epoxy-fiberglass, and the like. In certain embodiments, the dielectric material is a polymer of imide monomers (i.e., a polyimide), a liquid crystal polymer (LCP) such as Kevlar®, parylene, polyether ether ketone (PEEK), or combinations thereof.

In some embodiments, one or more conductive traces 768 and one or more contacts 769 (i.e., electrically conductive elements, pins, wires, tabs, pads, etc.) are formed on the supporting structure 767 (see, e.g., FIG. 7E). The conductive traces 768 and contacts 769 may be comprised of one or more layers of conductive material for electrical conductivity. The conductive material selected for the conductive traces 768 and contacts 769 should have good electrical conductivity and may include pure metals, metal alloys, combinations of metals and dielectrics, and the like. For example, the conductive material may be platinum (Pt), platinum/iridium (Pt/Ir), titanium (Ti), gold/titanium (Au/Ti), or any alloy thereof. In some embodiments, it is also desirable that the conductive material selected for the conductive traces 768 and contacts 769 have a CTE that is approximately equal to that of a CTE of the supporting structure 767. In some embodiments, the supporting structure 715 of the first cable 710 and the supporting structure 767 of the first connector 760 are the same structure (i.e., the supporting structure is continuous), which thus creates a monolithic cable. In alternative embodiments, the supporting structure 715 of the first cable 710 and the supporting structure 767 of the first connector 760 are different structures but are connected such that there is an electrical connection between the conductive traces 720, wiring layer 732, the electrodes 730, the conductive traces 768, and the contacts 769.

Figure 7F:
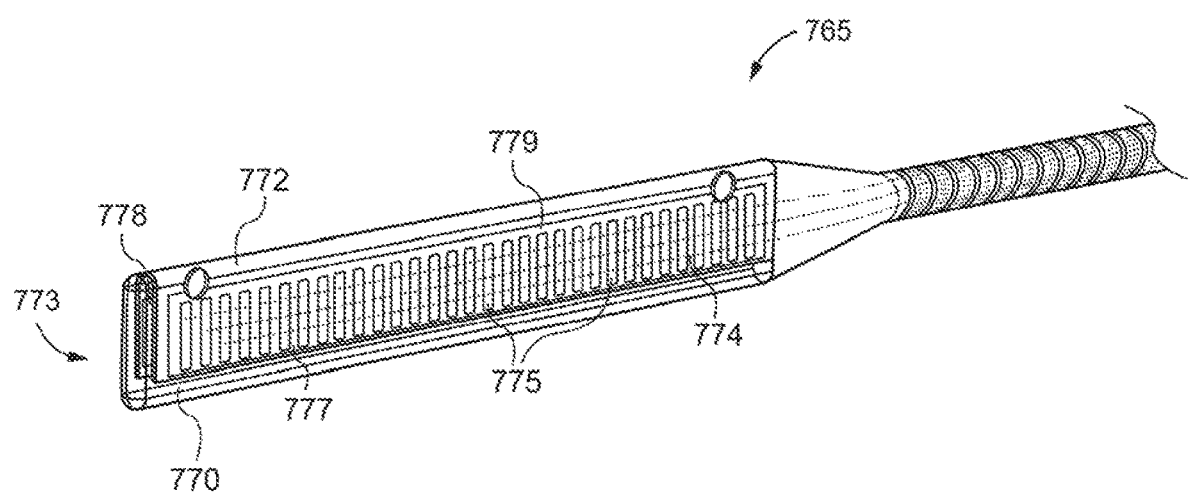

In various embodiments, the second connector 765 comprises a core 770 and an inlaid supporting structure 772 with a predetermined shape or profile 773 (see, e.g., FIG. 7F). In some embodiments, the core 770 is comprised of one or more layers of material such as polyimide, liquid crystal polymer, parylene, polyether ether ketone, polyurethane, metal, or a combination thereof. In certain embodiments, the one or more layers of material of the core 770 are a TPU. The core 770 may be formed by molding or extrusion with high melting temperature TPU (e.g. Lubrizol Pellethane® 2363-75D, 205C). In some embodiments, the supporting structure 772 is comprised of one or more layers of dielectric material (i.e., an insulator). The layers of dielectric material of the supporting structure 772 may be formed in a FPCB process with metallization layers (e.g., vias or wiring layers) for interconnection. In other embodiments, the supporting structure 772 is made of one or more layers of dielectric material and a coating of a thin layer of a polymer such as TPU. The dielectric material of the supporting structure 772 may be selected from the group of electrically flexible nonconductive materials consisting of organic or inorganic polymers, polyimide-epoxy, epoxy-fiberglass, and the like. In certain embodiments, the dielectric material is a polymer of imide monomers (i.e., a polyimide), a liquid crystal polymer (LCP) such as Kevlar®, parylene, polyether ether ketone (PEEK), or combinations thereof.

In some embodiments, one or more conductive traces 774 and one or more contacts 775 (i.e., electrically conductive elements, pins, wires, tabs, pads, etc.) are formed on the supporting structure 772 (see, e.g., FIG. 7F). The conductive traces 774 and contacts 775 may be comprised of one or more layers of conductive material for electrical conductivity. The conductive material selected for the conductive traces 774 and contacts 775 should have good electrical conductivity and may include pure metals, metal alloys, combinations of metals and dielectrics, and the like. For example, the conductive material may be platinum (Pt), platinum/iridium (Pt/Ir), titanium (Ti), gold/titanium (Au/Ti), or any alloy thereof. In some embodiments, it is also desirable that the conductive material selected for the conductive traces 774 and contacts 775 have a CTE that is approximately equal to that of a CTE of the supporting structure 772. In some embodiments, the supporting structure 715 of the second cable 710 and the supporting structure 772 of the second connector 765 are the same structure (i.e., the supporting structure is continuous), which thus creates a monolithic cable. In alternative embodiments, the supporting structure 715 of the second cable 710 and the supporting structure 772 of the second connector 765 are different structures but are connected such that there is an electrical connection between the conductive traces 720, wiring layer 732, the electrodes 730, the conductive traces 773, and the contacts 775.

In various embodiments, the one or more conductive traces 774 are a plurality of traces, for example, two or more conductive traces or from two to twenty-four conductive traces. In some embodiments, at least one trace of the one or more conductive traces 774 terminates at a contact 775 exposed on the outside surface the supporting structure 772. In alternative embodiments, each trace from the one or more conductive traces 774 terminates at a contact 775 exposed on the outside surface the supporting structure 772. As should be understood, in some embodiments, each electrode from the electrodes 730 is electrically connected via a corresponding wiring layer 732, optional contact, conductive trace 720, and conductive trace 774, to a respective contact 775. In other words, each electrode may be electrically connected to a different contact (a one to one relationship). In alternative embodiments, a multiplexer chip may be used such that one or more electrodes from the electrodes 730 is electrically connected via wiring layer 732, optional contact, a conductive trace 720, and conductive trace 774, to a single contact 775. In other words, each electrode may be electrically connected to a same or different contact (a many to one relationship).

The one or more conductive traces 774 may be deposited onto a layer of the supporting structure 772 by using thin film deposition techniques well known to those skilled in the art such as by sputter deposition, chemical vapor deposition, metal organic chemical vapor deposition, electroplating, electroless plating, and the like. In some embodiments, the thickness of the one or more conductive traces 774 is dependent on the particular impedance desired for conductor, in order to ensure excellent signal integrity (e.g., electrical signal integrity for stimulation or recording). For example, if a conductor having a relatively high impedance is desired, a small thickness of conductive material should be deposited onto a layer of the supporting structure 772. If, however, a signal plane having a relatively low impedance is desired, a greater thickness of electrically conductive material should be deposited onto a layer of the supporting structure 772. In certain embodiments, each of the one or more conductive traces 774 has a thickness (t). In some embodiments, the thickness (t) is from 0.5 µm to 25 µm or from 5 µm to 10 µm, for example about 5 µm or about 8 µm. In some embodiments, each of the one or more conductive traces 774 has a length (l) of about 1 mm to 100 mm or 1 cm to 3 cm, e.g., about 15 mm. In some embodiments, each of the one or more conductive traces 774 has a width (w) from 2.0 µm to 500 µm, for example about 30 µm or about 50 µm.

As shown in FIGS. 7D and 7F, the second connector 765 may be formed with the predetermined shape or profile 773. The predetermined shape or profile 773 acts essentially as a key to assist with alignment in insertion of the second connector 765 into the first connector 760. In some embodiments, the predetermined shape or profile 773 is a blade with the inlaid supporting structure 772 folded over the core 770 creating a first planar sector 777 of contacts 775 positioned on a first side of the blade and a second planar sector 778 of contacts 775 positioned on a second side of the blade. In various embodiments, the contacts 775 are formed from split rows of conductive material positioned in columns and exposed on the surface 779 of the supporting structure 772. Each split row may be spaced apart from one another on the surface 779 of the supporting structure 772 by a region 780 of a top layer of the dielectric material. A width or pitch (p) of the region 780 of the top layer of the dielectric material that separates each split row may be between 0.1 mm to 10 mm, for example about 1.0 mm. In some embodiments, each portion of the split row connects to a single trace from the conductive traces 774. In other embodiments, each portion of the split row connects to two or more traces from the conductive traces 774. For example, a left side portion of the split row in first planar sector 777 may be connected with a first trace and a right side portion of the split row in the second planar sector 778 may be connected with a second trace. Alternatively, a multiplexer chip may be used to drive signals and thus the portions of the split row may be connected to multiple traces from the conductive traces 774. In various embodiments, thirty-two split rows are positioned on the supporting structure 772 of the second connector 765 and exposed on the surface 779; however, it should be understood that more or less than thirty-two split rows may be positioned on the supporting structure 772. For example, the supporting structure 772 may have an increased surface area to accommodate more rows of contacts 775 and enhance design flexibility for the second connector 765. Additionally, the rows may have one split (to isolate columns of contact regions); however, it should be understood that more than one split can be used. For example, the rows may have an increased number of splits (2, 3, 4, 5, 6, etc.) to enhance design flexibility for the second connector 765.

In various embodiments, the fist connector 760 further comprises one or more alignment holes 782 and the second connector 765 further comprises one or more alignment holes 783 (see, e.g., FIG. 7D). The alignment holes 782 and 783 are structured to align and assist with maintaining electrical contact between the contacts 769 of the first connector 760 and corresponding contacts 775 of the second connector 765. In some embodiments, the one or more attachment features 755 hold the first connector 760 in physical contact with the second connector 765 such that the contacts 769 are in electrical contact with the contacts 775. For example, the alignment holes 782 and 783 fit over the alignment pins 746, and thus hold the contacts 769 and corresponding contacts 775 in alignment. Moreover, the first compliant pad 748 and the second compliant pad 752 have a spring force that exerts a clasping pressure on the supporting structure 767 to electrically connect the first connector 760 with the second connector 765, as shown in FIG. 7C. The thin-film thickness (g) of the supporting structure 767 allows for the spring force of first compliant pad 748 and the second compliant pad 752 to be distributed across all electrical connections of contacts 769 and corresponding contacts 775 as well as for compliance during closing of the housing 737.

Figure 8A:
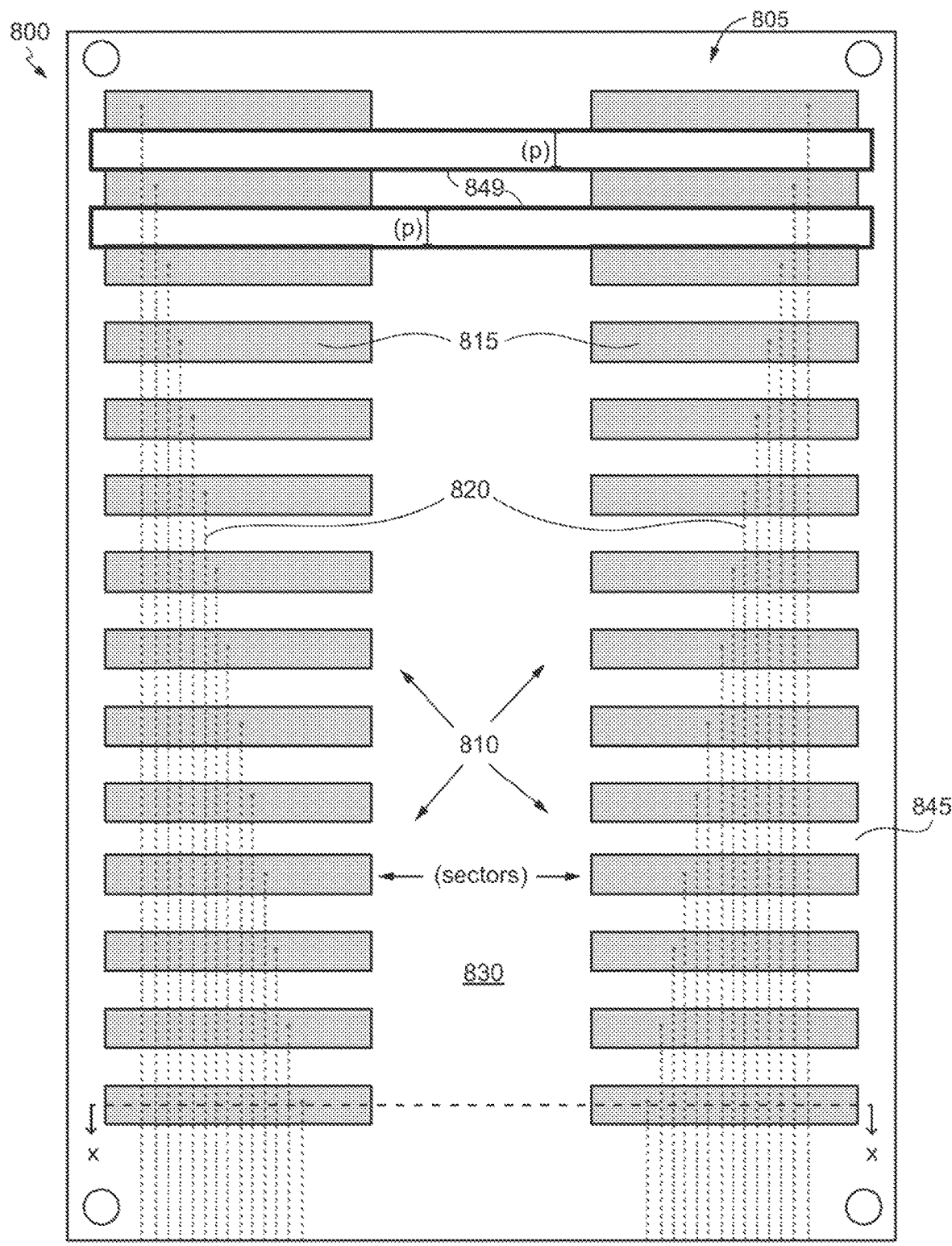
FIGS. 8A-8F show a top view, a bottom view, and cross-sectional side views illustrating a design and method of fabricating a first portion of a connection assembly in accordance with various embodiments.
Figure 8B:
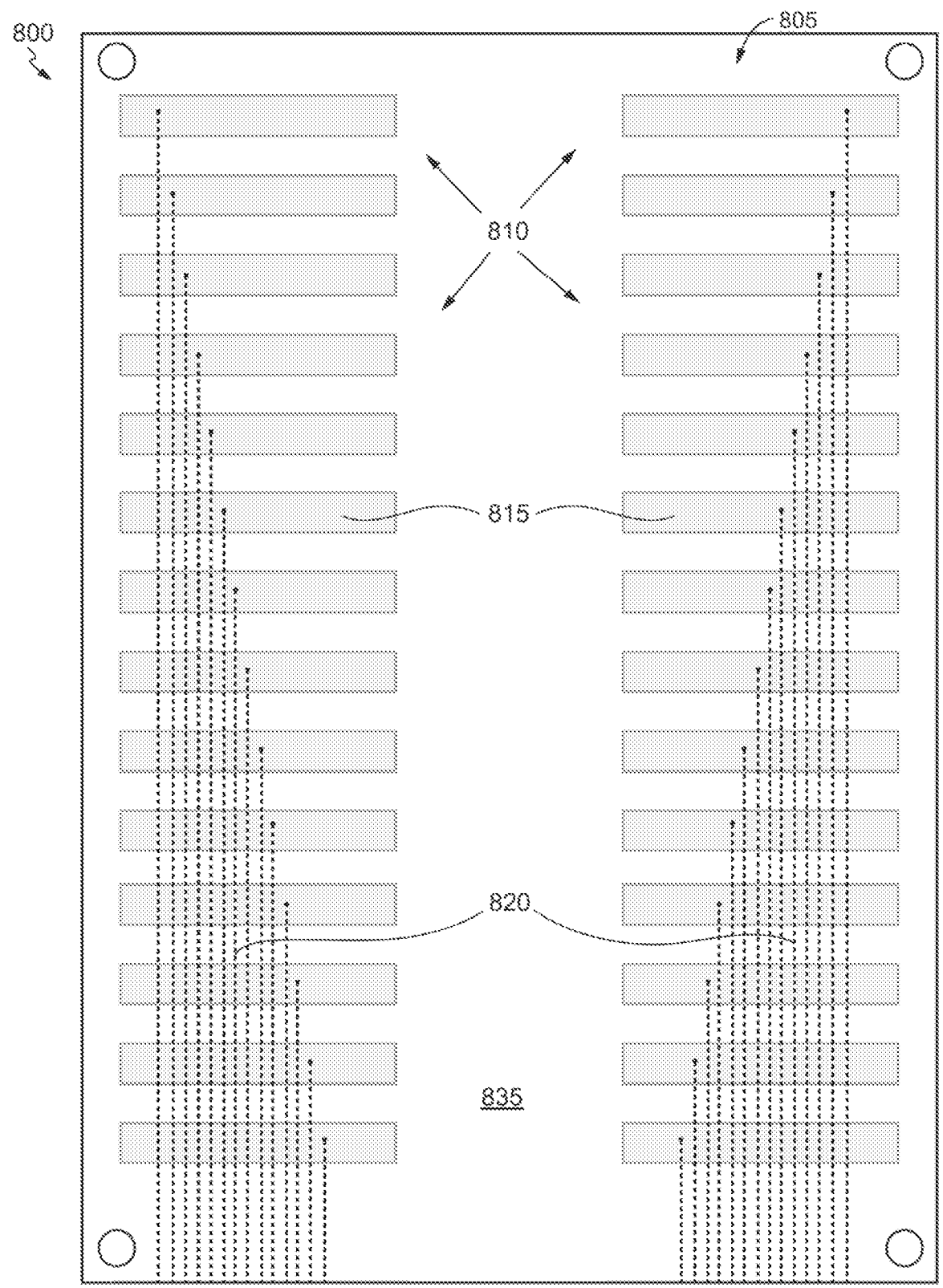
Figure 8C:
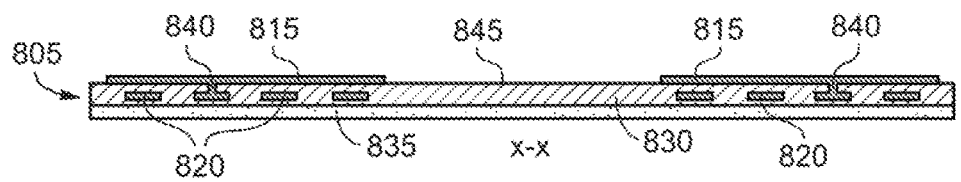

As shown in FIGS. 8A, 8B, and 8C, a first connector 800 (e.g., the connector 760 as discussed with respect to FIGS. 7A-7G) may be formed of a supporting structure 805 with a predetermined layout 810 of contacts 815 and conductive traces 820. In some embodiments, the supporting structure 805 is made of one or more layers of dielectric material formed on a substrate. The substrate may be made from any type of metallic or non-metallic material such as polyimide, liquid crystal polymer, parylene, polyether ether ketone, polyurethane, TPU, metal, or a combination thereof. As shown in FIG. 8C (cross-section of the connector 800 along X-X from FIGS. 8A and 8B), the supporting structure 805 may comprise a first layer of dielectric material 830 and a second layer of dielectric material 835 with the conductive traces 820 buried between the first layer of dielectric material 830 and the second layer of dielectric material 835. In some embodiments, the first layer of dielectric material 830 comprises at least one contact via 840 for each contact 815. The contact via 840 may comprise a conductive material for electrically connecting each contact 815 to at least one trace of the conductive traces 820 such that each trace of the conductive traces 820 terminates at a contact 815. The contact via 840 may be connected to the at least one trace of the conductive traces 820 directly or indirectly by way of a wiring layer (not shown). In some embodiments, the conductive material is lined on at least a portion of the walls of the via hole. In other embodiments, the conductive material fills the via hole.

In various embodiments, the contacts 815 are provided as split rows positioned in columns on sectors or faces of the supporting structure 805 (see, e.g., FIGS. 8A and 8B). In some embodiments, the contacts 815 are exposed on the surface 845 of the supporting structure 805 (see, e.g., FIG. 8C). For example, the contacts 815 may be raised above a surface of the supporting structure 805 (e.g., a top surface of the contacts 815 protrudes above a top surface of the supporting structure 805) and comprise an anti-abrasive finish. In certain embodiments, the contacts 815 are raised above the surface 845 of the supporting structure 805 by a predetermined distance. The predetermined distance is from 0.05 mm to 1.0 mm, for example about 0.5 mm. Moreover, each split row may be spaced apart from one another on the surface 845 of the supporting structure by a region 849 of the first layer of the dielectric material 830. A width or pitch (p) of the region 849 of the first layer of the dielectric material 830 that separates each split row may be between 1.0 mm to 10 mm, for example about 1 mm. In some embodiments, each contact 815 of a split row connects to a single trace of the conductive traces 820. In other embodiments, each contact 815 of a split row connects to two or more traces from the conductive traces 820. For example, a left side of the split row may be connected with a first trace and a right side of the split row may be connected with a second trace. Alternatively, a multiplexer chip may be used to drive signals and thus the split row may be connected to multiple traces from the conductive traces 820. In various embodiments, thirty-two split rows are positioned on the supporting structure 805 and exposed on the surface 845; however, it should be understood that more or less than thirty-two split rows can be positioned on the supporting structure 805. For example, the supporting structure 805 can accommodate more or less split rows (10, 24, 30, 42, 48, 50 etc.) to enhance design flexibility for the first connector 800.

Figure 8D:
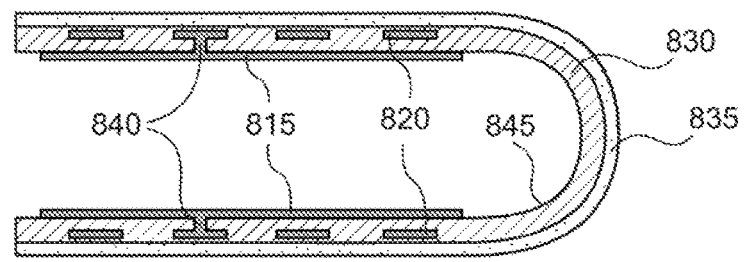
Figure 8E:
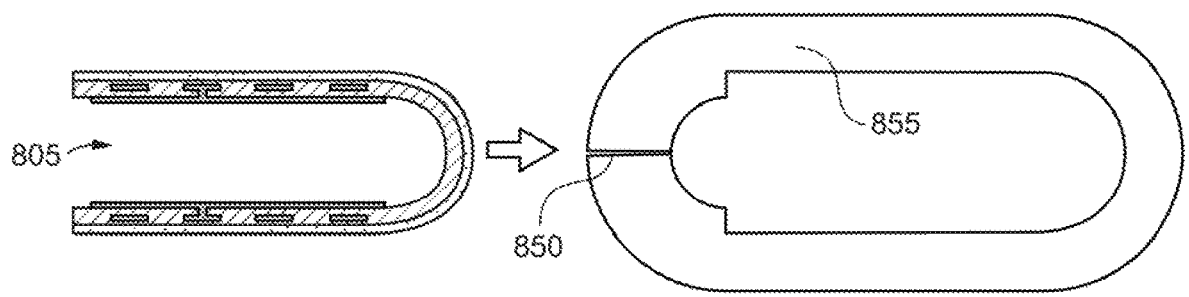
Figure 8F:
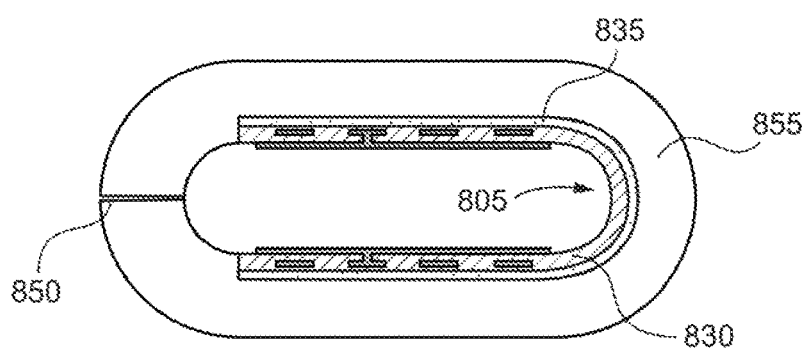

As shown in FIG. 8D, the supporting structure 805 may be shaped or folded such that the contacts 815 face inwardly. The supporting structure 805 may then be baked to thermoform the supporting structure 805 into a final shape, for example in a "U" shape. As shown in FIG. 8E, the supporting structure 805 may then be inserted into a pre-defined jacket 855 through a slot opening 850. In some embodiments, the jacket 855 is formed of a polymer material such as silicone. As shown in FIG. 8F, the supporting structure 805 and jacket 855 are reflowed at 130° C.-150° C. (e.g., 137C) using the second layer of dielectric material 835 or optionally the substrate 825 as an adhesive to attach the supporting structure 805 to the jacket 855. In some embodiments, the first layer of dielectric material 830 is a first type of polymer material, e.g., a high temperature liquid crystal polymer, that acts as an overlay for insulation, and the second layer of dielectric material 835 is a second type of polymer material, e.g., a low temperature liquid crystal polymer, that acts as the adhesive for bonding the supporting structure 805 to the jacket 855. In other embodiments, the first layer of dielectric material 830 and the second layer of dielectric material 835 are a first type of polymer material, e.g., a high temperature liquid crystal polymer, that acts as an overlay for insulation, and the substrate 825 is a second type of polymer material, e.g., a low temperature liquid crystal polymer, that acts as an adhesive for bonding the supporting structure 805 to the jacket 855, as shown in FIG. 8F. Although the first connector 800 is shown in FIG. 8D and described with respect to a "U" shape, it should be understood that other shapes for the connector have been contemplated, for example, spherical cubed, torus, ellipsoid, etc.

Figure 9A:
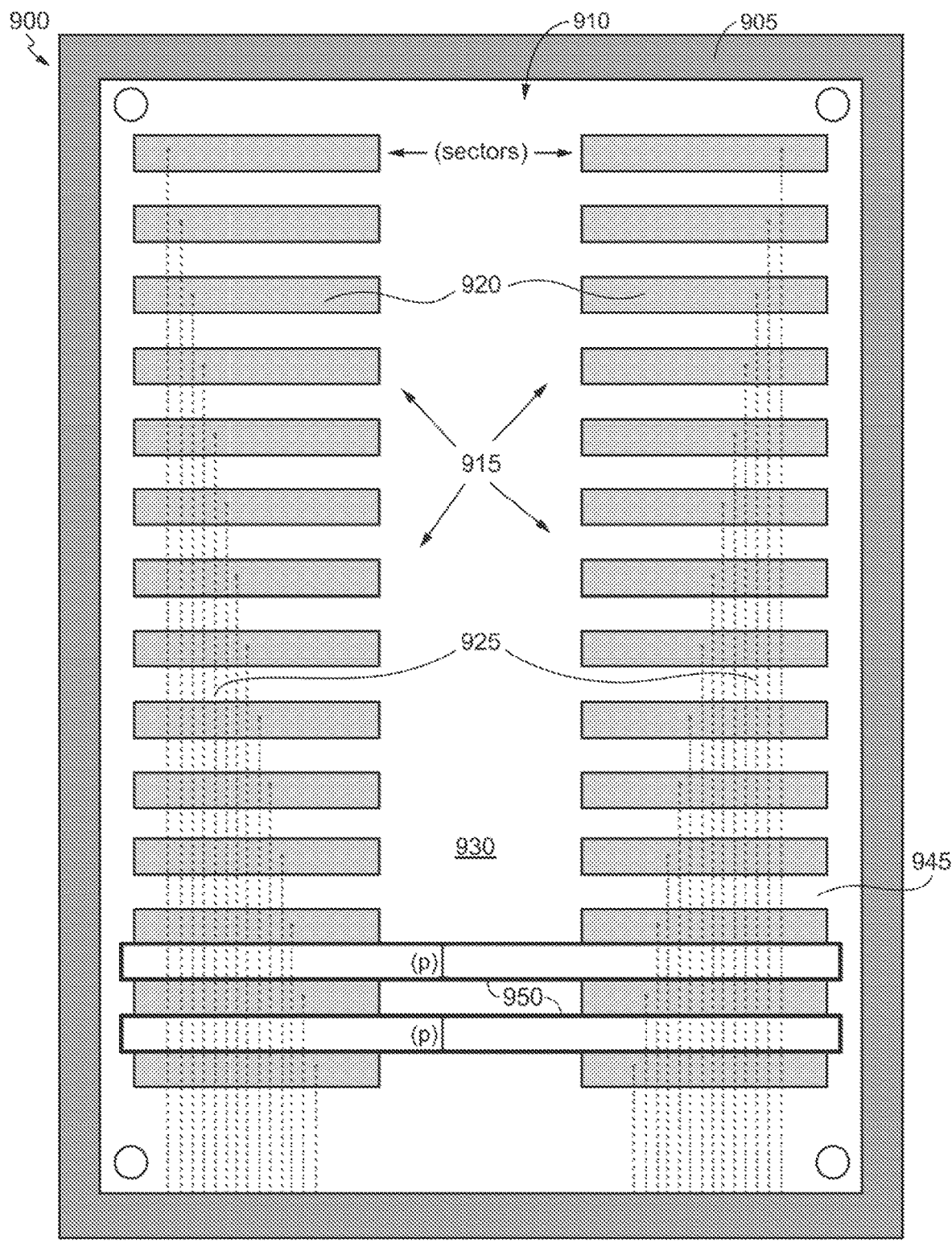
FIGS. 9A-9E show a top view, a bottom view, and cross-sectional side views illustrating a design and method of fabricating a second portion of a connection assembly in accordance with various embodiments.
Figure 9B:
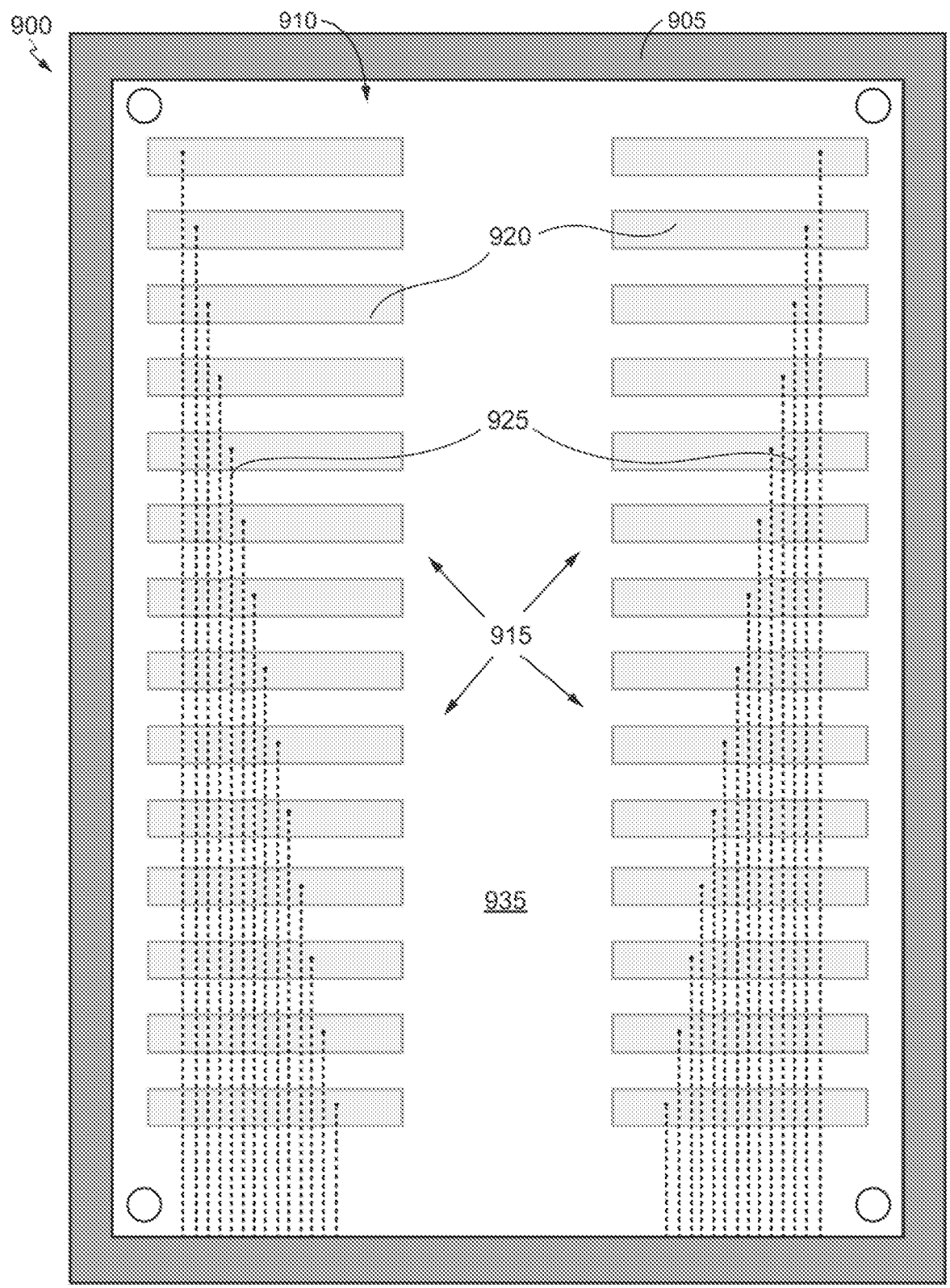
Figure 9C:
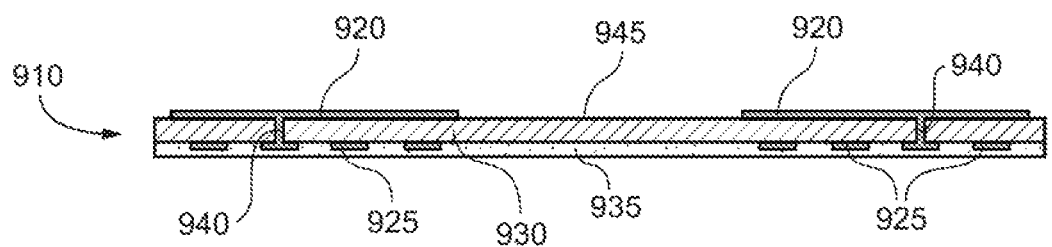

As shown in FIGS. 9A and 9B, the second connector 900 (e.g., the connector 765 as discussed with respect to FIGS. 7A-7G) may be formed of a core 905 and an inlaid supporting structure 910 with a predetermined layout 915 of contacts 920 and conductive traces 925. As shown in FIG. 9C (cross-section of the second connector 900 along X-X from FIGS. 9A and 9B), the supporting structure 910 may comprise a first layer of dielectric material 930 and a second layer of dielectric material 935 with the conductive traces 925 buried between the first layer of dielectric material 930 and the second layer of dielectric material 935. In some embodiments, the first layer of dielectric material 930 comprises at least one contact via 940 for each contact 920. The contact via 940 may comprise a conductive material for electrically connecting each contact 920 to at least one trace of the conductive traces 925 such that each trace of the conductive traces 925 terminates at a contact 920. The contact via 940 may be connected to the at least one trace of the conductive traces 925 directly or indirectly by way of a wiring layer (not shown). In some embodiments, the conductive material is lined on at least a portion of the walls of the via hole. In other embodiments, the conductive material fills the via hole.

In various embodiments, the contacts 920 are provided as split rows positioned in columns on sectors or faces of the supporting structure 910 (see, e.g., FIGS. 9A and 9B). In some embodiments, the contacts 920 are exposed on the surface 945 of the supporting structure 910 (see, e.g., FIG. 9C). For example, the contacts 920 may be raised above a surface of the supporting structure 910 (e.g., a top surface of the contacts 920 protrudes above a top surface of the supporting structure 910) and comprise an anti-abrasive finish. In certain embodiments, the contacts 920 are raised above the surface 945 of the supporting structure 910 by a predetermined distance. The predetermined distance is from 0.05 mm to 1.0 mm, for example about 0.5 mm. Moreover, each split row may be spaced apart from one another on the surface 945 of the supporting structure by a region 950 of the first layer of the dielectric material 930. A width or pitch (p) of the region 950 of the first layer of the dielectric material 930 that separates each split row may be between 1.0 mm to 10 mm, for example about 1 mm. In some embodiments, each contact 920 of a split row connects to a single trace of the conductive traces 925. In other embodiments, each contact 920 of a split row connects to two or more traces from the conductive traces 925. For example, a left side of the split row may be connected with a first trace and a right side of the split row may be connected with a second trace.

Alternatively, a multiplexer chip may be used to drive signals and thus the split row may be connected to multiple traces from the conductive traces 925. In various embodiments, thirty-two split rows are positioned on the supporting structure 910 and exposed on the surface 945; however, it should be understood that more or less than thirty-two split rows can be positioned on the supporting structure 910. For example, the supporting structure 910 can accommodate more or less split rows (10, 24, 30, 42, 48, 50 etc.) to enhance design flexibility for the second connector 900.

Figure 9D:
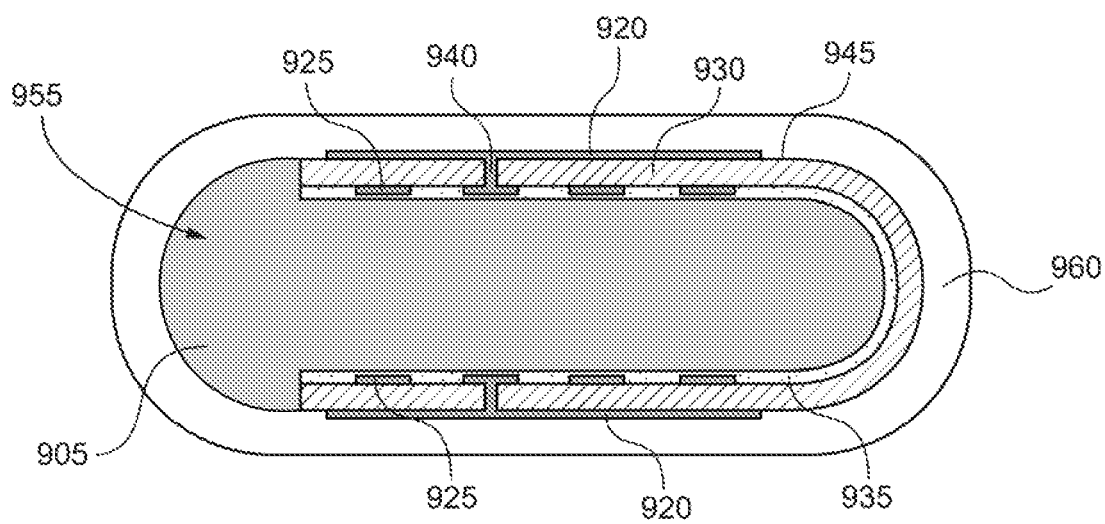

As shown in FIG. 9D, the supporting structure 910 may be shaped or folded on the core 905 (e.g., an injection molded core) such that the contacts 920 face outwardly. In various embodiments, the core 905 and the supporting structure 910 may be formed with a predetermined shape or profile 955 (e.g., a blade as shown in FIG. 9D). The predetermined shape or profile 955 acts essentially as a key to assist with alignment in insertion of the second connector 900 into the first connector 800. As shown in FIG. 9D, the shape or profile 955 comprises the one or more layers of dielectric material 930/935 at least partially wrapped around the core 905, e.g., a "U" shaped wrapping. The first layer of dielectric material 930 may define an outer width (n) of the shape or profile 955 and the second layer of dielectric material 935 may define an inner width (n') of the shape or profile 945. The shape or profile 955 may further comprise the core 905 that at least partially fills a space interior of the shape or profile 955 defined by the inner width (n') of the shape or profile 955. The core 905 may be comprised of one or more layers of material such that the core 905 has a Shore durometer of greater than 70D. In some embodiments, the one or more layers of material of the core 905 is polyimide, liquid crystal polymer, parylene, polyether ether ketone, polyurethane, metal, or a combination thereof. In certain embodiments, the one or more layers of material of the core 905 is a TPU. Although the second connector 900 is shown in FIG. 9D and described with respect to a blade shape, it should be understood that other shapes for the connector have been contemplated, for example, spherical cubed, torus, ellipsoid, etc.

Figure 9E:
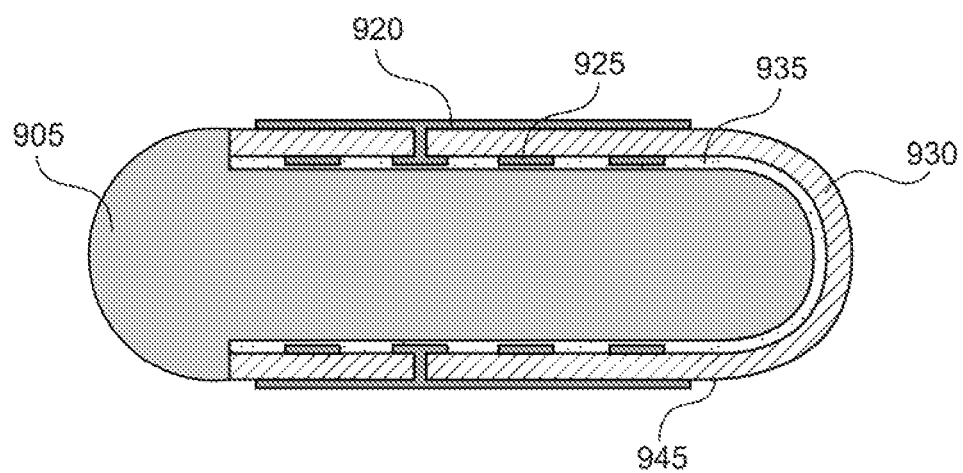

Once the core 905 and the supporting structure 910 are shaped, the core 905 and the supporting structure 910 may then be inserted into a heat shrink tube 960 (e.g., FEP Lay-Flat-m Heat Shrink) and baked to thermoform the core 905 and supporting structure 910 into a final shape, for example a blade, as shown in FIG. 9D. The core 905 and the supporting structure 910 may be reflowed at 130° C.-150° C. (e.g., 137° C.) using the second layer of dielectric material 935 as an adhesive to attach the core 905 to the supporting structure 910. In some embodiments, the first layer of dielectric material 930 is a first type of polymer material, e.g., a high temperature liquid crystal polymer, that acts as an overlay for insulation, and the second layer of dielectric material 935 is a second type of polymer material, e.g., a low temperature liquid crystal polymer, that acts as an adhesive for bonding the supporting structure 910 to the core 905, as shown in FIG. 9E.

VI. Multiplexor Connectors and Methods of Manufacture

Figure 10A:
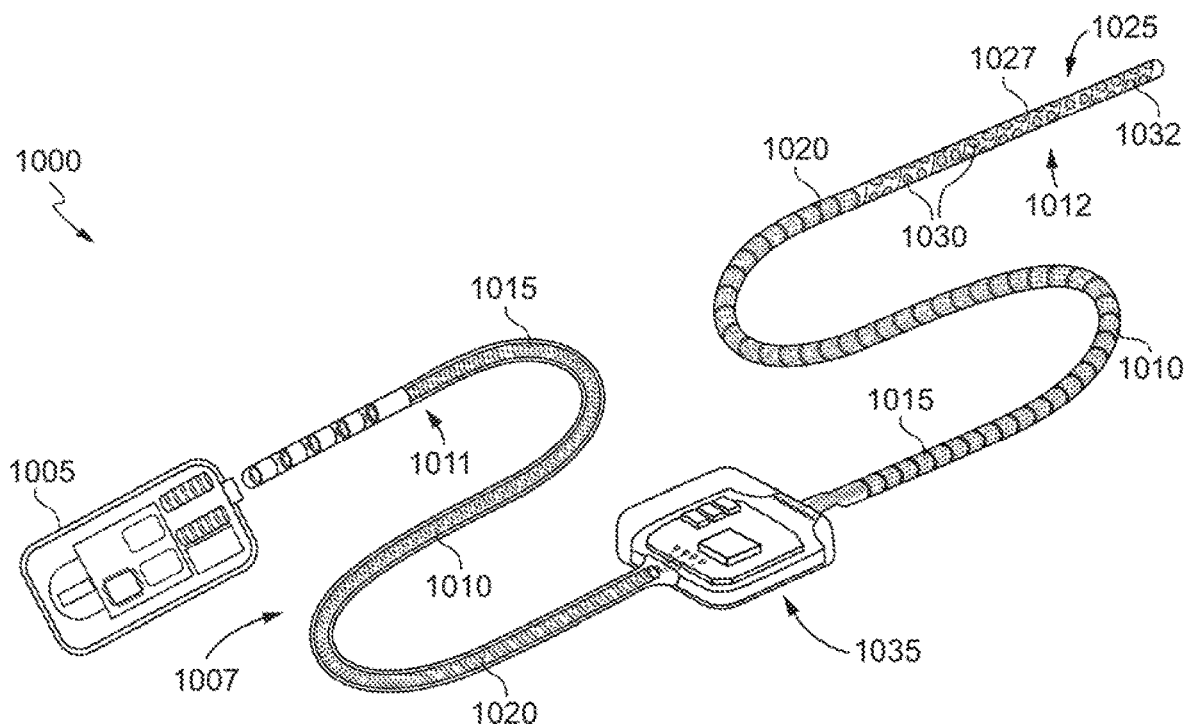
FIG. 10A shows a neuromodulation system in accordance with various embodiments.

FIG. 10A shows a neuromodulation system 1000 (e.g., the neuromodulation system 100 described with respect to FIG. 1) in accordance with aspects of the present disclosure. In various embodiments, the neuromodulation system 1000 comprises an implantable neurostimulator 1005 and a lead assembly 1007. The lead assembly 1007 includes two or more cables 1010, a proximal end 1011, and a distal end 1012. In some embodiments, the two or more cables 1010 comprise a high density cable and a low density cable. As used herein, "a high density cable" is a cable with more conductive traces than the "low density cable". For example, the "high density cable" may have at least sixteen conductive traces, and the "low density cable" may have anywhere from one to fifteen conductive traces. Each cable 1010 may comprise a supporting structure 1015 and a plurality of conductive traces 1020 formed on a portion of the supporting structure 1015. In some embodiments, the supporting structure 1015 is made of one or more layers of dielectric material (i.e., an insulator). The dielectric material may be selected from the group of electrically flexible nonconductive materials consisting of organic or inorganic polymers, polyimide-epoxy, epoxy-fiberglass, and the like. In certain embodiments, the dielectric material is a polymer of imide monomers (i.e., a polyimide), a liquid crystal polymer (LCP) such as Kevlar®, parylene, polyether ether ketone (PEEK), or combinations thereof. In other embodiments, the supporting structure 1015 is made of one or more layers of dielectric material formed on a substrate. The substrate may be made from any type of metallic or non-metallic material.

In various embodiments, the one or more conductive traces 1020 are a plurality of traces, for example, two or more conductive traces or from two to twenty-four conductive traces. The plurality of conductive traces 1020 are comprised of one or more layers of conductive material. The conductive material selected for the one or more conductive traces 1020 should have good electrical conductivity and may include pure metals, metal alloys, combinations of metals and dielectrics, and the like. For example, the conductive material may be platinum (Pt), platinum/iridium (Pt/Ir), titanium (Ti), gold/titanium (Au/Ti), or any alloy thereof. In some embodiments, it is also desirable that the conductive material selected for the one or more conductive traces 1020 have a CTE that is approximately equal to that of the CTE of the supporting structure 1015.

As shown in FIG. 10A, the lead assembly 1007 may further comprise an electrode assembly 1025 formed on a supporting structure 1027. The supporting structure 1027 may provide support for microelectronic structures including one or more electrodes 1030, a wiring layer 1032, and optional contact(s)(not shown). The electrode assembly 1025 may be located at the distal end 1012 of the lead assembly 1007. The one or more electrodes 1030 are in electrical connection with one or more conductive traces of the plurality of conductive traces 1020, for example, via the wiring layer 1032 and optionally the contact(s). In various embodiments, the supporting structure 1015 of at least one cable 1010 and the supporting structure 1027 of the electrode assembly 1025 are the same structure (i.e., the supporting structure is continuous), which thus creates a monolithic structure. In alternative embodiments, the supporting structure 1015 of at least one cable 1010 and the supporting structure 1027 of the electrode assembly 1025 are different structures but are connected such that there is an electrical connection between the plurality of conductive traces 1020, wiring layer 1032, and the one or more electrodes 1030.

Figure 10B:
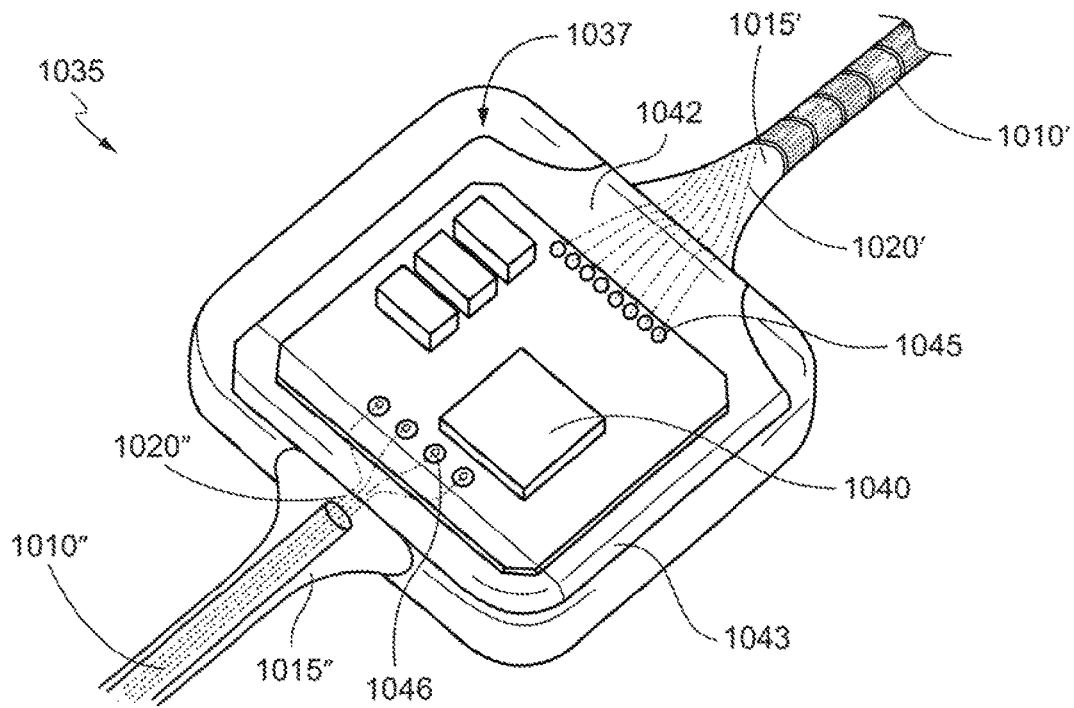
FIGS. 10B-10D show multiplexor connector in accordance with various embodiments.
Figure 10C:
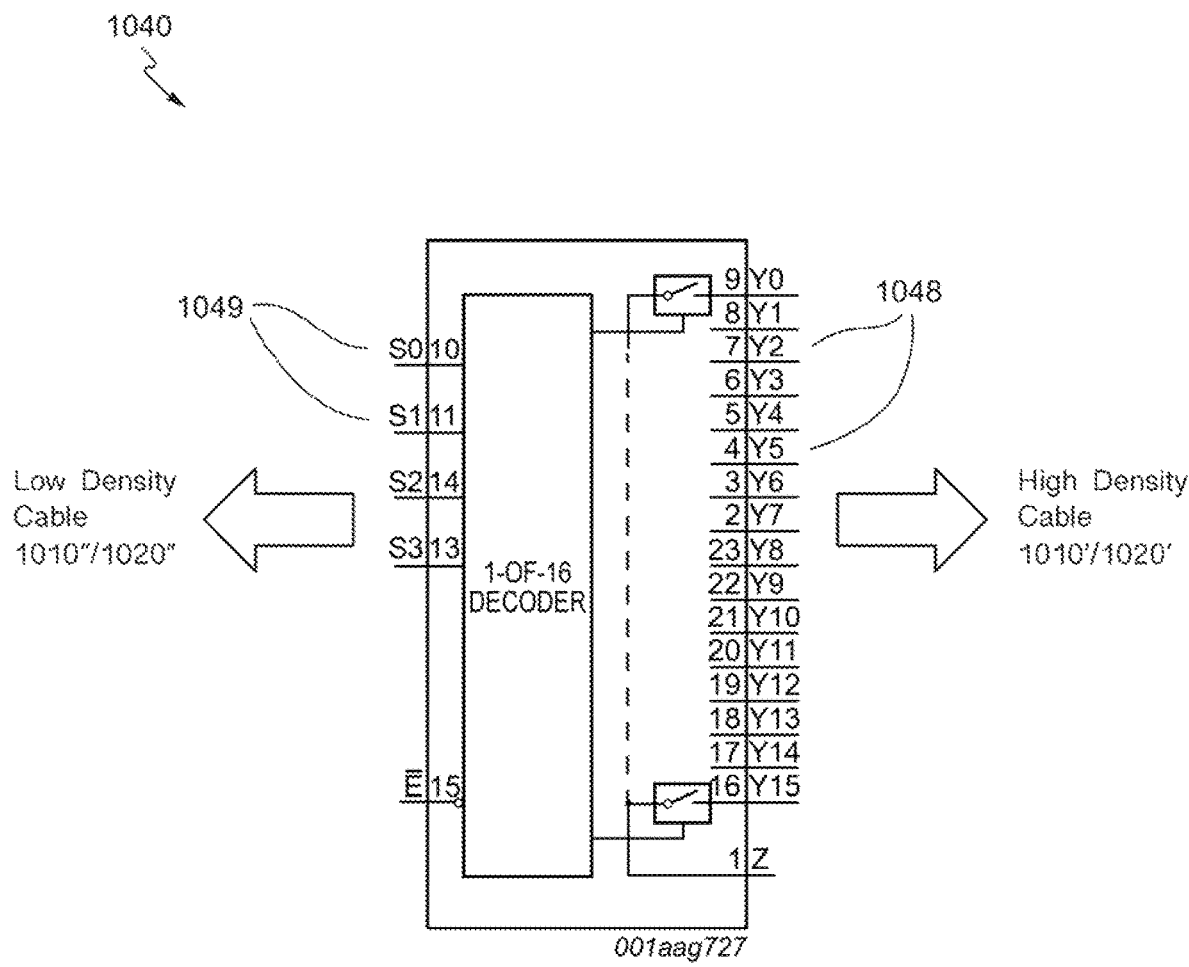

As shown in FIGS. 10A and 10B the lead assembly 1007 may further comprise one or more connectors 1035 for connecting the two or more cables 1010 to one or more multiplexor chips 1040. Each connector 1035 comprises a package 1037, the one or more multiplexor chips 1040, and a connection assembly 1042. In various embodiments, the package 1037 comprises a housing 1043, the one or more multiplexor chips 1040, distal feedthroughs 1045, and proximal feedthroughs 1046, as shown in FIG. 10B. In some embodiments, the multiplexer chips 1040 and other active/passive electronic components are hermetically sealed within the package 1037 with distal feedthroughs 1045 and proximal feedthroughs 1046 (e.g., vertical feedthroughs). The distal feedthroughs 1045 are contact vias comprising a conductive material for electrically connecting the conductive traces or channels 1020' from a high density distal cable 1010' (e.g., the cable connected to the electrode assembly) to distal channel inputs 1048 of the multiplexor chips 1040, respectively, as shown in FIGS. 10B and 10C. The proximal feedthroughs 1046 are contact vias comprising a conductive material for electrically connecting the conductive traces or channels 1020" from a low density proximal cable 1010" (e.g., the cable connected to the neurostimulator) to proximal channel inputs 1049 of the multiplexor chips 1040, respectively, as shown in FIGS. 10B and 10C. As shown in FIG. 10C, a multiplexor chip 1040 may be used in the package 1037 to reduce the channel count of the high density distal cable 1010' from a greater number (e.g., 16, 32, 40, etc.) to a lower channel count (e.g., 4, 8, 12, etc.) of the low density cable 1010". The channel count of the high density distal cable 1010' and/or the low density proximal cable 1010" may be expanded by adding more multiplexor ships 1040 to the package 1037 or more connectors 1035 to the lead assembly 1007.

Figure 10D:
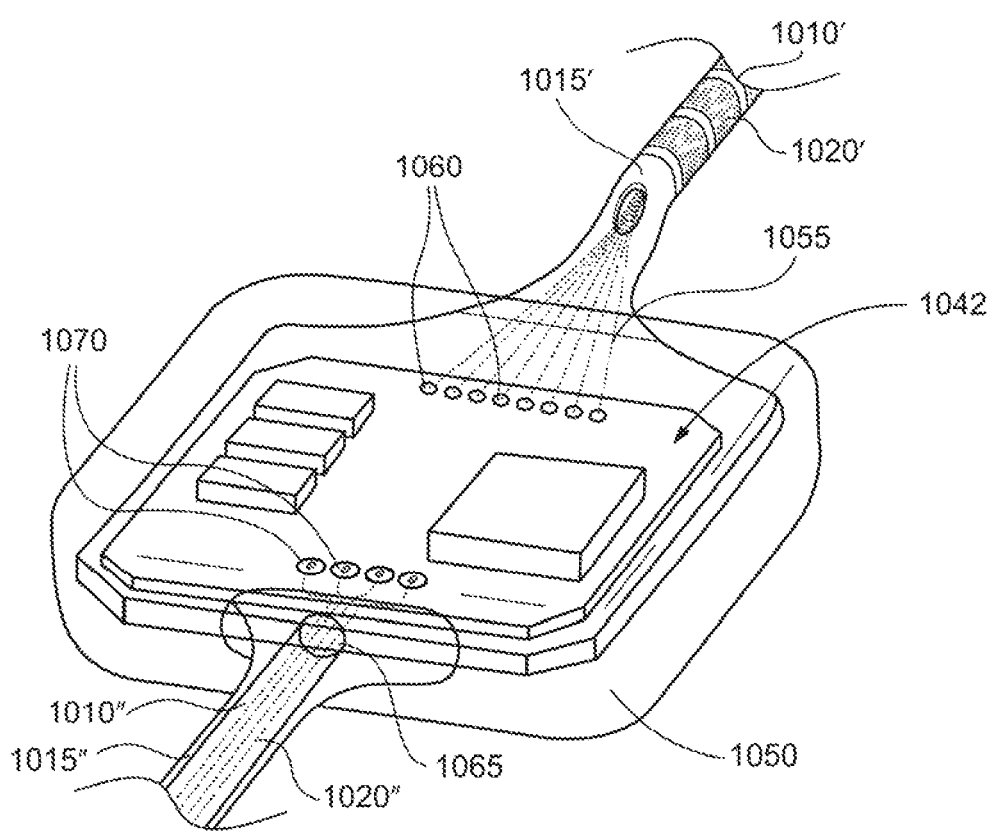

In various embodiments, the connection assembly 1042 comprises a supporting structure 1050, as shown in FIG. 10D. In some embodiments, the supporting structure 1050 is comprised of one or more layers of dielectric material (i.e., an insulator). The layers of dielectric material of the supporting structure 1050 may be formed in a FPCB process with metallization layers (e.g., vias or wiring layers) for interconnection. In other embodiments, the supporting structure 1050 is made of one or more layers of dielectric material and a coating of a thin layer of a polymer such as TPU. The dielectric material of the supporting structure 1050 may be selected from the group of electrically flexible nonconductive materials consisting of organic or inorganic polymers, polyimide-epoxy, epoxy-fiberglass, and the like. In certain embodiments, the dielectric material is a polymer of imide monomers (i.e., a polyimide), a liquid crystal polymer (LCP) such as Kevlar®, parylene, polyether ether ketone (PEEK), or combinations thereof.

In some embodiments, distal conductive traces 1055 and distal contacts 1060 (i.e., electrically conductive elements, pins, wires, tabs, pads, etc.) are formed on the supporting structure 1050 (see, e.g., FIG. 10D). In some embodiments, proximal conductive traces 1065 and proximal contacts 1070 (i.e., electrically conductive elements, pins, wires, tabs, pads, etc.) are formed on the supporting structure 1050 (see, e.g., FIG. 10D). The conductive traces 1055/1065 and contacts 1060/1070 may be comprised of one or more layers of conductive material for electrical conductivity. The conductive material selected for the conductive traces 1055/1065 and contacts 1060/1070 should have good electrical conductivity and may include pure metals, metal alloys, combinations of metals and dielectrics, and the like. For example, the conductive material may be platinum (Pt), platinum/iridium (P/Ir), titanium (Ti), gold/titanium (Au/Ti), or any alloy thereof. In some embodiments, it is also desirable that the conductive material selected for the conductive traces 1055/1065 and contacts 1060/1070 have a CTE that is approximately equal to that of a CTE of the supporting structure 1050. In some embodiments, the supporting structure 1015' of the distal cable 1010' and the supporting structure 1050 of the connection assembly 1042 are the same structure (i.e., the supporting structure is continuous), which thus creates a monolithic cable. In alternative embodiments, the supporting structure 1015' of the distal cable 1010' and the supporting structure 1050 of the connection assembly 1042 are different structures but are connected such that there is an electrical connection between the conductive traces 1020', the conductive traces 1055, and the contacts 1060. In some embodiments, the supporting structure 1015" of the proximal cable 1010" and the supporting structure 1050 of the connection assembly 1042 are the same structure (i.e., the supporting structure is continuous), which thus creates a monolithic cable. In alternative embodiments, the supporting structure 1015 of the proximal cable 1010" and the supporting structure 1050 of the connection assembly 1042 are different structures but are connected such that there is an electrical connection between the conductive traces 1020", the conductive traces 1065, and the contacts 1070.

In various embodiments, each trace from the one or more conductive traces 1055 terminates at a contact 1060 exposed on the outside surface of the supporting structure 1050. Each contact from the one or more contacts 1060 is electrically connected to a distal feedthrough 1045. As should be understood, each electrode from the electrodes 1030 is electrically connected via at least corresponding wiring layer 1032, optional contact, conductive trace 1020', conductive trace 1055, contact 1060, and distal feedthrough 1045 to a respective distal channel input 1048. In other words, each electrode may be electrically connected to the multiplexer chip 1040. Additionally, each trace from the one or more conductive traces 1065 terminates at a contact 1070 exposed on the outside surface the supporting structure 1050. Each contact from the one or more contacts 1070 is electrically connected to a proximal feedthrough 1046. As should be understood, the neurostimulator (e.g., the electronics module) is electrically connected via at least conductive trace 1020", conductive trace 1065, contact 1070, and proximal feedthrough 1046 to a respective proximal channel input 1049. In other words, the neurostimulator may be electrically connected to the multiplexer chip 1040. Consequently, a high density number of electrodes 1030 may be connected via the multiplexer chip 1040 to a neurostimulator with a reduced or limited number of channels for sending and receiving input to and from the electrodes 1030.

The one or more conductive traces 1055/1065 may be deposited onto a layer of the supporting structure 1050 by using thin film deposition techniques well known to those skilled in the art such as by sputter deposition, chemical vapor deposition, metal organic chemical vapor deposition, electroplating, electroless plating, and the like. In some embodiments, the thickness of the one or more conductive traces 1055/1065 is dependent on the particular impedance desired for conductor, in order to ensure excellent signal integrity (e.g., electrical signal integrity for stimulation or recording). For example, if a conductor having a relatively high impedance is desired, a small thickness of conductive material should be deposited onto a layer of the supporting structure 1050. If, however, a signal plane having a relatively low impedance is desired, a greater thickness of electrically conductive material should be deposited onto a layer of the supporting structure 1050. In certain embodiments, each of the one or more conductive traces 1055/1065 has a thickness (t). In some embodiments, the thickness (t) is from 0.5 µm to 25 µm or from 5 µm to 10 µm, for example about 5 µm or about 8 µm. In some embodiments, each of the one or more conductive traces 1055/1065 has a length (l) of about 1 mm to 100 mm or 1 cm to 3 cm, e.g., about 15 mm. In some embodiments, each of the one or more conductive traces 1055/1065 has a width (w) from 2.0 µm to 500 µm, for example about 30 µm or about 50 µm.

Figure 11A:
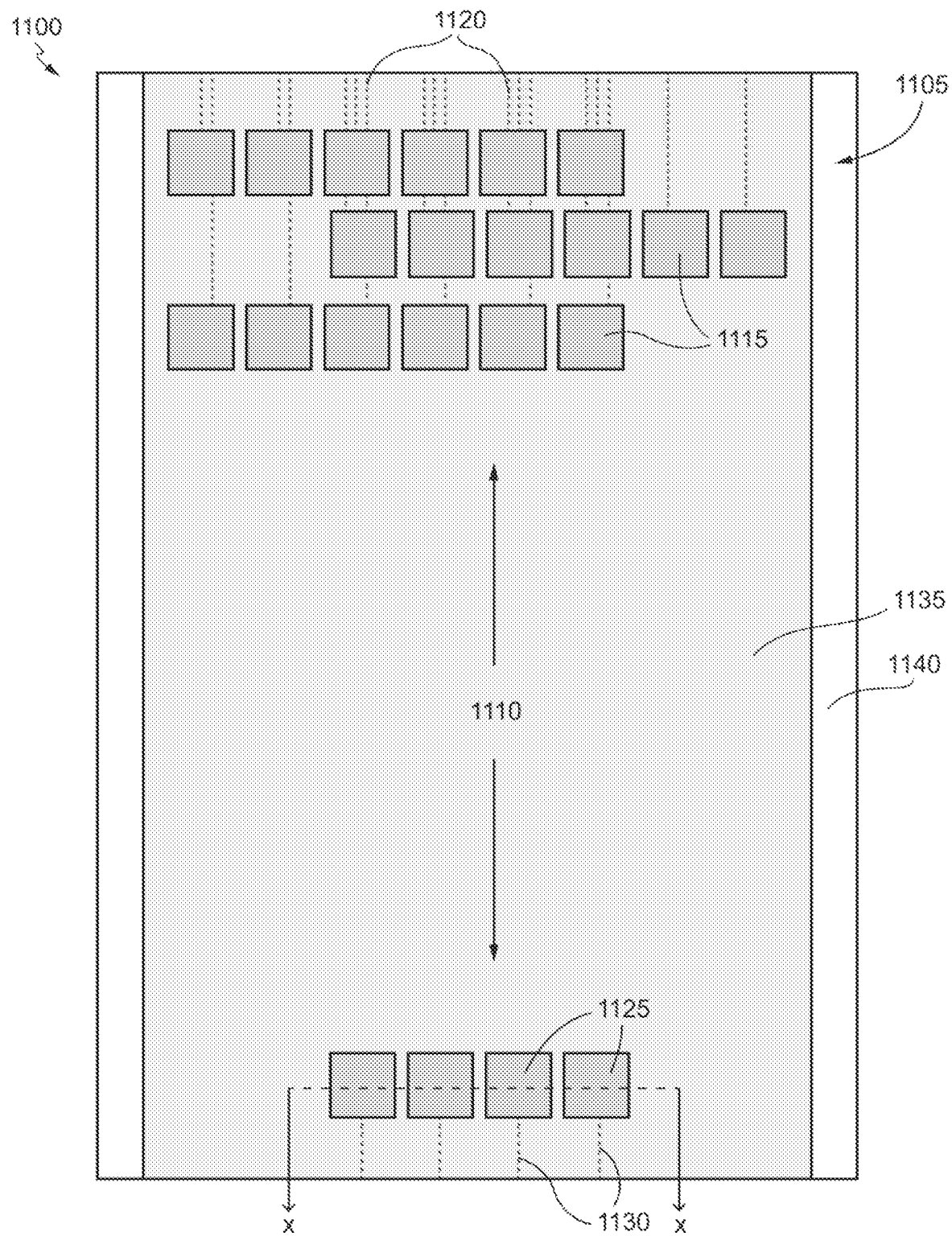
FIGS. 11A-11D show a top view, a bottom view, and cross-sectional side views illustrating a design and method of fabricating a header in accordance with various embodiments.
Figure 11B:
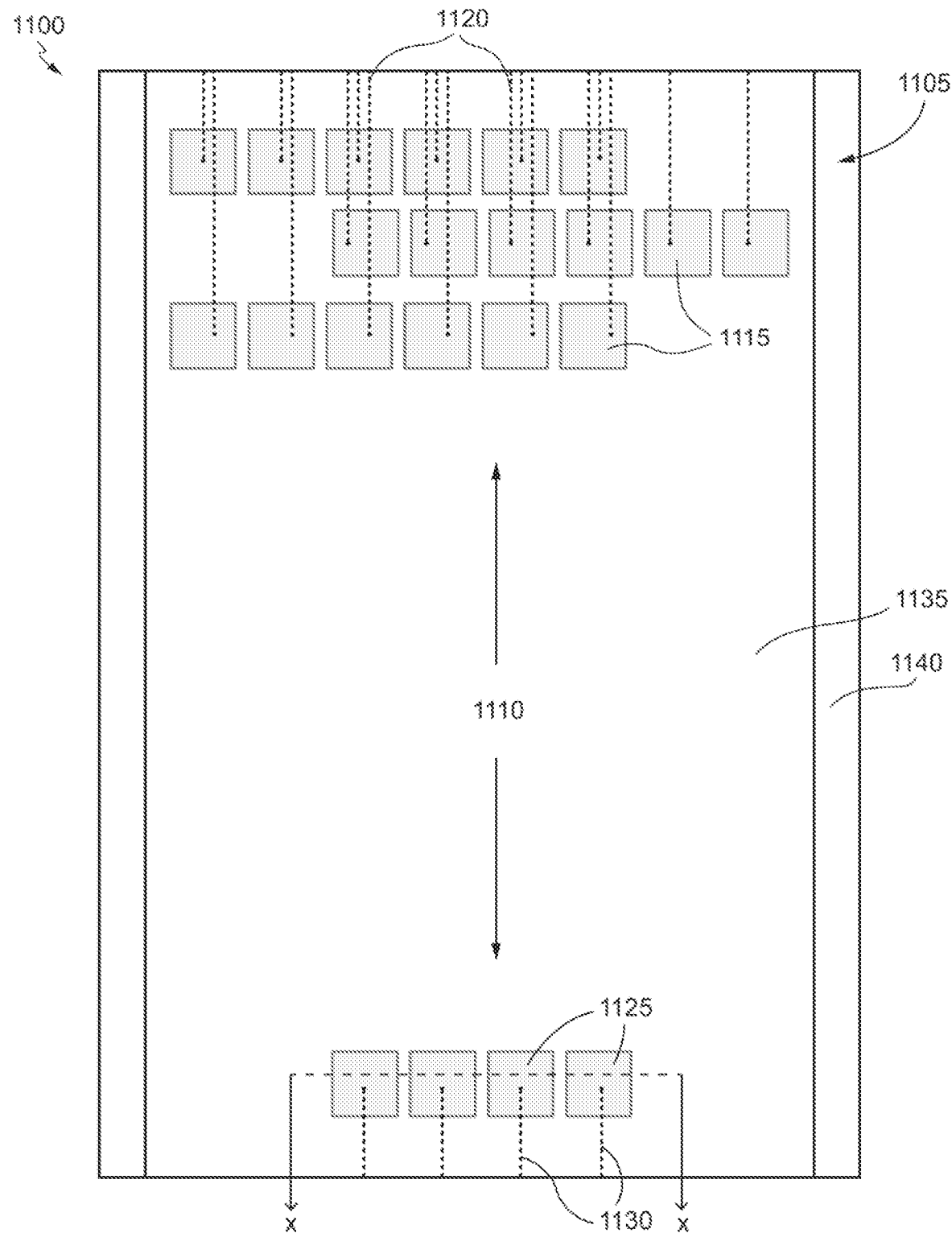
Figure 11C:
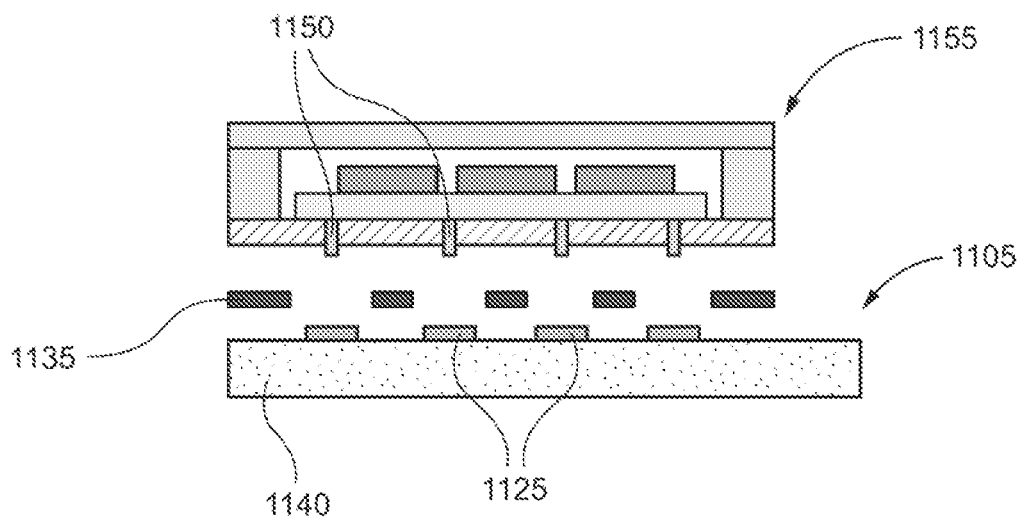

As shown in FIGS. 11A and 11B, a connection assembly 1100 (e.g., the connection assembly 1042 as discussed with respect to FIGS. 10A-10D) may be formed of a supporting structure 1105 with a predetermined layout 1110 of distal contacts 1115, distal conductive traces 1120, proximal contacts 1125, and proximal conductive traces 1130. As shown in FIG. 11C (cross-section of the connection assembly 1100 along X-X from FIGS. 11A and 11B), the supporting structure 1105 may comprise a first layer of dielectric material 1135 and a second layer of dielectric material 1140 with the distal contacts 1115, the distal conductive traces 1120, the proximal contacts 1125, and the proximal conductive traces 1130 disposed between the first layer of dielectric material 1135 and the second layer of dielectric material 1140. For example, a pre-cut first layer of dielectric material 1135 may be formed over the second layer of dielectric material 1140 such that at least a portion of each of the distal contacts 1115 and the proximal contacts are exposed after reflow of the first layer of dielectric material 1135. The distal contacts 1115 and proximal contacts 1125 are provided on the second layer of dielectric material 1140 in the predetermined layout 1110 to provide electrical contact with the distal feedthroughs (not shown) and proximal feedthroughs 1150 of a multiplexer chip package 1155, respectively.

Figure 11D:
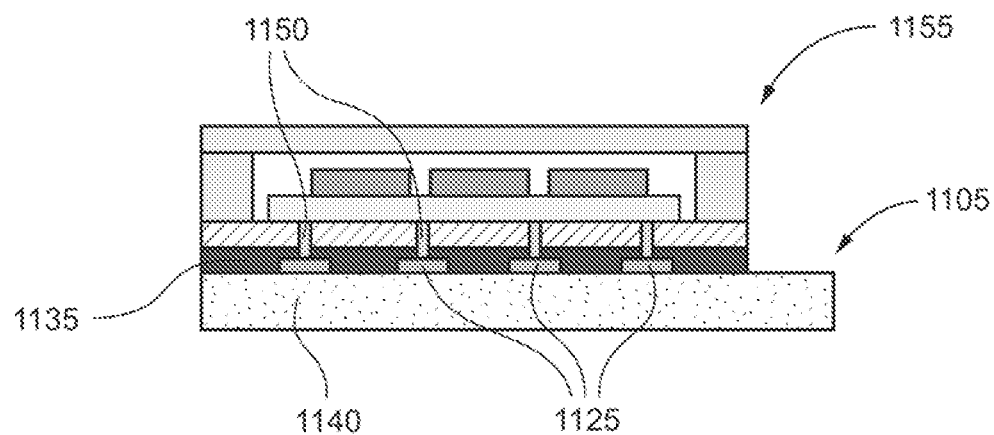

Once the distal contacts 1115, distal conductive traces 1120, proximal contacts 1125, and proximal conductive traces 1130 are formed on the supporting structure 1105 and the first layer of dielectric material 1135 is positioned over the second layer of dielectric material 1140, the supporting structure 1105 and the multiplexer chip package 1155 may then baked to thermoform the supporting structure 1105 into a final shape attached to the multiplexer chip package 1055, as shown in FIG. 11D. The supporting structure 1105 may be reflowed at 130° C.-150° C. (e.g., 137° C.) using the first layer of dielectric material 1135 as an adhesive to attach the supporting structure 1105 to the multiplexer chip package 1055. During bonding, each of the distal feedthroughs 1115 and proximal feedthroughs 1050 is compressed against respective distal contacts 1115 and proximal contacts 1125 to form the electrical connection. Under heat and pressure, the first layer of dielectric material 1135 melts, deforms and reflows to seal the gaps. In some embodiments, the first layer of dielectric material 1135 is a first type of polymer material, e.g., a low temperature liquid crystal polymer, that acts as an adhesive for bonding the supporting structure 1105 to the core, and the second layer of dielectric material 1140 is a second type of polymer material, e.g., a high temperature liquid crystal polymer, that acts as an overlay for insulation, as shown in FIG. 11D.

Advantageously, the low temperature liquid crystal polymer is used for adhesiveless bonding and encapsulation, to eliminate the needs of conductive paste or solder. Moreover, the use of low temperature liquid crystal polymer adhesiveless bonding is also a long-term solution to prevent degradation of adhesive and electrical crosstalk.

While the connectors have been described at some length and with some particularity with respect to a specific design and/or performance need, it is not intended that the connectors be limited to any such particular design and/or performance need. Instead, it should be understood the connectors described herein are exemplary embodiments, and that the connectors are to be construed with the broadest sense to include variations of the specific design and/or performance need described herein, as well as other variations that are well known to those of skill in the art. In particular, the shape and location of components and layers in the connectors may be adjusted or modified to meet specific design and/or performance needs. Furthermore, it is to be understood that other structures have been omitted from the description of the connectors for clarity. The omitted structures may include insulating layers, interconnect components, passive devices, etc.

While the invention has been described in detail, modifications within the spirit and scope of the invention will be readily apparent to the skilled artisan. It should be understood that aspects of the invention and portions of various embodiments and various features recited above and/or in the appended claims may be combined or interchanged either in whole or in part. In the foregoing descriptions of the various embodiments, those embodiments which refer to another embodiment may be appropriately combined with other embodiments as will be appreciated by the skilled artisan. Furthermore, the skilled artisan will appreciate that the foregoing description is by way of example only, and is not intended to limit the invention.

What is claimed is:

1. A lead assembly comprising:
   a cable comprising a proximal end, a distal end, and first conductive traces;
   a connector comprising a core and a supporting structure wrapped around at least a portion of the core, wherein:
   the connector is located at the proximal end of the cable;
   the supporting structure comprises a first layer of dielectric material and a second layer of dielectric material;
   the first layer of dielectric material is a high temperature liquid crystal polymer;
   the second layer of dielectric material is a low temperature liquid crystal polymer that is reflowed to attach the supporting structure to the core;
   second conductive traces are buried between the first layer of dielectric material and the second layer of dielectric material;
   the second conductive traces terminate at conductive contacts formed on a surface of the first layer of dielectric material; and
   the connector has a predetermined shape or profile, which facilitates alignment and insertion of the connector into a header; and
   an electrode assembly located at the distal end of the cable, the electrode assembly comprising electrodes electrically connected to the conductive contacts via the first conductive traces and the second conductive traces.

2. The lead assembly of claim 1, wherein the connector further comprises a sealing feature, which is a section of the predetermined shape or profile at a distal end of the connector, and the sealing feature comprises a different material, texture, or stiffness from the core and the supporting structure to engage a sealing surface of the header.

3. The lead assembly of claim 1, wherein the connector further comprises a retention feature for mechanical retention or connection with a corresponding feature in the header to retain insertion of the connector in the header.

4. The lead assembly of claim 1, wherein the predetermined shape or profile is a square shaped profile having quadruple planar sectors, and one or more contacts of the contacts are arranged in each sector of the quadruple planar sectors.

5. The lead assembly of claim 4, wherein the connector further comprises one or more additional contacts with impedance, resistive, or ohmic fiducials to provide orientation queues of the contacts.

6. The lead assembly of claim 1, wherein the connector further comprises multiple sectors extending along the surface of the first dielectric layer, and one or more contacts of the conductive contacts are arranged in each sector of the multiple sectors.

7. The lead assembly of claim 6, wherein the conductive contacts are arranged as split annular rings positioned around an axis of the connector and exposed on the surface of the first dielectric layer, and a first portion of the split annular rings is disposed in a first sector of the multiple sectors and a second portion of the split annular rings is disposed in a second sector of the multiple sectors.

8. The lead assembly of claim 6, wherein the predetermined shape or profile is a "D"-shaped profile, the contacts are arranged as split rings on the surface of the first layer of dielectric material in the curved portion of the "D"-shaped profile, and the flat portion of the "D"-shaped profile is an indexing feature for keying during insertion of the connector into the header.

9. The lead assembly of claim 6, wherein the predetermined shape or profile is a notched profile, the contacts are arranged as split rings on the surface of the first layer of dielectric material in a curved portion of the notched profile, and a notch of the notched profile is an indexing feature for keying during insertion of the connector into the header.

10. The lead assembly of claim 9, wherein a first portion of the split annular rings is disposed in a first sector of the multiple sectors and a second portion of the split annular rings is disposed in a second sector of the multiple sectors.

11. The lead assembly of claim 9, wherein each split annular ring is spaced apart from one another on the surface by a region of the first layer of the dielectric material.

12. A header and lead assembly comprising:
a connector comprising a core and a first supporting structure wrapped around at least a portion of the core, wherein:
the first supporting structure comprises a first layer of dielectric material and a second layer of dielectric material;
the first layer of dielectric material is a high temperature liquid crystal polymer;
the second layer of dielectric material is a low temperature liquid crystal polymer that is reflowed to attach the first supporting structure to the core;
first conductive traces are buried between the first layer of dielectric material and the second layer of dielectric material;
the first conductive traces terminate at first conductive contacts formed on a surface of the first dielectric layer; and
the connector has a first predetermined shape or profile;
a header comprising a second supporting structure, wherein:
the second supporting structure comprises one or more layers of polymer;
second conductive traces are buried between the one or more layers of polymer;
the second conductive traces terminate at second conductive contacts formed on a surface of the one or more layers of polymer; and
the header has a second predetermined shape or profile structured to receive the first predetermined shape or profile of the connector; and
a clip structured to hold the first conductive contacts in electrical contact with the second conductive contacts.

13. The header and lead assembly of claim 12, wherein the first predetermined shape or profile is a blade shape with the first supporting structure folded over the core, and the first conductive contacts face outward on the surface of the first layer of dielectric material.

14. The header and lead assembly of claim 12, wherein the clip is one or more clip springs or spring-fibers arranged into a comb or rib-cage arrangement on an outside of the second supporting structure, and the clip springs or spring-fibers have a spring force that exerts a clasping pressure on the second supporting structure to electrically connect the header to the connector.

15. The header and lead assembly of claim 14, further comprising a cable comprising a proximal end, a distal end, and third conductive traces, wherein the connector is located at the proximal end of the cable.

16. The header and lead assembly of claim 15, further comprising an electrode assembly located at the distal end of the cable, the electrode assembly comprising electrodes electrically connected to the second conductive traces via the third conductive traces, the first conductive traces, the first conductive contacts, and the second conductive contacts.

17. The header and lead assembly of claim 12, wherein the connector further comprises multiple sectors extending along the surface of the first layer of dielectric material, and one or more contacts of the first conductive contacts are arranged in each sector of the multiple sectors.

18. The header and lead assembly of claim 17, wherein the first conductive contacts are arranged as split rows positioned in columns and exposed on the surface of the first layer of dielectric material, and a first portion of the split rows is disposed in a first sector of the multiple sectors and a second portion of the split rows is disposed in a second sector of the multiple sectors.

19. The header and lead assembly of claim 18, wherein the first sector is located on a first side of the connector and the second sector is located on a second side of the connector.

20. A lead assembly comprising:
a first cable comprising a proximal end and a distal end;
a second cable comprising a proximal end and a distal end;
a connection assembly comprising:
a first connector comprising a core and a first supporting structure wrapped around at least a portion of the core, wherein:
the first connector is located at the proximal end of the first cable;
the first supporting structure comprises a first layer of dielectric material and a second layer of dielectric material;
the first layer of dielectric material is a high temperature liquid crystal polymer;
the second layer of dielectric material is a low temperature liquid crystal polymer that is reflowed to attach the first supporting structure to the core;
first conductive traces are buried between the first layer of dielectric material and the second layer of dielectric material; and
the first conductive traces terminate at first conductive contacts formed on a surface of the first layer of dielectric material;
a second connector comprising a second supporting structure, wherein:
the second connector is located at the distal end of the second cable;
the second supporting structure comprises a one or more layers of polymer;

second conductive traces are buried between the one or more layers of polymer; and the second conductive traces terminate at second conductive contacts formed on a surface of the one or more layers of polymer; and one or more attachment features that hold the first connector in physical contact with the second connector such that the first conductive contacts are in electrical contact with the second conductive contacts.

* * * * *